US008748695B2

(12) United States Patent
Chaky et al.

(10) Patent No.: US 8,748,695 B2
(45) Date of Patent: *Jun. 10, 2014

(54) MOLECULAR MARKERS LINKED TO PPO INHIBITOR TOLERANCE IN SOYBEANS

(75) Inventors: Julian Chaky, Urbandale, IA (US); Kevin A. Fengler, Wilmington, DE (US); Jennifer A. Klaiber, Urbandale, IA (US); Donald Kyle, Princeton, IL (US); Bailin Li, Hockessin, DE (US); Mark D. Vogt, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 456 days.

This patent is subject to a terminal disclaimer.

(21) Appl. No.: 12/694,255

(22) Filed: Jan. 26, 2010

(65) Prior Publication Data

US 2010/0186131 A1    Jul. 22, 2010

Related U.S. Application Data

(63) Continuation-in-part of application No. 12/506,498, filed on Jul. 21, 2009.

(60) Provisional application No. 61/083,038, filed on Jul. 23, 2008.

(51) Int. Cl.
*A01H 1/02* (2006.01)
*A01H 1/04* (2006.01)
*A01H 5/10* (2006.01)

(52) U.S. Cl.
USPC ........... 800/266; 800/267; 800/265; 800/279; 800/300; 800/312

(58) Field of Classification Search
None
See application file for complete search history.

(56) References Cited

U.S. PATENT DOCUMENTS

| | | | |
|---|---|---|---|
| 4,761,037 A | 8/1988 | Anderson et al. | |
| 5,013,659 A | 5/1991 | Bedbrook et al. | |
| 5,141,870 A | 8/1992 | Bedbrook et al. | |
| 5,304,732 A | 4/1994 | Anderson et al. | |
| 5,331,107 A | 7/1994 | Anderson et al. | |
| 5,378,824 A | 1/1995 | Bedbrook et al. | |
| 5,489,520 A | 2/1996 | Adams et al. | |
| 5,550,318 A | 8/1996 | Adams et al. | |
| 5,561,236 A | 10/1996 | Leemans et al. | |
| 5,605,011 A | 2/1997 | Bedbrook et al. | |
| 5,646,024 A | 7/1997 | Leemans et al. | |
| 5,648,477 A | 7/1997 | Leemans et al. | |
| 5,731,180 A | 3/1998 | Dietrich | |
| 5,767,361 A | 6/1998 | Dietrich | |
| 5,767,373 A | 6/1998 | Ward et al. | |
| 5,874,265 A | 2/1999 | Adams et al. | |
| 5,879,903 A | 3/1999 | Strauch | |
| 5,919,675 A | 7/1999 | Adams et al. | |
| 5,928,937 A | 7/1999 | Kakefuda et al. | |
| 5,969,213 A | 10/1999 | Adams et al. | |
| 6,069,115 A | 5/2000 | Pallett et al. | |
| 6,177,616 B1 | 1/2001 | Bartsch et al. | |
| 6,245,968 B1 | 6/2001 | Boudec et al. | |
| 6,268,549 B1 | 7/2001 | Sailland et al. | |
| 6,282,837 B1 | 9/2001 | Ward et al. | |
| 6,288,306 B1 | 9/2001 | Ward et al. | |
| 6,307,129 B1 | 10/2001 | Ward et al. | |
| 7,563,950 B2 * | 7/2009 | Matsushima et al. | 800/300 |
| 2006/0041951 A1 * | 2/2006 | Sebastian et al. | 800/278 |

FOREIGN PATENT DOCUMENTS

| | | |
|---|---|---|
| WO | WO 96/33270 | 10/1996 |
| WO | WO 99/23886 | 5/1999 |
| WO | WO 01/12825 | 2/2001 |
| WO | WO 2005/107437 | 11/2005 |
| WO | 2006/017840 A | 2/2006 |
| WO | WO 2006/017840 | 2/2006 |
| WO | WO 2010/011803 | 1/2010 |

OTHER PUBLICATIONS

Michel Matringe, Jean-Michel Camadro, Pierre Labbe and Rene Scalla,Protoporphyrinogen oxidase as a molecular target for diphenyl ether herbicides, Biochem. J. (1989) 260, 231-235 (Printed in Great Britain), 5 pages.*
Henikoff, et al., "Amino acid substitution matrices from protein blocks" Proc. Natl. Acad. Sci. USA, vol. 89, pp. 10915-10919 (1992).
Herman, et al., "A Three-component Dicamba O-Demethylase from *Pseudomonas maltophilia*, Strain DI-6: Gene Isolation . . . ", J. Biol. Chem., vol. 280, pp. 24759-24767 (2005).
Needleman, et al., "A general method applicable to the search for similarities in the amino acid sequence of two proteins", J. Mol. Biol., vol. 48, pp. 443-453 (1970).
Retzinger, et al., "Classification of herbicides by site of action for weed resistance management strategies", Weed Technology, vol. 11, pp. 383-393 (1997).
Copending U.S. Appl. No. 12/506,498, filed Jul. 21, 2009.
Copending U.S. Appl. No. 13/013,332, filed Jan. 25, 2011.
Copending U.S. Appl. No. 13/013,139, filed Jan. 25, 2011.
Choi, et al., A Soybean Transcript Map: Gene Distribution, Haplotype and Single-Nucleotide Polymorphism Analysis (2007) Genetics 176:685-96.

(Continued)

*Primary Examiner* — David T Fox
*Assistant Examiner* — Jared Shapiro

(57) ABSTRACT

This invention relates generally to the detection of genetic differences among soybeans. More particularly, the invention relates to soybean quantitative trait loci (QTL) for tolerance to protoporphyrinogen oxidase inhibitors, to soybean plants possessing these QTLs, which map to a novel chromosomal region, and to genetic markers that are indicative of phenotypes associated with protoporphyrinogen oxidase inhibitor tolerance. Methods and compositions for use of these markers in genotyping of soybean and selection are also disclosed.

26 Claims, 11 Drawing Sheets

(56) References Cited

OTHER PUBLICATIONS

Cregan, P.B. et al., An Integrated Genetic Linkage Map of the Soybean Genome (1999) Crop Science 39:1464-90.
Dayan et al (1997) Soybean (*Glycine max*) cultivar differences in response to sulfentrazone; Weed Science 45:634-641.
Hulting et al.; Soybean (*Glycine max* (L.) Merr.) cultivar tolerance to sulfentrazone. (2001) Science Direct, vol. 20(8): 679-683.
Li, Z. et al.; Physiological basis for the differential tolerance of Glycine Max to sulfentrazone during seed germination; Weed Science, 48:281-285 (2000).
Li, Z., et al., Using electyrolyte leakage to detect soybean (*Glycine max*) cultivars sensitve to sulfentrazone, Weed Technology, Champaign, IL, US 14(4):699-704 (2000). XPO.
Swantek, J.M., et al., Evaluation of soybean injury from sulfentrazone and inheritance of tolerance, Weed Science, Weed Science Society of America, Champaign, IL, US, 46(2):2.
Taylor-Lovell et al, Phytoxic Response and Yield of Soybean (*Glycine max*) Varieties Treated with Sulfentrazone or Flumioxazin (2001) Weed Technology 15:95-102.
PCT International Search Report, Pioneer Hi-Bred International, Inc., PCT/US2009/051483, mailed Oct. 13, 2009, 5 pages.
Shoemaker and Olsen, ((1993) Molecular Linkage Map of Soybean (*Glycine max* L. Merr.). p. 6.131-6.138. In S.J. O'Brien (ed.) Genetic Maps: Locus Maps of Complex Genomes . . . .
Shoemaker R.C., 1994 RFLP Map of Soybean. p. 299-309 In R.L. Phillips and I.K. Vasil (ed.) DNA-based markers in plants. Kluwer Academic Press Dordrecht, the Netherlands.
Hulting, A.G., et al., "Soybean (*Glycine max* (L.) Merr.) cultivar tolerance to sulfentrazone", Crop Protection, 20 (8):679-683 (2001). XP002547823.
Dayan, F.E. et al., "Soybean (*Glycine max*) cultivar differences in response to sulfentrazone", Weed Science, Weed Science Society of America, Champaign, IL, US, 45(5):634-641 (1997). XP009123163.
Li, Z., et al., "Using electrolyte leakage to detect soybean (*Glycine max*) cultivars sensitive to sulfentrazone", Weed Technology, Champaign, IL, US, 14(4):699-704 (2000). XP009123189.
Li, Zhaohu et al., "Physiological basis for the differential tolerance of *Glycine max* to sulfentrazone during seed germination", Weed Science, 48:281-285, 2000.
Swantek, J.M., et al., "Evaluation of soybean injury from sulfentrazone and inheritance of tolerance", Weed Science, Weed Science Society of America, Champaign, IL, US, 46(2):271-277 (1988). XP009123188.
Taylor-Lovell, Sarah et al., "Phytotoxic Response and Yield of Soybean (*Glycine max*) Varieties Treated with Sulfentrazone or Flumioxazin" Weed Technology, 2001. vol. 15:95-102.

* cited by examiner

| Marker | Linkage Group | Position | Type |
|---|---|---|---|
| SATT495 | L | 0.00 | SSR |
| SATT723 | L | 0.44 | SSR |
| SAT_408 | L | 1.00 | SSR |
| S08102-1-Q1 S08103-1-Q1 S08104-1-Q1 S08106-1-Q1 S08107-1-Q1 S08107-1-Q1 S08109-1-Q1 S08110-1-Q1 S08111-1-Q1 S08115-2-Q1 S08117-1-Q1 S08119-1-Q1 S08116-1-Q1 S08112-1-Q1 S08108-1-Q1 S08101-4-Q1 S08101-1-Q1 S08101-2-Q1 S08101-3-Q1 | L | | SNP |
| Sat_301 | L | 10.31 | SSR |
| SATT446 | L | 11.13 | SSR |
| P10649C-3 | L | 12.5 | ASH |
| SATT232 | L | 12.55 | SSR |
| S08105-1-Q1 | L | | SNP |
| SATT182 | L | 13.90 | SSR |
| S08010-1-Q1 S08010-2-Q1 | L | | SNP |
| SATT238 | L | 19.41 | SSR |
| Sat_071 | L | 20.04 | SSR |
| SATT388 | L | 21.61 | SSR |
| SATT497 | L | 26.06 | SSR |
| SATT313 | L | 27.35 | SSR |
| SATT143 | L | 28.16 | SSR |
| Sat_397 | L | 28.26 | SSR |
| SATT418 | L | 28.57 | SSR |
| Sat_134 | L | 28.66 | SSR |
| SATT652 | L | 28.67 | SSR |
| SATT711 | L | 28.67 | SSR |

*FIG. 1A*

| Sat_187 | L | 28.68 | SSR |
|---|---|---|---|
| Sat_195 | L | 28.68 | SSR |
| Sat_388 | L | 28.71 | SSR |
| SATT694 | L | 28.71 | SSR |
| SATT398 | L | 28.90 | SSR |
| Sat_191 | L | 29.19 | SSR |
| Sat_405 | L | 29.40 | SSR |
| Sat_320 | L | 29.74 | SSR |
| SATT523 | L | 30.18 | SSR |
| SATT278 | L | 30.34 | SSR |
| SATT613 | L | 32.64 | SSR |

FIG. 1A (CONTINUED)

| Linked Markers | | | | | |
|---|---|---|---|---|---|
| SATT495 | SATT723 | Sat_408 | A169_1 | EV2_1 | Sle3_4s |
| BLT010_2 | BLT007_1 | SATT232 | Sat_301 | SATT446 | SATT182 |
| R176_1 | JUBC090 | SATT238 | Sat_071 | BLT039_1 | Bng071_1 |
| SATT388 | A264_1 | RGA_7 | RGA7 | SATT523 | Sat_134 |
| LbA | i8_2 | A450_2 | A106_1 | Sat_405 | SATT143 |
| B124_2 | A459_1 | SATT398 | SATT694 | Sat_195 | Sat_388 |
| SATT652 | SATT711 | Sat_187 | SATT418 | SATT278 | Sat_397 |
| Sat_191 | Sat_320 | O109_1 | A204_2 | SATT497 | G214_17 |
| SATT313 | B164_1 | G214_16 | SATT613 | A023_1 | SATT284 |
| AW508247 | SATT462 | L050_7 | E014_1 | A071_5 | B046_1 |
| L1 | B162_2 | | | | |

*FIG. 1B*

| Marker | Linkage Group | Position | Type |
|---|---|---|---|
| Sat_379 | N | 2.70 | SSR |
| SCT_195 | N | 4.63 | SSR |
| SATT631 | N | 20.31 | SSR |
| SATT159 | N | 21.76 | SSR |
| SATT009 | N | 22.42 | SSR |
| SATT641 | N | 23.32 | SSR |
| Sat_186 | N | 23.91 | SSR |
| SATT152 | N | 24.79 | SSR |
| S60167-TB | N | 26.00 | SSR |
| SATT530 | N | 27.41 | SSR |
| SATT675 | N | 28.92 | SSR |
| SATT683 | N | 28.96 | SSR |
| SATT624 | N | 29.55 | SSR |
| SATT393 | N | 29.64 | SSR |
| SATT125 | N | 30.30 | SSR |
| SATT485 | N | 30.30 | SSR |
| SATT584 | N | 30.64 | SSR |
| Sat_166 | N | 31.09 | SSR |
| Sat_084 | N | 31.36 | SSR |
| Sat_275 | N | 33.84 | SSR |
| Sat_208 | N | 35.48 | SSR |
| Sat_280 | N | 36.82 | SSR |
| SATT080 | N | 38.56 | SSR |
| Sat_266 | N | 40.02 | SSR |
| SATT387 | N | 45.03 | SSR |

FIG. 2A

| Linked Markers | | | | |
|---|---|---|---|---|
| SCT_195 | Sat_379 | A071_10 | A071_3 | A071_4 |
| A071_6 | AC_telo | Rps7 | R022_1 | L050_12 |
| SATT152 | OP_N03 | BLT004_1 | SATT631 | SATT159 |
| SATT009 | SATT641 | RGA6a | Sat_186 | A071_2 |
| K418_1 | Rps1 | K395_2 | OPAC12b | SATT530 |
| gc34_2 | SATT683 | SATT675 | A280_1 | SATT624 |
| A426_2 | Sle_003 | i4_2 | Sat_084 | SATT393 |
| SATT584 | SATT485 | Sat_166 | Sat_208 | BLT049_1 |
| Bng095_2 | OP_F13 | SATT125 | Sat_275 | Sle2_3 |
| Mng456_1 | RGA6b | OP_U09b | mO128_1 | Sat_280 |
| SATT080 | Sat_266 | L103_1 | B162_1 | peG488_2 |
| SATT387 | Rpg4 | Sat_236 | Sat_033 | |

FIG. 2B

| Marker Name | Left Primer Sequence | Right Primer Sequence | Pigtail |
|---|---|---|---|
| S60167-TB LG-N | TTATTGAGGTGGGCAAGGTGTG (SEQ ID NO: 1) | CATGAAGTCTGGTGGTTGAACA (SEQ ID NO: 2) | GTTTCTT |
| SATT523 LG-L | GCGATTTCTTCCTTGAAGAATTTCTG (SEQ ID NO: 3) | GCGCTTTTCGGCTGTTATTTTAACT (SEQ ID NO: 4) | GTTTCTT |

FIG. 3

| Marker Name | PCR Primers | Allele Probes |
|---|---|---|
| P10649C-3 LG-L | Primer Seq 1 (SEQ ID NO. 5): GAGGGCTATGTTTCTTCTCCAGATGTGAG<br>Primer Seq 2 (SEQ ID NO. 6): AAGGTCGGCTTGGTGTTAAAGGCAG | Allele 1 Probe (SEQ ID NO. 7): TCATcTgTGATAA<br>Allele 2 Probe (SEQ ID NO. 8): TCATgTgTGATAA<br>Allele 3 Probe (SEQ ID NO. 9): TCATcTcTGATAA |
| S00224-1 LG-L | Primer Seq 1 (F) (SEQ ID NO. 10): CTGGACCTACCCGGGATGAAAA<br>Primer Seq 2 (R) (SEQ ID NO. 11): TCTTCCTCTCCCTCCTCCTCGC | Allele 1 Probe (PF1) (SEQ ID NO. 12): CGCGAcTCTCCTC<br>Allele 2 Probe (PV1) (SEQ ID NO. 13): CGCGAgTCTCCTC |
| P5467-1 LG-N | Primer Seq 1 (SEQ ID NO. 14): TCCCAGGTTAGATTTCTGAACGAAGA<br>Primer Seq 2 (SEQ ID NO. 15): CATCAGCACACAAAAGGGCATCCTCA | Allele 1 Probe (SEQ ID NO. 16): CACTCCTTAAGgTAAT<br>Allele 2 Probe (SEQ ID NO. 17): CACTCCTTAAGaTAAT |
| S08101-1-Q1 LG-L | Primer Seq 1 (F) (SEQ ID NO. 18): gttatcgtcaccacacaa<br>Primer Seq 2 (R) (SEQ ID NO. 19): cacaacacgagtagccgtagg | Allele 1 Probe (PF1) (SEQ ID NO. 20): aacggAtcatcacaac<br>Allele 2 Probe (PV1) (SEQ ID NO. 21): aacggCtcatcacaa |
| S08101-2-Q1 LG-L | Primer Seq 1 (F) (SEQ ID NO. 22): cgacaatggccttacacct<br>Primer Seq 2 (R) (SEQ ID NO. 23): tcgatatggacgaaggagga | Allele 1 Probe (PF1) (SEQ ID NO. 24): acaccAttttcatcc<br>Allele 2 Probe (PV1) (SEQ ID NO. 25): acaccCttttcatcc |
| S08101-3-Q1 LG-L | Primer Seq 1 (F) (SEQ ID NO. 26): GCAATCACATTGCATTCCTTA<br>Primer Seq 2 (R) (SEQ ID NO. 27): TCTGAACGAGTTGTGCAAGAA | Allele 1 Probe (PF1) (SEQ ID NO. 28): actgctGctttgtcta<br>Allele 2 Probe (PV1) (SEQ ID NO. 29): ctactgctActttgtc |

FIG. 4

| Marker Name | PCR Primers | Allele Probes |
|---|---|---|
| S08101-4-Q1 LG-L | Primer Seq 1 (F) (SEQ ID NO. 30): acctcgtattggtggtgtg<br>Primer Seq 2 (R) (SEQ ID NO. 31): gaatgttcagtgcgagcaac | Allele 1 Probe (PF1) (SEQ ID NO. 32) acttccctcGtttcg<br>Allele 2 Probe (PV1) (SEQ ID NO. 33) cttccctcAtttcg |
| S08102-1-Q1 LG-L | Primer Seq 1 (F) (SEQ ID NO. 34): caaaaggaaagaagaaccgtgt<br>Primer Seq 2 (R) (SEQ ID NO. 35): tccaacctatgtgttggtgtg | Allele 1 Probe (PF1) (SEQ ID NO. 36) atgattgaagcagGaaa<br>Allele 2 Probe (PV1) (SEQ ID NO. 37) tcatgattgaagcagCaa |
| S08103-1-Q1 LG-L | Primer Seq 1 (F) (SEQ ID NO. 38): ggagacttgacttaaagagaagaaaa<br>Primer Seq 2 (R) (SEQ ID NO. 39): cggaaagaaaaacaatagattgaatg | Allele 1 Probe (PF1) (SEQ ID NO. 40) cttgttctagactgatCat<br>Allele 2 Probe (PV1) (SEQ ID NO. 41) ctagactgatAattca |
| S08104-1-Q1 LG-L | Primer Seq 1 (F) (SEQ ID NO. 42): tcattcaagactacatgaaagacaaa<br>Primer Seq 2 (R) (SEQ ID NO. 43): caagggagagcaatccttga | Allele 1 Probe (PF1) (SEQ ID NO. 44) atagtctcCcaaacac<br>Allele 2 Probe (PV1) (SEQ ID NO. 45) atagctctcTcaaacacc |
| S08105-1-Q1 LG-L | Primer Seq 1 (F) (SEQ ID NO. 46): gaaactttccattttgccctc<br>Primer Seq 2 (R) (SEQ ID NO. 47): agaacgcagggagaagc | Allele 1 Probe (PF1) (SEQ ID NO. 48) cttcttCcactcttac<br>Allele 2 Probe (PV1) (SEQ ID NO. 49) ccttcttAcactcttac |
| S08106-1-Q1 LG-L | Primer Seq 1 (F) (SEQ ID NO. 50): tgatatgacactctactaagatgtgttg<br>Primer Seq 2 (R) (SEQ ID NO. 51): tgattcatccgcaaacttga | Allele 1 Probe (PF1) (SEQ ID NO. 52) cactctcctaTattgtc<br>Allele 2 Probe (PV1) (SEQ ID NO. 53) ctctcctaCattgtca |
| S08107-1-Q1 LG-L | Primer Seq 1 (F) (SEQ ID NO. 54): agatccttgttccaaattccaa<br>Primer Seq 2 (R) (SEQ ID NO. 55): ccttgccttaatgggtgtgt | Allele 1 Probe (PF1) (SEQ ID NO. 56) ccaacacaatcTaact<br>Allele 2 Probe (PV1) (SEQ ID NO. 57) ccaacacaatcGaa |

*FIG. 4 (CONTINUED)*

| Marker Name | PCR Primers | Allele Probes |
|---|---|---|
| S08108-1-Q1 LG-L | Primer Seq 1 (F) (SEQ ID NO. 58): atggagcaagcttgtgttt<br>Primer Seq 2 (R) (SEQ ID NO. 59): catgctaccagcatctgcaa | Allele 1 Probe (PF1) (SEQ ID NO. 60): cttcataaaCgccaaag<br>Allele 2 Probe (PV1) (SEQ ID NO. 61): cataaaTgccaaagca |
| S08109-1-Q1 LG-L | Primer Seq 1 (F) (SEQ ID NO. 62): aatgagcaaggagaggaca<br>Primer Seq 2 (R) (SEQ ID NO. 63): tcgccgtgctatttaattt | Allele 1 Probe (PF1) (SEQ ID NO. 64): aagcacTactttcaattg<br>Allele 2 Probe (PV1) (SEQ ID NO. 65): aagcacCactttca |
| S08110-1-Q1 LG-L | Primer Seq 1 (F) (SEQ ID NO. 66): agatgccttgctcagtggac<br>Primer Seq 2 (R) (SEQ ID NO. 67): atgatgaatgtgttgagccaat | Allele 1 Probe (PF1) (SEQ ID NO. 68): ccccaTcaccatac<br>Allele 2 Probe (PV1) (SEQ ID NO. 69): accccaCcaccata |
| S08111-1-Q1 LG-L | Primer Seq 1 (F) (SEQ ID NO. 70): agaaacctttccaaagtcttgg<br>Primer Seq 2 (R) (SEQ ID NO. 71): tagggaggcacttgacaacc | Allele 1 Probe (PF1) (SEQ ID NO. 72): caacatcCgagtcca<br>Allele 2 Probe (PV1) (SEQ ID NO. 73): caacatcAgagtcca |
| S08112-1-Q1 LG-L | Primer Seq 1 (F) (SEQ ID NO. 74): ttttgaccccagagagttg<br>Primer Seq 2 (R) (SEQ ID NO. 75): ttgcaagcctaaaggatggt | Allele 1 Probe (PF1) (SEQ ID NO. 76): ctatctcTacacgatgtgt<br>Allele 2 Probe (PV1) (SEQ ID NO. 77): ctatctcCacacgatg |
| S08115-2-Q1 LG-L | Primer Seq 1 (F) (SEQ ID NO. 78): tcccactttgatcttgcagaa<br>Primer Seq 2 (R) (SEQ ID NO. 79): tacggtgggtggattattcg | Allele 1 Probe (PF1) (SEQ ID NO. 80): cctccaatGgcatac<br>Allele 2 Probe (PV1) (SEQ ID NO. 81): cctccaatAgcatacat |
| S08116-1-Q1 LG-L | Primer Seq 1 (F) (SEQ ID NO. 82): agaaaagcagcagaaagaggac<br>Primer Seq 2 (R) (SEQ ID NO. 83): cttcatgaatccaacatcaga | Allele 1 Probe (PF1) (SEQ ID NO. 84): ctctaattCcacatctg<br>Allele 2 Probe (PV1) (SEQ ID NO. 85): cctctaattTcacatctg |

*FIG. 4 (CONTINUED)*

| Marker Name | PCR Primers | Allele Probes |
|---|---|---|
| S08117-1-Q1 LG-L | Primer Seq 1 (F) (SEQ ID NO. 86): tcaaaccatttgtttccagt<br>Primer Seq 2 (R) (SEQ ID NO. 87): tgctagccttgataccaac | Allele 1 Probe (PF1) (SEQ ID NO. 88) ttgcattgtattCtct<br>Allele 2 Probe (PV1) (SEQ ID NO. 89) ttgcattgtattTtc |
| S08118-1-Q1 LG-L | Primer Seq 1 (F) (SEQ ID NO. 90): gtctcaggcagtgaatctgct<br>Primer Seq 2 (R) (SEQ ID NO. 91): cagccttaccaactcaacatcg | Allele 1 Probe (PF1) (SEQ ID NO. 92) ttccgTgaagatc<br>Allele 2 Probe (PV1) (SEQ ID NO. 93) atgcttccgCgaaga |
| S08119-1-Q1 LG-L | Primer Seq 1 (F) (SEQ ID NO. 94): ggtagcagttactttgtgatgtaagc<br>Primer Seq 2 (R) (SEQ ID NO. 95): catgcaataaaatccaaaacca | Allele 1 Probe (PF1) (SEQ ID NO. 96) tactgaTcacagttat<br>Allele 2 Probe (PV1) (SEQ ID NO. 97) tactgaCcacagttat |
| S04867-1-A LG-L | Primer Seq 1 (F) (SEQ ID NO. 98): ttgctttggaaaggactcca<br>Primer Seq 2 (R) (SEQ ID NO. 99): cctcatcaactcctgctgct | Allele 1 Probe (PF1) (SEQ ID NO. 100) ctcggtgctgtTtt<br>Allele 2 Probe (PV1) (SEQ ID NO. 101) ctcggtgctgtCtt |
| S03859-1-A LG-L | Primer Seq 1 (F) (SEQ ID NO. 102): gaaaccaatttgatgtgaagga<br>Primer Seq 2 (R) (SEQ ID NO. 103): aagtgagagggggtgcaaaga | Allele 1 Probe (PF1) (SEQ ID NO. 104) cagccctAtctcac<br>Allele 2 Probe (PV1) (SEQ ID NO. 105) agccctGtctcact |
| S08010-1-Q1 LG-L | Primer Seq 1 (F) (SEQ ID NO. 106): gcaaatgagaaggctgaagct<br>Primer Seq 2 (R) (SEQ ID NO. 107): gctgtccctcagtccatcc | Allele 1 Probe (PF1) (SEQ ID NO. 108) cggtatcgctcgTca<br>Allele 2 Probe (PV1) (SEQ ID NO. 109) tatcgctcgCcaacg |
| S08010-2-Q1 LG-L | Primer Seq 1 (F) (SEQ ID NO. 110): atccacttgcaagataggacact<br>Primer Seq 2 (R) (SEQ ID NO. 111): gtgtaagtactgatgtgcagttttga | Allele 1 Probe (PF1) (SEQ ID NO. 112) ctttgacattaagact:atcc<br>Allele 2 Probe (PV1) (SEQ ID NO. 113) agactAatccttaaacaag |

FIG. 4 (CONTINUED)

MOLECULAR MARKERS LINKED TO PPO INHIBITOR TOLERANCE IN SOYBEANS

CROSS-REFERENCE TO RELATED APPLICATIONS

This application is a continuation-in-part of application Ser. No. 12/506,498, filed Jul. 21, 2009, which claims priority under 35 U.S.C. §119(e) to provisional application Ser. No. 60/083,038 filed Jul. 23, 2008, herein incorporated by reference in their entirety.

FIELD OF THE INVENTION

This invention relates generally to the detection of genetic differences among soybeans.

BACKGROUND OF THE INVENTION

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications. Weed management in soybean fields is important to maximizing yields. A recent development in soybean technology has been the development of herbicide-tolerant soybean varieties. Glyphosate tolerant soybeans were commercially introduced in 1996 and accounted for more than 85% percent of U.S. soybean acreage in 2007.

Some weeds are starting to show increased tolerance to glyphosate. This increased tolerance decreases the effectiveness of glyphosate application and results in lower yields for farmers. As a result there is a need in the art for soybean varieties that are tolerant to other herbicide chemistry.

SUMMARY OF THE INVENTION

This invention relates generally to the detection of genetic differences among soybeans. More particularly, the invention relates to soybean quantitative trait loci (QTL) for tolerance to protoporphyrinogen oxidase (PPOase) inhibitors, to soybean plants possessing these QTLs, which map to a novel chromosomal region, and to genetic markers that are indicative of phenotypes associated with protoporphyrinogen oxidase inhibitor tolerance. Methods and compositions for use of these markers in genotyping of soybean and selection are also disclosed.

A novel method is provided for determining the presence or absence in soybean germplasm of a QTL associated with tolerance to protoporphyrinogen oxidase inhibitors. The tolerance trait has been found to be closely linked to a number of molecular markers that map to linkage groups L and N. Soybean plants, seeds, tissue cultures, variants and mutants having tolerance to protoporphyrinogen oxidase inhibitors produced by the foregoing methods are also provided in this invention.

The QTL associated with tolerance to protoporphyrinogen oxidase inhibitors maps to soybean linkage group L and/or N. These QTL may be mapped by one or more molecular markers. For linkage group L, the markers include SATT495, P10649C-3, SATT182, SATT388, SATT313, SATT613, S08102-1-Q1, S08103-1-Q1. S08104-1-Q1, S08106-1-Q1, S08107-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, and S08101-3-Q1, or markers closely linked thereto. Other markers of linkage group L may also be used to identify the presence or absence of the gene, including other markers above marker SATT613. For linkage group N, the markers include Sat_379, SCT_195, SATT631, S60167-TB, SATT675, SATT624, SATT080, SATT387, or markers closely linked thereto. Other markers of linkage group N may also be used to identify the presence or absence of the gene, including other markers above marker SATT387.

The information disclosed herein regarding the QTL for tolerance to protoporphyrinogen oxidase inhibitors which maps to soybean linkage group L and/or N is used to aid in the selection of breeding plants, lines and populations containing tolerance to protoporphyrinogen oxidase inhibitors for use in introgression of this trait into elite soybean germplasm, or germplasm of proven genetic superiority suitable for variety release.

Also provided is a method for introgressing a soybean QTL associated with tolerance to protoporphyrinogen oxidase inhibitors into non-tolerant soybean germplasm or less tolerant soybean germplasm. According to the method, nucleic acid markers mapping the QTL are used to select soybean plants containing the QTL. Plants so selected have a high probability of expressing the trait tolerance to protoporphyrinogen oxidase inhibitors. Plants so selected can be used in a soybean breeding program. Through the process of introgression, the QTL associated with tolerance to protoporphyrinogen oxidase inhibitors is introduced from plants identified using marker-assisted selection to other plants. According to the method, agronomically desirable plants and seeds can be produced containing the QTL associated with tolerance to protoporphyrinogen oxidase inhibitors from germplasm containing the QTL. Sources of tolerance to protoporphyrinogen oxidase inhibitors are disclosed below.

Also provided herein is a method for producing a soybean plant adapted for conferring tolerance to protoporphyrinogen oxidase inhibitors. First, donor soybean plants for a parental line containing the tolerance QTL are selected. According to the method, selection can be accomplished via nucleic acid marker-associated selection as explained herein. Selected plant material may represent, among others, an inbred line, a hybrid, a heterogeneous population of soybean plants, or simply an individual plant. According to techniques well known in the art of plant breeding, this donor parental line is crossed with a second parental line. Typically, the second parental line is a high yielding line. This cross produces a segregating plant population composed of genetically heterogeneous plants. Plants of the segregating plant population are screened for the tolerance QTL and are subjected to further breeding. This further breeding may include, among other techniques, additional crosses with other lines, hybrids, backcrossing, or self-crossing. The result is a line of soybean plants that is tolerant to protoporphyrinogen oxidase inhibitors and also has other desirable traits from one or more other soybean lines.

Also provided is a method for introgressing a soybean QTL associated with tolerance or sensitivity to protoporphyrinogen oxidase inhibitors into non-tolerant soybean germplasm or less tolerant soybean germplasm. According to the method, nucleic acid markers mapping the QTL are used to select soybean plants containing the QTL. Plants so selected have a high probability of expressing the trait tolerance or sensitivity to protoporphyrinogen oxidase inhibitors. Plants so selected can be used in a soybean breeding program. Through the process of introgression, the QTL associated with tolerance or sensitivity to protoporphyrinogen oxidase inhibitors is introduced from plants identified using marker-assisted selection to other plants. According to the method, agronomically desirable plants and seeds can be produced containing the QTL associated with tolerance or sensitivity to protoporphyrinogen oxidase inhibitors from germplasm containing the QTL. Sources of tolerance or sensitivity to protoporphyrinogen oxidase inhibitors are disclosed below.

Also provided herein is a method for producing a soybean plant adapted for conferring tolerance or sensitivity to protoporphyrinogen oxidase inhibitors. First, donor soybean plants for a parental line containing the tolerance QTL are selected. According to the method, selection can be accomplished via nucleic acid marker-associated selection as explained herein. Selected plant material may represent, among others, an inbred line, a hybrid, a heterogeneous population of soybean plants, or simply an individual plant.

According to techniques well known in the art of plant breeding, this donor parental line is crossed with a second parental line. Typically, the second parental line is a high yielding line. This cross produces a segregating plant population composed of genetically heterogeneous plants. Plants of the segregating plant population are screened for the tolerance QTL and are subjected to further breeding. This further breeding may include, among other techniques, additional crosses with other lines, hybrids, backcrossing, or self-crossing. The result is a line of soybean plants that is tolerant to mesotrione and/or isoxaflutole herbicides, and also has other desirable traits, such as yield, from one or more other soybean lines.

Also described are isolated polynucleotides and isolated polypeptides relevant to tolerance or sensitivity to protoporphyrinogen oxidase inhibitors. Additional traits may also be added to plants having such tolerance or sensitivity, such as additional herbicide tolerance traits, insect tolerance traits, or other transgenic traits. Also described are methods of introgressing a tolerance or susceptibilty allele into a plant, such as by crossing a soybean plant tolerant to an isoflutole herbicide with a soybean plant susceptible to a isoflutole herbicide in order to form a segregating population, screening the segregating population with one or more nucleic acid markers to determine if plants from the segregating population contains at least one SNP selected from the group consisting of an SNP at position #1433, #1559, #1750, #1832, #1932, #2727, #2858, #3027, #3088, #3090, and #3334 of the sequence set forth as SEQ ID NO: 114 as shown in FIG. 3, or a sequence equivalent to SEQ ID NO: 114, and optionally selecting, if present, one or more soybean plants of the segregating population containing the at least one SNP. Alternatively, such tolerance may be transgenically provided by introducing into a plant cell a polynucleotide as disclosed herein operably linked to a promoter functional in the plant cell to produce a transformed plant cell, and optionally selecting a transformed plant cell having the polynucleotide stably incorporated into its genome.

Compositions include isolated polynucleotides encoding ABC transporter polypeptides that confer tolerance to such herbicides, and isolated ABC transporter polypeptides. Compositions include those polynucleotides encoding polypeptides with amino acid substitutions at position V520X, L584X, S611X, K953X, L1030X, and/or G1112X or positions equivalent thereto, as well as polypeptides with amino acid substitutions at position V520X, L584X, S611X, K953X, L1030X, and/or G1112X or positions equivalent thereto. Also useful are isolated polynucleotide variants, polynucleotides encoding polypeptide variants, and polypeptide variants having sequence identity to the appropriate reference sequence, such an ABC transporter polypeptide of at least 60%, 65%, 70%, 75, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.75%.

Soybean plants, seeds, tissue cultures, variants and mutants having tolerance or sensitivity to PPO inhibitor herbicides produced by the foregoing methods are also provided. Also provided herein are methods for controlling weeds in a crop by applying to the crop and any weeds affecting such crop an effective amount of such herbicide(s), either pre-emergent or post-emergent, such that the weeds are substantially controlled without substantially negatively impacting the crop.

BRIEF DESCRIPTION OF THE DRAWINGS

The invention can be more fully understood from the following detailed description and the accompanying drawings and Sequence Listing, which form a part of this application.

FIG. 1 Panel A provides an integrated genetic map of soybean markers on linkage group L, including the marker type (SSR or ASH/SNP). The genetic map positions of the markers are indicated in centiMorgans (cM), typically with position zero being the first (most distal) marker on the chromosome. The map includes relative positions for some markers for which higher resolution genetic mapping data was not available; no position in cM is provided. Panel B provides a table listing genetic markers that are linked to the protoporphyrinogen oxidase (PPOase) inhibitor tolerance markers identified on linkage group L. These markers are from the soybean public composite map of Jun. 18, 2008 for linkage group L.

FIG. 2 Panel A provides an integrated genetic map of soybean markers on linkage group N, including the marker type (SSR or ASH/SNP). The genetic map positions of the markers are indicated in centiMorgans (cM), typically with position zero being the first (most distal) marker on the chromosome. Panel B provides a table listing genetic markers that are linked to the protoporphyrinogen oxidase (PPOase) inhibitor tolerance markers identified by the present invention on linkage group N. These markers are from the soybean public composite map of Jun. 18, 2008 for linkage group N.

FIG. 3 provides a table listing SSR markers, including those markers that demonstrated linkage disequilibrium with the protoporphyrinogen oxidase (PPOase) inhibitor tolerance phenotype. The table provides the sequences of the left and right PCR primers used in the SSR marker locus genotyping analysis. Also shown is the pigtail sequence used on the 5' end of the right primer.

FIG. 4 provides a table listing the SNP markers that demonstrated linkage disequilibrium with the protoporphyrinogen oxidase (PPOase) inhibitor tolerance phenotype. The table provides the sequences of the PCR primers used to generate a SNP-containing amplicon, and the allele-specific probes that were used to identify the SNP allele in an allele-specific hybridization assay (ASH assay).

DETAILED DESCRIPTION

Figure 5:
FIG. 5 provides an example of cultivars with vastly different protoporphyrinogen oxidase (PPOase) inhibitor tolerance phenotypes. Shown are field samples, with a non-tolerant variety on the left (white circle: stunted, necrotic) and tolerant variety on the right (normal growth)

It is to be understood that this invention is not limited to particular embodiments or examples, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, include plural referents unless the content clearly dictates otherwise. Thus, for example, reference to "plant," "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Certain definitions used in the specification are provided below. Also in the examples which follow, a number of terms are used. Terms not specifically defined herein should be given their ordinary meaning to those in the art. In order to provide a clear and consistent understanding of the specification and claims, including the scope to be given such terms, the following definitions are provided:

AGRONOMICS, AGRONOMIC TRAITS, and AGRONOMIC PERFORMANCE refer to the traits and underlying genetic elements of a given plant variety that contribute to yield over the course of growing season. Individual agronomic traits include emergence vigor, vegetative vigor, stress tolerance, disease resistance or tolerance, herbicide resistance or tolerance, branching, flowering, seed set, seed size, seed density, standability, threshability and the like.

ALLELE means any of one or more alternative forms of a genetic sequence. In a diploid cell or organism, the two alleles of a given sequence typically occupy corresponding loci on a pair of homologous chromosomes.

The term AMPLIFYING in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

An ANCESTRAL LINE is a parent line used as a source of genes.

An ANCESTRAL POPULATION is a group of ancestors that have contributed the bulk of the genetic variation that was used to develop elite lines.

BACKCROSSING is a process in which a breeder crosses a progeny variety back to one of the parental genotypes one or more times.

BREEDING means the genetic manipulation of living organisms.

The term CHROMOSOME SEGMENT designates a contiguous linear span of genomic DNA that resides in planta on a single chromosome.

CULTIVAR and VARIETY are used synonymously and mean a group of plants within a species (e.g., *Glycine max*) that share certain genetic traits that separate them from the typical form and from other possible varieties within that species. Soybean cultivars are inbred lines produced after several generations of self-pollinations. Individuals within a soybean cultivar are homogeneous, nearly genetically identical, with most loci in the homozygous state.

An ELITE LINE is an agronomically superior line that has resulted from many cycles of breeding and selection for superior agronomic performance. Numerous elite lines are available and known to those of skill in the art of soybean breeding.

An ELITE POPULATION is an assortment of elite individuals or lines that can be used to represent the state of the art in terms of agronomically superior genotypes of a given crop species, such as soybean.

A GENETIC MAP is a description of genetic linkage relationships among loci on one or more chromosomes or linkage groups within a given species, generally depicted in a diagrammatic or tabular form.

GENOTYPE refers to the genetic constitution of a cell or organism.

GERMPLASM means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is HOMOZYGOUS if the individual has only one type of allele at a given locus (e.g., a diploid individual has a copy of the same allele at a locus for each of two homologous chromosomes). An individual is "HETEROZYGOUS" if more than one allele type is present at a given locus (e.g., a diploid individual with one copy each of two different alleles). The term "HOMOGENEITY" indicates that members of a group have the same genotype at one or more specific loci. In contrast, the term "HETEROGENEITY" is used to indicate that individuals within the group differ in genotype at one or more specific loci.

INTROGRESSION means the entry or introduction of a gene, QTL, or trait locus from the genome of one plant into the genome of another plant.

A LINE or a STRAIN is a group of individuals of identical parentage that are generally inbred to some degree and that are generally homozygous and homogeneous at most loci (isogenic or near isogenic). A "SUBLINE" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (yield, tolerance, etc.).

LINKAGE refers to a phenomenon wherein alleles on the same chromosome tend to segregate together more often than expected by chance if their transmission was independent.

Genetic recombination occurs with an assumed random frequency over the entire genome. Genetic maps are constructed by measuring the frequency of recombination between pairs of traits or markers. The closer the traits or markers lie to each other on the chromosome, the lower the frequency of recombination, and the greater the degree of linkage. Traits or markers are considered herein to be linked if they generally co-segregate. A 1/100 probability of recombination per generation is defined as a map distance of 1.0 centiMorgan (1.0 cM). For example, in soybean, 1 cM correlates, on average, to about 400,000 base pairs (400 Kb).

The genetic elements or genes located on a single chromosome segment are physically linked. In the context of the present invention the genetic elements located within a chromosome segment are also genetically linked, typically within a genetic recombination distance of less than or equal to 50 centimorgans (cM), e.g., about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less.

LINKAGE GROUP refers to traits or markers that generally co-segregate. A linkage group generally corresponds to a chromosomal region containing genetic material that encodes the traits or markers.

LOCUS is a defined segment of DNA.

A MAP LOCATION is an assigned location on a genetic map relative to linked genetic markers where a specified marker can be found within a given species. Markers are frequently described as being "above" or "below" other markers on the same linkage group; a marker is "above" another marker if it appears earlier on the linkage group, whereas a marker is "below" another marker if it appears later on the linkage group.

MAPPING is the process of defining the linkage relationships of loci through the use of genetic markers, populations segregating for the markers, and standard genetic principles of recombination frequency.

MOLECULAR MARKER is a nucleic acid or amino acid sequence that is sufficiently unique to characterize a specific locus on the genome. Examples include Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers are known to the art, and phenotypic traits may also be used as markers in the methods. All markers are used to define a specific locus on the soybean genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage where the trait can be expressed. Molecular markers have been widely used to determine genetic composition in soybeans. Shoemaker and Olsen, ((1993) Molecular Linkage Map of Soybean (*Glycine max* L. Men.). p. 6.131-6.138. In S. J. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also Shoemaker R. C. 1994 RFLP Map of Soybean. P. 299-309 In R. L. Phillips and I. K. Vasil (ed.) DNA-based markers in plants. Kluwer Academic Press Dordrecht, the Netherlands.

MARKER ASSISTED SELECTION refers to the process of selecting a desired trait or desired traits in a plant or plants by detecting one or more molecular markers from the plant, where the molecular marker is linked to the desired trait.

The term PHYSICALLY LINKED is used to indicate that two loci, e.g., two marker loci, are physically present on the same chromosome. Advantageously, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

The term PLANT includes reference to an immature or mature whole plant, including a plant from which seed or grain or anthers have been removed. Seed or embryo that will produce the plant is also considered to be the plant.

PLANT PARTS include leaves, stems, buds, roots, root tips, anthers, seed, grain, embryo, pollen, ovules, flowers, cotyledons, hypocotyls, pods, flowers, shoots and stalks, tissues, cells and the like.

POLYMORPHISM means a change or difference between two related nucleic acids. A "NUCLEOTIDE POLYMORPHISM" refers to a nucleotide that is different in one sequence when compared to a related sequence when the two nucleic acids are aligned for maximal correspondence. A "GENETIC NUCLEOTIDE POLYMORPHISM" refers to a nucleotide that is different in one sequence when compared to a related sequence when the two nucleic acids are aligned for maximal correspondence, where the two nucleic acids are genetically related, i.e., homologous, for example, where the nucleic acids are isolated from different strains of a soybean plant, or from different alleles of a single strain, or the like.

PROBE means a polynucleotide designed to be sufficiently complementary to a sequence in a denatured nucleic acid to be probed and to be bound under selected stringency conditions.

RAPD marker means random amplified polymorphic DNA marker. Chance pairs of sites complementary to single octa- or decanucleotides may exist in the correct orientation and close enough to one another for PCR amplification. With some randomly chosen decanucleotides no sequences are amplified. With others, the same length products are generated from DNAs of different individuals. With still others, patterns of bands are not the same for every individual in a population. The variable bands are commonly called random amplified polymorphic DNA (RAPD) bands.

RECOMBINATION FREQUENCY is the frequency of a crossing over event (recombination) between two genetic loci. Recombination frequency can be observed by following the segregation of markers and/or traits during meiosis. A marker locus is "associated with" another marker locus or some other locus (for example, a tolerance locus), when the relevant loci are part of the same linkage group and are in linkage disequilibrium. This occurs when the marker locus and a linked locus are found together in progeny plants more frequently than if the two loci segregate randomly. Similarly, a marker locus can also be associated with a trait, e.g., a marker locus can be "associated with tolerance or improved tolerance" when the marker locus is in linkage disequilibrium with the trait.

RFLP means restriction fragment length polymorphism. Molecular markers that occur because any sequence change in DNA, including a single base change, insertion, deletion or inversion, can result in loss or gain of a restriction endonuclease recognition site. The size and number of fragments generated by one such enzyme is therefore altered. A probe that hybridizes specifically to DNA in the region of such an alteration can be used to rapidly and specifically identify a region of DNA that displays allelic variation between two plant varieties. Isozyme Electrophoresis and RFLPs have been widely used to determine genetic composition SELF CROSSING or SELF-POLLINATION or SELFING is a process through which a breeder crosses hybrid progeny with itself; for example, a second generation hybrid F2 with itself to yield progeny designated F2:3.

SNP means single nucleotide polymorphism. SNPs are genetic markers in which DNA sequence variations that occur when a single nucleotide (A, T, C, or G) in the genome sequence is altered are mapped to sites on the soybean genome. Many techniques for detecting SNPs are known in the art, including allele specific hybridization, primer extension, and direct sequencing.

SSR means short sequence repeats. SSRs are genetic markers based on polymorphisms in repeated nucleotide sequences, such as microsatellites. A marker system based on SSRs can be highly informative in linkage analysis relative to other marker systems in that multiple alleles may be present. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

TOLERANT and TOLERANCE refer to plants in which higher doses of a herbicide are required to produce effects similar to those seen in non-tolerant plants. Tolerant plants typically exhibit fewer necrotic, lytic, chlorotic, or other lesions when subjected to the herbicide at concentrations and rates typically employed by the agricultural community.

TRANSGENIC PLANT refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. TRANSGENIC is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

TRAP marker means target region amplification polymorphism marker. The TRAP technique employs one fixed primer of known sequence in combination with a random primer to amplify genomic fragments. The differences in fragments between alleles can be detected by gel electrophoresis.

The term VECTOR is used in reference to polynucleotide or other molecules that transfer nucleic acid segment(s) into a cell. The term "vehicle" is sometimes used interchangeably with "vector." A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term YIELD refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

An equivalent position in a polynucleotide and/or polypeptide sequence is a position that correlates a position in the reference sequence when the sequences are aligned for a maximum correspondence. In some examples the sequences are aligned across their whole length using a global alignment program. In other examples, a portion of the sequence or sequences may be aligned using a local alignment program or a global alignment program, for example a sequence may comprise exons and introns, conserved motifs or domains, or functional motifs or domains which may be aligned to the reference sequence(s) to identify equivalent positions. Equivalent positions in polynucleotides encoding a polypeptide can be determined using the encoded amino acid, and/or using a FrameAlign program to align the polynucleotide and polypeptide for maximal correspondence.

The term "homologous" refers to nucleic acid sequences that are derived from a common ancestral gene through natural or artificial processes (e.g., are members of the same gene family), and thus, typically share sequence similarity. Typically, homologous nucleic acids have sufficient sequence identity that one of the sequences or a subsequence thereof or its complement is able to selectively hybridize to the other under selective (e.g., stringent) hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing nucleic acid sequences typically have about at least 70% sequence identity, at least 80% sequence identity, or about 90%, 91%, 92%, 93%, 94%, 95%, 96%, 97%, 98%, 99%, 99.5%, 99.75%, or 100% sequence identity with each other. A nucleic acid that exhibits at least some degree of homology to a reference nucleic acid can be unique or identical to the reference nucleic acid or its complementary sequence.

The term "isolated" refers to material, such as polynucleotides or polypeptides, which are identified and separated from at least one contaminant with which it is ordinarily associated in its natural or original source. Furthermore, an isolated polynucleotide or polypeptide is typically present in a form or setting that is different from the form or setting that is normally found in nature. In some examples, the isolated molecule is substantially free from components that normally accompany or interact with it in its naturally occurring environment. In some embodiments, the isolated material optionally comprises material not found with the material in its natural environment, e.g., in a cell.

As used herein, the terms "exogenous" or "heterologous" as applied to polynucleotides or polypeptides refers to molecules that have been artificially supplied to a biological system (e.g., a plant cell, a plant gene, a particular plant species or a plant chromosome under study) and are not native to that particular biological system. The terms indicate that the relevant material originated from a source other than the naturally occurring source, or refers to molecules having a non-natural configuration, genetic location or arrangement of parts. A heterologous polynucleotide includes polynucleotides from another organism or the same organism which have been modified by linkage to a distinct non-endogenous polynucleotide and/or inserted to a distinct non-endogenous locus. The terms "exogenous" and "heterologous" are sometimes used interchangeably with "recombinant."

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term "recombinant" indicates that the material (e.g., a recombinant nucleic acid, gene, polynucleotide or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural text and cloned into any type of artificial nucleic acid vector. Protocols and reagents to produce recombinant molecules, especially recombinant nucleic acids, are common and routine in the art (see, e.g., Maniatis et al. (eds.), Molecular Cloning: A Laboratory Manual, Cold Spring Harbor Laboratory Press, NY, [1982]; Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons, Inc., New York [1994]). The term recombinant can also refer to an organism that harbors a recombinant material, e.g., a plant that comprises a recombinant nucleic acid is considered a recombinant plant. In some embodiments, a recombinant organism is a transgenic organism.

The term "introduced" when referring to a heterologous or exogenous nucleic acid refers to the incorporation of a nucleic acid into a eukaryotic or prokaryotic cell using any type of suitable vector, e.g., naked linear DNA, plasmid, plastid or virion), converted into an autonomous replicon, or transiently expressed (e.g., transfected mRNA). The term includes such nucleic acid introduction means as "transfection," "transformation" and "transduction."

The term "host cell" means a cell that contains a heterologous nucleic acid, such as a vector, and supports the replication and/or expression of the nucleic acid. Host cells may be prokaryotic cells such as E. coli, or eukaryotic cells such as yeast, insect, amphibian or mammalian cells. In some examples, host cells are plant cells, including but not limited to dicot and monocot cells.

The term "transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

Plant cell, as used herein includes, without limitation, cells within or derived from, for example and without limitation, plant seeds, plant tissue suspension cultures, plant tissue, plant tissue explants, plant embryos, meristematic tissue, callus tissue, leaves, roots, shoots, gametophytes, sporophytes, pollen and microspores.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

The term "introgression" refers to the transmission of a desired allele of a genetic locus from one genetic background to another. For example, introgression of a desired allele at a specified locus can be transmitted to at least one progeny plant via a sexual cross between two parent plants, at least one of the parent plants having the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a gene allele that imparts resistance to a plant pathogen.

Protoporphyrinogen Oxidase Inhibitors

Porphyrins are biologically important organic structures that are found in plants attached to chlorophyll and cytochrome pigments. An intermediate in the chlorophyll and cytochrome synthesis pathway is protoporphyrinogen IX which is converted to protoporphyrin IX by protoporphyrinogen oxidase. Inhibition of protoporphyrinogen oxidase prevents this conversion and results in a buildup of protoporphyrinogen IX in the cytoplasm of the plant. The protoporphyrinogen then undergoes non-enzymatic auto-oxidation and becomes protoporphyrin IX. When cytoplasmic protoporphyrin IX is exposed to sunlight, free radicals are formed which results in lipid peroxidation reactions that result in plant death. Protoporphyrinogen oxidase inhibitor chemical families include diphenyl ether, triazolinone, N-phenylphthalimide, pyrimidindione and oxadiazole families. There are other families of chemistries that also belong to this group.

The diphenyl ether family is characterized by two benzene rings linked with an ether bridge and a nitro group bonded to the 4 position. Examples of diphenyl ether protoporphyrinogen oxidase inhibitors include acifluorfen, fomesafen, oxyfluorfen and lactofen. The diphenyl ethers are typically considered to be contact herbicides.

The triazolinone family is characterized by a 5-member ring containing three nitrogen atoms (two of which are adjacent) and two carbon atoms, one of the carbon atoms has a double bond with an oxygen atom and one of the nitrogen atoms is bonded to a benzene ring. Examples of triazolinone protoprophyrinogen oxidase inhibitors include sulfentrazone, carfentrasone, and azafeniden.

The N-phenylphthalimide family is characterized by pthalimide group wherein the nitrogen is bonded to a benzene ring. Examples of N-phenylphthalimide protoporphyrinogen oxidase inhibitors include flumiclorac and flumioxazin.

The oxadiazole family is characterized by a five member ring consisting of two adjacent nitrogen atoms, two carbon atoms, and an oxygen or sulfur atom. Examples of oxadiazole protoporphyrinogen oxidase inhibitors include oxadiazon and fluthiacet.

The various families of protoporphyrinogen oxidase inhibitors provide a wide variety in application options. Sulfentrazone, for example, has a relatively long half-life (approximately 280 days), is known to have residual soil activity and is frequently used as a pre-emergence herbicide. Carfentrazone has a considerably shorter half-life (approximately 4 days) has no residual soil activity, and is used as a contact/post-emergence herbicide. The pyrimidindiones family of PPO herbicides is a rather small class that includes benzfendizone, butagenacil and saflufenacil. This diversity in chemical characteristics combined with protoporphyrinogen oxidase inhibitor tolerance provides farmers with a wide variety of weed management options.

Molecular Markers and Genetic Linkage

Molecular markers have been used to selectively improve soybean crops through the use of marker assisted selection. Any detectable polymorphic trait can be used as a marker so long as it is inherited differentially and exhibits linkage disequilibrium with a phenotypic trait of interest. A number of soybean markers have been mapped and linkage groups created, as described in Cregan, P. B. et al., "An Integrated Genetic Linkage Map of the Soybean Genome" (1999) Crop Science 39:1464-90, and more recently in Choi et al., "A Soybean Transcript Map: Gene Distribution, Haplotype and Single-Nucleotide Polymorphism Analysis" (2007) Genetics 176:685-96. Many soybean markers are publicly available at the USDA affiliated soybase website.

Most plant traits of agronomic importance are polygenic, otherwise known as quantitative, traits. A quantitative trait is controlled by several genes located at various locations, or loci, in the plant's genome. The multiple genes have a cumulative effect which contributes to the continuous range of phenotypes observed in many plant traits. These genes are referred to as quantitative trait loci (QTL). Recombination frequency measures the extent to which a molecular marker is linked with a QTL. Lower recombination frequencies, typically measured in centiMorgans (cM), indicates greater the linkage between the QTL and the molecular marker. The extent to which two features are linked is often referred to as the genetic distance. The genetic distance is also typically related to the physical distance between the marker and the QTL, however, certain biological phenomenon (including recombinational "hot spots") can affect the relationship between physical distance and genetic distance. Generally, the usefulness of a molecular marker is determined by the genetic and physical distance between the marker and the selectable trait of interest.

The method for determining the presence or absence of a QTL associated with tolerance to protoporphyrinogen oxidase inhibitors in soybean germplasm, comprises analyzing genomic DNA from a soybean germplasm for the presence of at least one molecular marker, wherein at least one molecular marker is linked to the QTL, and wherein the QTL maps to soybean major linkage group L and N and is associated with tolerance to protoporphyrinogen oxidase inhibitors. The term "is associated with" in this context means that the QTL associated with tolerance to protoporphyrinogen oxidase inhibitors has been found, using marker-assisted analysis, to be present in soybean plants showing tolerance to protoporphyrinogen oxidase inhibitors in live bioassays as described herein.

Generally, markers that map closer to the QTL mapped to linkage group L and N and associated with tolerance to protoporphyrinogen oxidase inhibitors are superior to markers that map farther from the QTL. In some examples a marker used to determine the presence or absence of a QTL mapping to soybean linkage group L and/or N and associated with tolerance to protoporphyrinogen oxidase inhibitors maps to soybean linkage group L are SATT495, P10649C-3, SATT182, SATT388, SATT313, SATT613 (or other markers above marker SATT613), S08102-1-Q1, S08103-1-Q1. S08104-1-Q1, S08106-1-Q1, S08107-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, and S08101-3-Q1, and those mapped to linkage group N are Sat_379, SCT_195, SATT631, S60167-TB, SATT675, SATT624, SATT080, and SATT387 (or other markers above SATT387). Any marker assigned to soybean linkage group L and/or N and linked to a marker disclosed herein as associated with tolerance to protoporphyrinogen oxidase inhibitors may be used with the invention. Generally, a linked marker is within 50 cM of the referenced marker. Updated information regarding markers assigned to soybean linkage group L and N may be found on the USDA's Soybase website. Further, linkage group L is now formally referred to as chromosome #19 and linkage group N is now formally referred to as chromosome #3.

Markers flanking the QTL associated with tolerance to protoporphyrinogen oxidase inhibitors are used in the marker-assisted selection processes provided. The genomic DNA of soybean germplasm is typically tested for the presence of at least two of the foregoing molecular markers, one marker on each side of the QTL. In some examples a QTL on linkage group L is used. Useful markers on linkage group L include SATT495, P10649C-3, SATT182, SATT388, SATT313, and SATT613, including markers above SATT613. Markers that map close to SATT495, P10649C-3, SATT182, SATT388, SATT313, and SATT613 can also be used. In some examples a QTL on linkage group N is used. Useful markers on linkage group N include Sat_379, SCT_195, SATT631, S60167-TB, SATT675, SATT624, SATT080, and SATT387, including markers above SATT387. Markers that map close to Sat_379, SCT_195, SATT631, S60167-TB, SATT675, SATT624, SATT080, and SATT387 can also be used.

Fine mapping further isolated the location of the QTL to a 56 kb interval between marker S08117-1-Q1 and S08105-1-Q1 on linkage group L. Accordingly, markers that map within the interval defined by and including these markers are particularly useful for selecting for this QTL. These markers include S08117-1-Q1, S08119-1-Q1, S08118-1-Q1, S08116-1-Q1, S08112-1-Q1, S08108-1-Q1, S08101-1-Q1, S08101-2-Q1, S08101-3-Q1, S08101-4-Q1, and S08105-4-Q1.

Methods of introgressing protoporphyrinogen oxidase inhibitor tolerance into non-tolerant or less-tolerant soybean germplasm are provided. Any method for introgressing QTLs into soybean plants can be used. In some examples, a first soybean germplasm that contains tolerance to protoporphyrinogen oxidase inhibitors derived from the QTL mapped to linkage group L and/or N which is associated with tolerance to protoporphyrinogen oxidase inhibitors and a second soybean germplasm that lacks tolerance to protoporphyrinogen oxidase inhibitors derived from the QTL mapped to linkage group L and/or N are provided. The first soybean plant may be crossed with the second soybean plant to provide progeny soybeans. Phenotypic and/or marker screening is then performed on the progeny plants to determine the presence of tolerance to protoporphyrinogen oxidase inhibitors derived from the QTL mapped to linkage group L and/or N. Progeny that test positive for the presence of tolerance to protoporphyrinogen oxidase inhibitors derived from the QTL mapped to linkage group L and/or N can be selected.

In some examples, the screening and selection are performed by using marker-assisted selection using any marker or combination of markers on major linkage group L and/or N provided. Any method of identifying the presence or absence of these markers may be used, including for example single-strand conformation polymorphism (SSCP) analysis, base excision sequence scanning (BESS), RFLP analysis, heteroduplex analysis, denaturing gradient gel electrophoresis, and temperature gradient electrophoresis, allelic PCR, ligase chain reaction direct sequencing, mini sequencing, nucleic acid hybridization, or micro-array-type detection.

Systems, including automated systems for selecting plants that comprise a marker of interest and/or for correlating presence of the marker with tolerance are also provided. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

Kits are also provided. For example, a kit can include appropriate primers or probes for detecting tolerance associated marker loci and instructions in using the primers or probes for detecting the marker loci and correlating the loci with predicted protoporphyrinogen oxidase inhibitor tolerance. The kits can further include packaging materials for packaging the probes, primers or instructions, controls such as control amplification reactions that include probes, primers or template nucleic acids for amplifications, molecular size markers, or the like.

Isolated nucleic acid fragments comprising a nucleic acid sequence coding for soybean tolerance to protoporphyrinogen oxidase inhibitors, are provided. The nucleic acid fragment comprises at least a portion of nucleic acid belonging to linkage group L and/or N. The nucleic acid fragment is capable of hybridizing under stringent conditions to nucleic acid of a soybean cultivar tolerant to protoporphyrinogen oxidase inhibitors containing a QTL associated with protoporphyrinogen oxidase inhibitor tolerance that is located on major linkage group L and/or N.

Vectors comprising such nucleic acid fragments, expression products of such vectors expressed in a host compatible therewith, antibodies to the expression product (both polyclonal and monoclonal), and antisense nucleic acid to the nucleic acid fragment are also provided.

Seed of a soybean produced by crossing a soybean variety having protoporphyrinogen oxidase inhibitor tolerance QTL located on major linkage group L and/or N in its genome with another soybean variety, and progeny thereof, are provided.
Tolerance Markers and Favorable Alleles In traditional linkage analysis, no direct knowledge of the physical relationship of genes on a chromosome is required. Mendel's first law is that factors of pairs of characteristics are segregated, meaning that alleles of a diploid trait separate into two gametes and then into different offspring. Classical linkage analysis can be thought of as a statistical description of the relative frequencies of cosegregation of different traits. Linkage analysis, as described previously, is the well-characterized descriptive framework of how traits are grouped together based upon the frequency with which they segregate together. Because chromosomal distance is approximately proportional to the frequency of crossing over events between traits, there is an approximate physical distance that correlates with recombination frequency.

Marker loci are traits, and can be assessed according to standard linkage analysis by tracking the marker loci during segregation. Thus, one cM is equal to a 1% chance that a marker locus will be separated from another locus (which can be any other trait, e.g., another marker locus, or another trait locus that encodes a QTL), due to crossing over in a single generation. The markers herein, e.g., for linkage group L: SATT495, P10649C-3, SATT182, SATT388, SATT313, SATT613 (and other markers above SATT613), S08102-1-Q1, S08103-1-Q1. S08104-1-Q1, S08106-1-Q1, S08107-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, and S08101-3-Q1, and for linkage group N: Sat_379, SCT_195, SATT631, S60167-TB, SATT675, SATT624, SATT080, and SATT387 (and other markers above SATT387), have been found to correlate with tolerance or improved tolerance to protoporphyrinogen oxidase inhibitors in soybean. This means that the markers are sufficiently proximal to a tolerance trait that they can be used as a predictor for the tolerance trait itself, using, for example, marker assisted selection (MAS). Soybean plants or germplasm can be selected for markers or marker alleles that positively correlate with tolerance, without actually raising soybean and measuring for tolerance or improved tolerance (or, contrawise, soybean plants can be selected against if they possess markers that negatively correlate with tolerance or improved tolerance. MAS is a powerful shortcut to selecting for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

Any marker that is linked to a trait of interest (e.g., in the present case, a tolerance or improved tolerance trait) can be used as a marker for that trait. Thus, in addition to the markers described herein, markers linked to the markers itemized herein can also be used to predict the tolerance or improved tolerance trait. Such linked markers are particularly useful when they are sufficiently proximal to a given marker so that they display a low recombination frequency with the given marker. Markers closely linked to the markers on linkage group L and/or linkage group N are also provided. Closely linked markers display a cross over frequency with a given marker of about 10% or less (the given marker is within 10cM of the given marker). Put another way, closely linked loci co-segregate at least 90% of the time.

Marker loci are especially useful when they are closely linked to target loci (e.g., QTL for tolerance, or, alternatively, simply other marker loci, such as those identified herein, that are linked to such QTL) for which they are being used as markers. A marker more closely linked to a target locus is a better indicator for the target locus (due to the reduced cross-over frequency between the target locus and the marker). Thus, in one example, closely linked loci such as a marker locus and a second locus (e.g., a given marker or a QTL) display an inter-locus cross-over frequency of about 10% or less, about 9% or less, about 8% or less, about 7% or less, about 6% or less, about 5% or less, about 4% or less, about 3% or less, or about 2% or less. In some examples, the relevant loci (e.g., a marker locus and a target locus such as a QTL) display a recombination a frequency of about 1% or less, e.g., about 0.75% or less, about 0.5% or less, or about 0.25% or less. Thus, the loci are about 10 cM, 9 cM, 8 cM, 7 cM, 6 cM, 5 cM, 4 cM, 3 cM, 2cM, 1cM, 0.75 cM, 0.5 cM or 0.25 cM or less apart. Put another way, two loci that are localized to the same chromosome, and at such a distance that recombination between the two loci occurs at a frequency of no more than 10% (e.g., about 9%, 8%, 7%, 6%, 5%, 4%, 3%, 2%, 1%, 0.75%, 0.5%, 0.25%, or less) are said to be proximal to each other.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

Optionally, one, two, three or more favorable allele(s) are identified in, or introgressed into the plant. Many marker alleles can be selected for or against during MAS. Plants or germplasm are identified that have at least one such favorable allele that positively correlates with tolerance or improved tolerance. However, it is useful for exclusionary purposes during breeding to identify alleles that negatively correlate with tolerance, to eliminate such plants or germplasm from subsequent rounds of breeding.

The identification of favorable marker alleles is germplasm-specific. The determination of which marker alleles correlate with tolerance (or non-tolerance) is determined for the particular germplasm under study. One of skill recognizes that methods for identifying the favorable alleles are routine and well known, and furthermore, that the identification and use of such favorable alleles is well within the scope of the invention.

Amplification primers for amplifying marker loci and suitable marker probes to detect marker loci or to genotype SNP alleles are provided. Optionally, other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. The configuration of the amplification primers and detection probes can, of course, vary. Thus, the invention is not limited to the primers and probes specifically recited herein.

In some examples the presence of marker loci is directly detected in unamplified genomic DNA by performing a Southern blot on a sample of genomic DNA using probes to the marker loci. Procedures for performing Southern blotting, amplification (PCR, LCR, or the like) and many other nucleic acid detection methods are well established and are taught, e.g., in Sambrook et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. While the exemplary markers provided in the tables herein are either SSR or SNP (ASH) markers, any of the aforementioned marker types can be employed to identify chromosome segments encompassing genetic element that contribute to superior agronomic performance (e.g., tolerance or improved tolerance).

In another example, the presence or absence of a molecular marker is determined by nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York, as well as in Sambrook, and Ausubel.

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each cross is a simple procedure. After separation by length in an appropriate matrix (e.g., agarose, polyacrylamide, etc.) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Methods and reagents for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

Amplification-Based Detection Methods

PCR, RT-PCR and LCR are in particularly broad use as amplification and amplification-detection methods for amplifying nucleic acids of interest (e.g., those comprising marker loci), facilitating detection of the markers. Details regarding the use of these and other amplification methods can be found in any of a variety of standard texts, including, e.g., Sambrook, Ausubel, Berger and Croy, supra. Many available biology texts also have extended discussions regarding PCR and related amplification methods. Any RNA can be converted into a double stranded DNA suitable for restriction digestion, PCR expansion and sequencing using reverse transcriptase and a polymerase ("Reverse Transcription-PCR, or "RT-PCR"). See also Ausubel and Sambrook, supra.

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or peptide nucleic acid (PNA) which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched and signal is detected. Standard methods of making and using MBs are known and MBs and reagents are commercially available. See also, e.g., Leone et al. (1995) "Molecular beacon probes combined with amplification by NASBA enable homogenous real-time detection of RNA." Nucleic Acids Res. 26:2150-2155; Tyagi and Kramer (1996) "Molecular beacons: probes that fluoresce upon hybridization" Nature Biotechnology 14:303-308; Blok and Kramer (1997) "Amplifiable hybridization probes containing a molecular switch" Mol Cell Probes 11:187-194; Hsuih et al. (1997) "Novel, ligation-dependent PCR assay for detection of hepatitis C in serum" J Clin Microbiol 34:501-507; Kostrikis et al. (1998) "Molecular beacons: spectral genotyping of human alleles" Science 279:1228-1229; Sokol et al. (1998) "Real time detection of DNA:RNA hybridization in living cells" Proc. Natl. Acad. Sci. U.S.A. 95:11538-11543; Tyagi et al. (1998) "Multicolor molecular beacons for allele discrimination" Nature Biotechnology 16:49-53; Bonnet et al. (1999) "Thermodynamic basis of the chemical specificity of structured DNA probes" Proc. Natl. Acad. Sci. U.S.A. 96:6171-6176; Fang et al. (1999) "Designing a novel molecular beacon for surface-immobilized DNA hybridization studies" J. Am. Chem. Soc. 121:2921-2922; Marras et al. (1999) "Multiplex detection of single-nucleotide variation using molecular beacons" Genet. Anal. Biomol. Eng. 14:151-156; and Vet et al. (1999) "Multiplex detection of four pathogenic retroviruses using molecular beacons" Proc. Natl. Acad. Sci. U.S.A. 96:6394-6399. See also, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al. (Nov. 21, 2000) entitled "Nucleic acid detection probes having non-FRET fluorescence quenching and kits and assays including such probes" and U.S. Pat. No. 6,037,130 to Tyagi et al. (Mar. 14, 2000), entitled "Wavelength-shifting probes and primers and their use in assays and kits."

PCR detection and quantification using dual-labeled fluorogenic oligonucleotide probes can be done, using for example TaqMan® probes. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan® probes are oligonucleotides that have a label and a quencher, where the label is released during amplification by the exonuclease action of the polymerase used in amplification. This provides a real time measure of amplification during synthesis. A variety of TaqMan® reagents are commercially available, e.g., from Applied Biosystems (Division Headquarters in Foster City, Calif.) as well as from a variety of specialty vendors such as Biosearch Technologies (e.g., black hole quencher probes).

Additional Details Regarding Amplified Variable Sequences, SSR, AFLP ASH, SNPs and Isozyme Markers Amplified variable sequences refer to amplified sequences of the plant genome, which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Typically, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) Proc Natl Acad Sci USA 87:1874). By mimicking the retroviral strategy of RNA replication by means of cDNA intermediates, this reaction accumulates cDNA and RNA copies of the original target.

Amplified fragment length polymophisms (AFLP) can also be used as genetic markers (Vos et al. (1995) Nucl Acids Res 23:4407). The phrase "amplified fragment length polymorphism" refers to selected restriction fragments, which are amplified before or after cleavage by a restriction endonuclease. The amplification step allows easier detection of specific restriction fragments. AFLP allows the detection large numbers of polymorphic markers and has been used for genetic mapping of plants (Becker et al. (1995) Mol Gen Genet. 249:65; and Meksem et al. (1995) Mol Gen Genet. 249:74).

Allele-specific hybridization (ASH) can be used to identify the genetic markers. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane. In one example, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on, e.g., an acrylamide gel. However, alternative modes of detection, such as hybridization, e.g., ASH, or RFLP analysis are also appropriate.

Isozyme markers can be employed as genetic markers, e.g., to track markers other than the tolerance markers herein, or to track isozyme markers linked to the markers herein. Isozymes are multiple forms of enzymes that differ from one another in their amino acid sequence, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes, which differ at the nucleic acid level, can be determined. In such cases any of the nucleic acid based methods described herein can be used to analyze isozyme markers.

Probe/Primer Synthesis Methods

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981) Tetrahedron Letts 22:1859-1862, e.g., using a commercially available automated synthesizer, e.g., as described in Needham-VanDevanter et al. (1984) Nucleic Acids Res. 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company (mcrc@oligos.com), The Great American Gene Company (genco.com), ExpressGen Inc. (expressgen.com), Operon Technologies Inc. (Alameda, Calif.) and many others. Similarly, PNAs can be custom ordered from any of a variety of sources, such as PeptidoGenic (pkim@ccnet.com), HTI Bio-products, inc. (htibio.com), BMA Biomedicals Ltd (U.K.), Bio. Synthesis, Inc., and many others.

In Silico Marker Detection

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Amplification Primers for Marker Detection

In some examples, molecular markers are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. Suitable primers can be designed using any suitable method. It is not intended that the invention be limited to any particular primer or primer pair. For example, primers can be designed using any suitable software program, such as LASERGENE®.

In some examples, the primers are radiolabelled, or labeled by any suitable means (e.g., using a non-radioactive fluorescent tag), to allow for rapid visualization of the different size amplicons following an amplification reaction without any additional labeling step or visualization step. In some examples, the primers are not labeled, and the amplicons are visualized following their size resolution, e.g., following agarose gel electrophoresis. In some examples, ethidium bromide staining of the PCR amplicons following size resolution allows visualization of the different size amplicons.

The primers used to amplify the marker loci and alleles herein are not limited to amplifying the entire region of the relevant locus. In some examples, marker amplification produces an amplicon at least 20 nucleotides in length, or alternatively, at least 50 nucleotides in length, or alternatively, at least 100 nucleotides in length, or alternatively, at least 200 nucleotides in length, or up to and including the full length of the amplicon.

Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants that contain a desired genotype at one locus, or at several unlinked or linked loci (e.g., a haplotype), and that would be expected to transfer the desired genotype, along with a desired phenotype to their progeny. Means to identify plants, particularly soybean plants, that are tolerant, or that exhibit improved tolerance to protoporphyrinogen oxidase inhibitors are provided, for example by identifying plants having a specified marker loci e.g., for linkage group L: SATT495, P10649C-3, SATT182, SATT388, SATT313, SATT613 (and other markers above SATT613), S08102-1-Q1, S08103-1-Q1. S08104-1-Q1, S08106-1-Q1, S08107-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, and S08101-3-Q1, and/or for linkage group N: Sat_379, SCT_195, SATT631, S60167-TB, SATT675, SATT624, SATT080, and SATT387 (and other markers above SATT387). Similarly, by identifying plants lacking the desired marker locus, non-tolerant or less tolerant plants can be identified, and, e.g., eliminated from subsequent crosses. Similarly, these marker loci can be introgressed into any desired genomic background, germplasm, plant, line, variety, etc., as part of an overall MAS breeding program designed to enhance soybean yield.

In general, the application of MAS uses the identification of a population of tolerant plants and genetic mapping of the tolerance trait. Polymorphic loci in the vicinity of the mapped tolerance trait are chosen as potential tolerance markers. Typically, a marker locus closest to the tolerance locus is a preferred marker. Linkage analysis is then used to determine which polymorphic marker allele sequence demonstrates a statistical likelihood of co-segregation with the tolerant phenotype (thus, a "tolerance marker allele"). Following identification of a marker allele for co-segregation with the tolerance allele, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is anonymous. Tissue samples can be taken, for example, from the first leaf of the plant and screened with the appropriate molecular marker, and within days it is determined which progeny will advance. Linked markers also remove the impact of environmental factors that can often influence phenotypic expression.

After a desired phenotype (e.g., tolerance to protoporphyrinogen oxidase inhibitors) and a polymorphic chromosomal marker locus are determined to cosegregate, the polymorphic marker locus can be used to select for marker alleles that segregate with the desired tolerance phenotype. This general process is typically called marker-assisted selection (MAS). In brief, a nucleic acid corresponding to the marker nucleic acid is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. After the presence (or absence) of a particular marker in the biological sample is verified, the plant is selected, e.g., used to make progeny plants by selective breeding.

Soybean plant breeders desire combinations of tolerance loci with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein genetically linked to tolerance loci provide effective methods for selecting tolerant varieties in breeding programs. For example, one advantage of marker-assisted selection over field evaluations for tolerance is that MAS can be done at any time of year, regardless of the growing season. Moreover, environmental effects are largely irrelevant to marker-assisted selection.

When a population is segregating for multiple loci affecting one or multiple traits, e.g., multiple loci involved in tolerance, or multiple loci each involved in tolerance or tolerance to different herbicides, the efficiency of MAS compared to phenotypic screening becomes even greater, because all of the loci can be evaluated in the lab together from a single sample of DNA. In the present instance, for linkage group L: SATT495, P10649C-3, SATT182, SATT388, SATT313, SATT613 (or other markers above SATT613), S08102-1-Q1, S08103-1-Q1. S08104-1-Q1, S08106-1-Q1, S08107-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, and S08101-3-Q1; and for linkage group N: Sat_379, SCT_195, SATT631, S60167-TB, SATT675, SATT624, SATT080, and SATT387 (or other markers above SATT387) markers, and markers for other traits, transgenes, and/or loci can be assayed simultaneously or sequentially in a single sample or population of samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding soybean line). The more cycles of backcrossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait such as tolerance to protoporphyrinogen oxidase inhibitors.

The presence and/or absence of a particular genetic marker or allele, e.g., for linkage group L: SATT495, P10649C-3, SATT182, SATT388, SATT313, SATT613 (including markers above SATT613), S08102-1-Q1, S08103-1-Q1. S08104-1-Q1, S08106-1-Q1, S08107-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, and S08101-3-Q1, and for linkage group N: Sat_379, SCT_195, SATT631, S60167-TB, SATT675, SATT624, SATT080, and SATT387 (including markers above SATT387) in the genome of a plant exhibiting a preferred phenotypic trait is made by any method noted herein. If the nucleic acids from the plant are positive for a desired genetic marker, the plant can be self fertilized to create a true breeding line with the same genotype, or it can be crossed with a plant with the same marker or with other desired characteristics to create a sexually crossed hybrid generation.

Introgression of Favorable Alleles—Efficient Crossing of Tolerance Markers into Other Lines One application of MAS is to use the tolerance or improved tolerance markers to increase the efficiency of an introgression or backcrossing effort aimed at introducing a tolerance QTL into a desired (typically high yielding) background. In marker assisted backcrossing of specific markers (and associated QTL) from a donor source, e.g., to an elite genetic background, one selects among progeny or backcross progeny for the donor trait.

Thus, the markers and methods can be utilized to guide marker assisted selection or breeding of soybean varieties with the desired complement (set) of allelic forms of chromosome segments associated with herbicide tolerance as well as markers associated with superior agronomic performance (tolerance, along with any other available markers for yield, disease tolerance, etc.). Any of the disclosed marker alleles can be introduced into a soybean line via introgression, by traditional breeding (or introduced via transformation, or both) to yield a soybean plant with superior agronomic performance. The number of alleles associated with tolerance that can be introduced or be present in a soybean plant ranges from 1 to the number of alleles disclosed herein, each integer of which is incorporated herein as if explicitly recited.

Methods of making a progeny soybean plant and these progeny soybean plants having tolerance to PPO inhibitors are provided. These methods comprise crossing a first parent soybean plant with a second soybean plant and growing the female soybean plant under plant growth conditions to yield soybean plant progeny. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant comprising at least one of the allelic forms of the markers provided, such that the progeny are capable of inheriting the allele.

Inheritance of the desired tolerance allele can be traced, such as from progenitor or descendant lines in the subject soybean plants pedigree such that the number of generations separating the soybean plants being subject to the methods will generally be from 1 to 20, commonly 1 to 5, and typically 1, 2, or 3 generations of separation, and quite often a direct descendant or parent of the soybean plant will be subject to the method (i.e., 1 generation of separation).

Methods For Identifying Protoporphyrinogen Oxidase Inhibitor Tolerant Soybean Plants Experienced plant breeders can recognize tolerant soybean plants in the field, and can select the tolerant individuals or populations for breeding purposes or for propagation. In this context, the plant breeder recognizes tolerant, and non-tolerant soybean plants.

The screening and selection may also be performed by exposing plants containing said progeny germplasm to protoporphyrinogen oxidase inhibitors in an assay and selecting those plants showing tolerance to protoporphyrinogen oxidase inhibitors as containing soybean germplasm into which germplasm having tolerance to protoporphyrinogen oxidase inhibitors derived from the QTL mapped to linkage group L and/or N has been introgressed. The live assay may be any such assay known to the art, e.g., Taylor-Lovell et al. (2001) Weed Tech 15:95-102.

However, plant tolerance is a phenotypic spectrum consisting of extremes of high tolerance to non-tolerance with a continuum of intermediate tolerance phenotypes. Evaluation of these intermediate phenotypes using reproducible assays are of value to scientists who seek to identify genetic loci that impart tolerance, conduct marker assisted selection for tolerant population, and for introgression techniques to breed a tolerance trait into an elite soybean line, for example. Describing the continuum of tolerance can be done using any known scoring system or derivative thereof, including the scoring systems described in Examples 1-4.

Automated Detection/Correlation Systems

In some examples, the methods include an automated system for detecting markers and or correlating the markers with a desired phenotype (e.g., tolerance). Thus, a typical system can include a set of marker probes or primers configured to detect at least one favorable allele of one or more marker locus associated with tolerance or improved tolerance to protoporphyrinogen oxidase inhibitors. These probes or primers are configured to detect the marker alleles noted in the tables and examples herein, e.g., using any available allele detection format, e.g., solid or liquid phase array based detection, microfluidic-based sample detection, etc.

In some examples markers involving linkage group L are used. In some examples a marker closely linked to the marker locus of SATT495, P10649C-3, SATT182, SATT388, SATT313, SATT613, S08102-1-Q1, S08103-1-Q1. S08104-1-Q1, S08106-1-Q1, S08107-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, and S08101-3-Q1 is used, and the probe set is configured to detect the closely linked marker(s). In some examples, the marker locus is SATT495, P10649C-3, SATT182, SATT388, SATT313, SATT613 (or another marker above SATT613), S08102-1-Q1, S08103-1-Q1. S08104-1-Q1, S08106-1-Q1, S08107-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, and S08101-3-Q1 and the probe set is configured to detect the locus. Similarly, alleles of SATT495, P10649C-3, SATT182, SATT388, SATT313, and SATT613 can be detected.

In some examples markers involving linkage group N are used. In some examples a marker closely linked to the marker locus of Sat_379, SCT_195, SATT631, S60167-TB, SATT675, SATT624, SATT080, and SATT387 (or another marker above SATT387) is used, and the probe set is configured to detect the closely linked marker(s). In some examples the marker locus is Sat_379, SCT_195, SATT631, S60167-

TB, SATT675, SATT624, SATT080, and SATT387 and the probe set is configured to detect the locus. Similarly, alleles of Sat_379, SCT_195, SATT631, S60167-TB, SATT675, SATT624, SATT080, and SATT387 can be detected.

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele. The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also provided. For example, the instructions can include at least one look-up table that includes a correlation between the presence or absence of the favorable alleles and the predicted tolerance or improved tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted tolerance or improved tolerance. The instructions also typically include instructions providing a user interface with the system, e.g., to permit a user to view results of a sample analysis and to input parameters into the system.

The system typically includes components for storing or transmitting computer readable data representing or designating the alleles detected by the methods, e.g., in an automated system. The computer readable media can include cache, main, and storage memory and/or other electronic data storage components (hard drives, floppy drives, storage drives, etc.) for storage of computer code. Data representing alleles detected by the methods can also be electronically, optically, magnetically o transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program," by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g., C/C++ programs for computing, Delphi and/or Java programs for GUI interfaces, and productivity tools (e.g., Microsoft Excel and/or SigmaPlot) for charting or creating look up tables of relevant allele-trait correlations. Other useful software tools in the context of the integrated systems include statistical packages such as SAS, Genstat, Matlab, Mathematica, and S-Plus and genetic modeling packages such as QU-GENE. Furthermore, additional programming languages such as visual basic are also suitably employed in the integrated systems.

For example, tolerance marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase) suitable for recording data in a computer readable medium is acceptable as a database. Data regarding genotype for one or more molecular markers, e.g., ASH, SSR, RFLP, RAPD, AFLP, SNP, isozyme markers or other markers as described herein, are similarly recorded in a computer accessible database. Optionally, marker data is obtained using an integrated system that automates one or more aspects of the assay (or assays) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like, for, e.g., selecting files, retrieving data, reviewing tables of maker information, etc., and an output device (e.g., a monitor, a printer, etc.) for viewing or recovering the product of the statistical analysis.

Integrated systems comprising a computer or computer readable medium comprising set of files and/or a database with at least one data set that corresponds to the marker alleles herein are provided. The systems optionally also includes a user interface allowing a user to selectively view one or more of these databases. In addition, standard text manipulation software such as word processing software (e.g., Microsoft Word™ or Corel Wordperfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent technologies (Palo Alto, Calif.).

Systems for molecular marker analysis can include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of soybean plants with favorable allelic forms of chromosome segments involved in agronomic performance (e.g., tolerance or improved tolerance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image.

Positional Cloning

The molecular marker loci and alleles associated with tolerance to PPO inhibitors, e.g., SATT495, P10649C-3, SATT182, S03859-1, S00224-1, SATT388, SATT313, and SATT613 (including markers above SATT613), S08102-1-Q1, S08103-1-Q1. S08104-1-Q1, S08106-1-Q1, S08107-1-Q1, S08107-2-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, or S08101-3-Q1 can be used, as indicated previously, to identify a tolerance QTL, which can be cloned by well-established procedures, e.g., as described in detail in Ausubel, Berger and Sambrook, herein.

These tolerance clones are first identified by their genetic linkage to markers provided herein. Isolation of a nucleic acid of interest is achieved by any number of methods as discussed in detail in such references as Ausubel, Berger and Sambrook, herein, and Clark, ed. (1997) Plant Molecular Biology: A Laboratory Manual Springer-Verlag, Berlin.

For example, "positional gene cloning" uses the proximity of a tolerance marker to physically define an isolated chromosomal fragment containing a tolerance QTL gene. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication, and, e.g., expression, of the inserted fragment. Markers that are adjacent to an open reading frame (ORF) associated with a phenotypic trait can hybridize to a DNA clone (e.g., a clone from a genomic DNA library), thereby identifying a clone on which an ORF (or a fragment of an ORF) is located. If the marker is more distant, a fragment containing the open reading frame is identified by successive rounds of screening and isolation of clones which together comprise a contiguous sequence of DNA, a process termed "chromosome walking", resulting in a "contig" or "contig map." Protocols sufficient to guide one of skill through the isolation of clones associated with linked markers are found in, e.g. Berger, Sambrook and Ausubel, all herein.

Variant sequences have a high degree of sequence similarity. For polynucleotides, conservative variants include those sequences that, because of the degeneracy of the genetic code, encode the amino acid sequence of one of the native recombinase polypeptides. Variants such as these can be identified with the use of well-known molecular biology techniques, as, for example, with polymerase chain reaction (PCR) and hybridization techniques. Variant polynucleotides also include synthetically derived nucleotide sequences, such as those generated, for example, by using site-directed mutagenesis but which still encode a recombinase protein. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by known sequence alignment programs and parameters.

Variants of a particular polynucleotide (the reference nucleotide sequence) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the recombinase are known. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A variant protein is intended a protein derived from the native protein by deletion, addition, and/or substitution of one or more amino acids to the N-terminal, internal region(s), and/or C-terminal end of the native protein. Variant proteins are biologically active, that is they continue to possess the desired biological activity of the native protein, for example a variant recombinase will implement a recombination event between appropriate recombination sites. Such variants may result from, for example, genetic polymorphism or from human manipulation. Biologically active variants of a native recombinase protein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by known sequence alignment programs and parameters. A biologically active variant of a protein may differ from that protein by as few as 1-15 amino acid residues, as few as 1-10, such as 6-10, as few as 5, as few as 4, 3, 2, or even 1 amino acid residue.

Sequence relationships can be analyzed and described using computer-implemented algorithms. The sequence relationship between two or more polynucleotides, or two or more polypeptides can be determined by generating the best alignment of the sequences, and scoring the matches and the gaps in the alignment, which yields the percent sequence identity, and the percent sequence similarity. Polynucleotide relationships can also be described based on a comparison of the polypeptides each encodes. Many programs and algorithms for the comparison and analysis of sequences are available.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff & Henikoff (1989) Proc Natl Acad Sci USA 89:10915).

GAP uses the algorithm of Needleman & Wunsch (1970) J Mol Biol 48:443-453, to find an alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. GAP presents one member of the family of best alignments.

Sequence identity, or identity, is a measure of the residues in the two sequences that are the same when aligned for maximum correspondence. Sequences, particularly polypeptides, that differ by conservative substitutions are said to have sequence similarity or similarity. Means for making this adjustment are known, and typically involve scoring a conservative substitution as a partial rather than a full mismatch. For example, where an identical amino acid is given a score of 1 and a non-conservative substitution is given a score of zero, a conservative substitution is given a score between zero and 1. The scoring of conservative substitutions is calculated using the selected scoring matrix (BLOSUM62 by default for GAP).

Proteins may be altered in various ways including amino acid substitutions, deletions, truncations, and insertions. Methods for such manipulations are generally known. For example, amino acid sequence variants of the recombinase proteins can be prepared by mutations in the DNA. Methods for mutagenesis and nucleotide sequence alterations include for example, Kunkel (1985) Proc Natl Acad Sci USA 82:488-492; Kunkel et al. (1987) Methods in Enzymol 154:367-382; U.S. Pat. No. 4,873,192; Walker & Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl Biomed Res Found, Washington, D.C.). Conservative substitutions, such as exchanging one amino acid with another having similar properties, may be preferable.

Generation of Transgenic Cells and Plants

The present invention also relates to host cells and organisms which are transformed with nucleic acids corresponding to tolerance QTL identified herein. For example, such nucleic acids include chromosome intervals (e.g., genomic fragments), ORFs and/or cDNAs that encode a tolerance or improved tolerance trait. Additionally, production of polypeptides that provide tolerance or improved tolerance by recombinant techniques are provided.

General texts which describe molecular biological techniques for the cloning and manipulation of nucleic acids and production of encoded polypeptides include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2001 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 2004 or later) ("Ausubel")). These texts describe mutagenesis, the use of vectors, promoters and many other relevant topics related to, e.g., the generation of clones that comprise nucleic acids of interest, e.g., marker loci, marker probes, QTL that segregate with marker loci, etc.

Host cells are genetically engineered (e.g., transduced, transfected, transformed, etc.) with the vectors (e.g., vectors, such as expression vectors which comprise an ORF derived from or related to a tolerance QTL) which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells or plant protoplasts by a variety of standard methods known in the art, including but not limited to electroporation (From et al. (1985) Proc. Natl. Acad. Sci. USA 82; 5824), infection by viral vectors such as cauliflower mosaic virus (CaMV) (Hohn et al. (1982) Molecular Biology of Plant Tumors (Academic Press, New York, pp. 549-560; Howell U.S. Pat. No. 4,407, 956), high velocity ballistic penetration by small particles with the nucleic acid either within the matrix of small beads or particles, or on the surface (Klein et al. (1987) Nature 327;

70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) Science 233; 496; Fraley et al. (1983) Proc. Natl. Acad. Sci. USA 80; 4803). Additional details regarding nucleic acid introduction methods are found in Sambrook, Berger and Ausubel, infra. The method of introducing a nucleic acid into a host cell is not critical, and therefore should not be limited to any particular method for introducing exogenous genetic material into a host cell. Thus, any suitable method, e.g., including but not limited to the methods provided herein, which provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, all infra. Plant regeneration from cultured protoplasts is described in Evans et al. (1983) "Protoplast Isolation and Culture," Handbook of Plant Cell Cultures 1, 124-176 (MacMillan Publishing Co., New York; Davey (1983) "Recent Developments in the Culture and Regeneration of Plant Protoplasts," Protoplasts, pp. 12-29, (Birkhauser, Basel); Dale (1983) "Protoplast Culture and Plant Regeneration of Cereals and Other Recalcitrant Crops," Protoplasts pp. 31-41, (Birkhauser, Basel); Binding (1985) "Regeneration of Plants," Plant Protoplasts, pp. 21-73, (CRC Press, Boca Raton, Fla.). Additional details regarding plant cell culture and regeneration include Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Plant Molecular Biolgy (1993) R. R. D. Croy, Ed. Bios Scientific Publishers, Oxford, U.K. ISBN 0 12 198370 6. Cell culture media in general are also set forth in Atlas and Parks (eds) The Handbook of Microbiological Media (1993) CRC Press, Boca Raton, Fla. Additional information for cell culture is found in available commercial literature such as the Life Science Research Cell Culture Catalogue (1998) from Sigma-Aldrich, Inc (St Louis, Mo.) ("Sigma-LSRCCC") and, e.g., the Plant Culture Catalogue and supplement (e.g., 1997 or later) also from Sigma-Aldrich, Inc (St Louis, Mo.) ("Sigma-PCCS").

The production of transgenic organisms is provided, which may be bacteria, yeast, fungi, animals or plants, transduced with the nucleic acids (e.g., nucleic acids comprising the marker loci and/or QTL noted herein). A thorough discussion of techniques relevant to bacteria, unicellular eukaryotes and cell culture is found in references enumerated herein and are briefly outlined as follows. Several well-known methods of introducing target nucleic acids into bacterial cells are available, any of which may be used. These include: fusion of the recipient cells with bacterial protoplasts containing the DNA, treatment of the cells with liposomes containing the DNA, electroporation, microinjection, cell fusions, projectile bombardment (biolistics), carbon fiber delivery, and infection with viral vectors (discussed further, below), etc. Bacterial cells can be used to amplify the number of plasmids containing DNA constructs. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith (1979) Gene 8:81; Roberts et al. (1987) Nature 328:731; Schneider et al. (1995) Protein Expr. Purif. 6435:10; Ausubel, Sambrook, Berger (all infra). A catalogue of bacteria and bacteriophages useful for cloning is provided, e.g., by the ATCC, e.g., The ATCC Catalogue of Bacteria and Bacteriophage (1992) Gherna et al. (eds) published by the ATCC. Additional basic procedures for sequencing, cloning and other aspects of molecular biology and underlying theoretical considerations are also found in Watson et al. (1992) Recombinant DNA, Second Edition, Scientific American Books, N.Y. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

Introducing Nucleic Acids into Plants

Embodiments include the production of transgenic plants comprising the cloned nucleic acids, e.g., isolated ORFs and cDNAs encoding tolerance genes. Techniques for transforming plant cells with nucleic acids are widely available and can be readily adapted. In addition to Berger, Ausubel and Sambrook, all infra, useful general references for plant cell cloning, culture and regeneration include Jones (ed) (1995) Plant Gene Transfer and Expression Protocols—Methods in Molecular Biology, Volume 49 Humana Press Towata N.J.; Payne et al. (1992) Plant Cell and Tissue Culture in Liquid Systems John Wiley & Sons, Inc. New York, N.Y. (Payne); and Gamborg and Phillips (eds) (1995) Plant Cell, Tissue and Organ Culture; Fundamental Methods Springer Lab Manual, Springer-Verlag (Berlin Heidelberg N.Y.) (Gamborg). A variety of cell culture media are described in Atlas and Parks (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in Croy, (ed.) (1993) Plant Molecular Biology, Bios Scientific Publishers, Oxford, U.K. The nucleic acid constructs, e.g., DNA molecules, plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acids can be introduced into plants according to any of a variety of techniques known in the art. Techniques for transforming a wide variety of higher plant species are also well known and described in widely available technical, scientific, and patent literature. See, e.g., Weising et al. (1988) Ann. Rev. Genet. 22:421-477.

The DNA constructs, for example DNA fragments, plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones (ed) (1995) Plant Gene Transfer and Expression Protocols—Methods in Molecular Biology, Volume 49 Humana Press, Towata, N.J., as well as in the other references noted herein and available in the literature.

For example, the introduction of DNA constructs using polyethylene glycol precipitation is described in Paszkowski et al., EMBO J. 3:2717 (1984). Electroporation techniques are described in Fromm et al., Proc. Natl. Acad. Sci. USA 82:5824 (1985). Ballistic transformation techniques are described in Klein et al., Nature 327:70-73 (1987). Additional details are found in Jones (1995) and Gamborg and Phillips (1995), supra, and in U.S. Pat. No. 5,990,387.

Alternatively, *Agrobacterium*-mediated transformation is employed to generate transgenic plants. *Agrobacterium*-mediated transformation techniques, including disarming and use of binary vectors, are also well described in the scientific literature. See, e.g., Horsch, et al. (1984) Science 233:496; and Fraley et al. (1984) Proc. Natl. Acad. Sci. USA 80:4803 and recently reviewed in Hansen and Chilton (1998) Current Topics in Microbiology 240:22 and Das (1998) Subcellular Biochemistry 29: Plant Microbe Interactions, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: Genetic Engineering, vol. 6, P W J Rigby, Ed., London, Academic Press; and Lichtenstein; C. P., and Draper (1985) In: DNA Cloning, Vol. II, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) Plant Cell Physiol. 25:1353), (3) the vortexing method (see, e.g., Kindle (1990) Proc. Natl. Acad. Sci., (USA) 87:1228.

DNA can also be introduced into plants by direct DNA transfer into pollen as described by Zhou et al. (1983) Methods in Enzymology, 101:433; D. Hess (1987) Intern Rev. Cytol. 107:367; Luo et al. (1988) Plant Mol. Biol. Reporter 6:165. Expression of polypeptide coding genes can be obtained by injection of the DNA into reproductive organs of a plant as described by Pena et al. (1987) Nature 325:274. DNA can also be injected directly into the cells of immature embryos and the desiccated embryos rehydrated as described by Neuhaus et al. (1987) Theor. Appl. Genet. 75:30; and Benbrook et al. (1986) in Proceedings Bio Expo Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Generation/Regeneration of Transgenic Plants

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York); Evans et al. (1983) Protoplasts Isolation and Culture, Handbook of Plant Cell Culture pp. 124-176, Macmillian Publishing Company, New York; and Binding (1985) Regeneration of Plants, Plant Protoplasts pp. 21-73, CRC Press, Boca Raton. Regeneration can also be obtained from plant callus, explants, somatic embryos (Dandekar et al. (1989) J. Tissue Cult. Meth. 12:145; McGranahan, et al. (1990) Plant Cell Rep. 8:512) organs, or parts thereof. Such regeneration techniques are described generally in Klee et al. (1987), Ann. Rev. of Plant Phys. 38:467-486. Additional details are found in Payne (1992) and Jones (1995), both supra, and Weissbach and Weissbach, eds. (1988) Methods for Plant Molecular Biology Academic Press, Inc., San Diego, Calif. This regeneration and growth process includes the steps of selection of transformant cells and shoots, rooting the transformant shoots and growth of the plantlets in soil. These methods are adapted to produce transgenic plants bearing QTLs and other genes isolated according to the methods.

In addition, the regeneration of plants containing the polynucleotides and introduced by *Agrobacterium* into cells of leaf explants can be achieved as described by Horsch et al. (1985) Science 227:1229-1231. In this procedure, transformants are grown in the presence of a selection agent and in a medium that induces the regeneration of shoots in the plant species being transformed as described by Fraley et al. (1983) Proc. Natl. Acad. Sci. (U.S.A.) 80:4803. This procedure typically produces shoots within two to four weeks and these transformant shoots are then transferred to an appropriate root-inducing medium containing the selective agent and an antibiotic to prevent bacterial growth. Transgenic plants may be fertile or sterile.

It is not intended that plant transformation and expression of polypeptides that provide herbicide tolerance be limited to soybean species. Indeed, it is contemplated that the polypeptides that provide tolerance in soybean can also provide a similar phenotype when transformed and expressed in other plants. Examples of plant genuses and species of interest include, but are not limited to, monocots and dicots such as corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (Avena), barley (Hordeum), palm, legumes including beans and peas such as guar, locust bean, fenugreek, garden beans, cowpea, mungbean, lima bean, fava bean, lentils, chickpea, and castor, *Arabidopsis*, vegetables, ornamentals, grasses, conifers, crop and grain plants that provide seeds of interest, oil-seed plants, and other leguminous plants. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Promoters of bacterial origin that operate in plants include the octopine synthase promoter, the nopaline synthase promoter and other promoters derived from native Ti plasmids. See, Herrara-Estrella et al. (1983), Nature, 303:209. Viral promoters include the $^{35}$S and 19S RNA promoters of cauliflower mosaic virus. See, Odell et al. (1985) Nature, 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) EMBO J. 7:3315. Many other promoters are in current use and can be coupled to an exogenous DNA sequence to direct expression of the nucleic acid.

If expression of a polypeptide from a cDNA is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes will typically include a nucleic acid subsequence, a marker gene which confers a selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos or Basta). See, e.g., Padgette et al. (1996) In: Herbicide-Resistant Crops (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See Vasil (1996) In: Herbicide-Resistant Crops (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included, provided that these parts comprise cells comprising the isolated nucleic acid. Progeny and variants, and mutants of the regenerated plants are also included, provided that these parts comprise the introduced nucleic acid sequences.

Transgenic or introgressed plants expressing a polynucleotide can be screened for transmission of the nucleic acid by, for example, standard nucleic acid detection methods or by immunoblot protocols. Expression at the RNA level can be determined to identify and quantitate expression-positive plants. Standard techniques for RNA analysis can be employed and include RT-PCR amplification assays using oligonucleotide primers designed to amplify only heterologous or introgressed RNA templates and solution hybridization assays using marker or linked QTL specific probes. Plants can also be analyzed for protein expression, e.g., by Western immunoblot analysis using antibodies that recognize the encoded polypeptides. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

In one example, a transgenic plant that is homozygous for the added heterologous nucleic acid; e.g., a transgenic plant that contains two added nucleic acid sequence copies, e.g., a gene at the same locus on each chromosome of a homologous chromosome pair is provided. A homozygous transgenic plant can be obtained by sexually mating (self-fertilizing) a heterozygous transgenic plant that contains a single added heterologous nucleic acid, germinating some of the seed produced and analyzing the resulting plants produced for altered expression of a polynucleotide relative to a control plant (e.g., a native, non-transgenic plant). Back-crossing to a parental plant and out-crossing with a non-transgenic plant can be used to introgress the heterologous nucleic acid into a selected background (e.g., an elite or exotic soybean line).

Stacking of Traits and Additional Traits of Interest

In some embodiments, the polynucleotide conferring the tolerance in the plants are engineered into a molecular stack with at least one additional polynucleotide. The additional polynucleotide may confer any additional trait of interest, such as tolerance to an additional herbicide, insects, disease, or any other desirable trait. A trait, as used herein, refers to the phenotype derived from a particular sequence or groups of sequences. For example, herbicide-tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) Gene 48: 109; Lee et al. (2003) Appl. Environ. Microbiol. 69: 4648-4657 (Vip3A); Galitzky et al. (2001) Acta Crystallogr. D. Biol. Crystallogr. 57:1101-1109 (Cry3Bb1); and Herman et al. (2004) J. Agric. Food Chem. 52: 2726-2734 (Cry1F)), lectins (Van Damme et al. (1994) Plant Mol. Biol. 24: 825, pentin (described in U.S. Pat. No. 5,981,722), and the like. The combinations generated can also include multiple copies of any one of the polynucleotides of interest.

In some embodiments, herbicide-tolerance polynucleotide may be stacked with other herbicide-tolerance traits to create a transgenic plant with further improved properties. Other herbicide-tolerance polynucleotides that could be used in such embodiments include those conferring tolerance to the same herbicide by other modes of action, or a different herbicide. Other traits that could be combined with herbicide-tolerance polynucleotides include those derived from polynucleotides that confer on the plant the capacity to produce a higher level of 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; U.S. Pat. No. Re. 36,449; U.S. Pat. Nos. RE 37,287 E; and 5,491,288; and WO 97/04103; WO 00/66746; WO 01/66704; and WO 00/66747. Other traits that could be combined with herbicide-tolerance polynucleotides include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

In some embodiments, herbicide-tolerance polynucleotides of the plants may be stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Traits conferring tolerance to such herbicides in plants are described in U.S. Pat. Nos. 6,245,968 B1; 6,268,549; and 6,069,115; and WO 99/23886. Other examples of suitable herbicide-tolerance traits that could be stacked with herbicide-tolerance polynucleotides include aryloxyalkanoate dioxygenase polynucleotides (which reportedly confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) J. Biol. Chem. 280: 24759-24767.

Other examples of herbicide-tolerance traits that could be combined with herbicide-tolerance polynucleotides include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the herbicide-tolerance polynucleotides include those conferred by polynucleotides conferring altered protoporphyrinogen oxidase (protox) activity, as described in U.S. Pat. Nos. 6,288,306 B1; 6,282,837 B1; and 5,767,373; and WO 01/12825. Plants containing such polynucleotides can exhibit improved tolerance to any of a variety of herbicides which target the protox enzyme (also referred to as "protox inhibitors").

Other examples of herbicide-tolerance traits that could be combined with herbicide-tolerance polynucleotides include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "Correlation of Corn (*Zea mays*) Inbred Response to Nicosulfuron and Mesotrione," poster presented at the WSSA Annual Meeting in Kansas City, Mo., Feb. 9-12, 2004; Green (1998) Weed Technology 12: 474-477; Green and Ulrich (1993) Weed Science 41: 508-516. The trait(s) responsible for these tolerances can be combined by breeding or via other methods with herbicide-tolerance polynucleotides to provide a plant as well as methods of use thereof.

In this manner, plants that are more tolerant to multiple herbicides are disclosed. Accordingly, methods for growing a crop (i.e., for selectively controlling weeds in an area of cultivation) that comprise treating an area of interest (e.g., a field or area of cultivation) with at least one herbicide to which the plant is tolerant are likewise disclosed. In some embodiments, methods further comprise treatment with additional herbicides to which the plant is tolerant. In such embodiments, generally the methods permit selective control of weeds without significantly damaging the crop. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

Herbicide-tolerant traits can also be combined with at least one other trait to produce plants that further comprise a variety of desired trait combinations including, but not limited to, traits desirable for animal feed such as high oil content (e.g., U.S. Pat. No. 6,232,529); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) Appl. Microbiol. Biotechnol. 59: 224-230) and OLCH (high oleic acid content; see, e.g., Fernandez-Moya et al. (2005) J. Agric. Food Chem. 53: 5326-5330).

Herbicide-tolerant traits of interest can also be combined with other desirable traits such as, for example, fumonisim detoxification genes (U.S. Pat. No. 5,792,931), avirulence and disease resistance genes (Jones et al. (1994) Science 266: 789; Martin et al. (1993) Science 262: 1432; Mindrinos et al. (1994) Cell 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In another embodiment, the herbicide-tolerant traits of interest can also be combined with the Rcg1 sequence or biologically active variant or fragment thereof. The Rcg1 sequence is an anthracnose stalk rot resistance gene in corn. See, e.g., U.S. patent application Ser. No. 11/397,153, 11/397,275, and 11/397,247, each of which is herein incorporated by reference.

These stacked combinations can be created by any method including, but not limited to, breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, e.g., WO99/25821, WO99/25854, WO99/25840, WO99/25855, and WO99/25853, all of which are herein incorporated by reference.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48: 109); and the like.

Genes encoding disease resistance traits include detoxification genes, such as against fumonosin (U.S. Pat. No. 5,792,931); avirulence (avr) and disease resistance (R) genes (Jones et al. (1994) Science 266: 789; Martin et al. (1993) Science 262: 1432; and Mindrinos et al. (1994) Cell 78: 1089); and the like.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Polynucleotide Constructs

In specific embodiments, one or more of the herbicide-tolerant polynucleotides employed in the methods and compositions can be provided in an expression cassette for expression in the plant or other organism of interest. The cassette will include 5' and 3' regulatory sequences operably linked to a herbicide-tolerance polynucleotide. "Operably linked" is intended to mean a functional linkage between two or more elements. For example, an operable linkage between a polynucleotide of interest and a regulatory sequence (e.g., a promoter) is functional link that allows for expression of the polynucleotide of interest. Operably linked elements may be contiguous or non-contiguous. When used to refer to the joining of two protein coding regions, by "operably linked" is intended that the coding regions are in the same reading frame. When used to refer to the effect of an enhancer, "operably linked" indicates that the enhancer increases the expression of a particular polynucleotide or polynucleotides of interest. Where the polynucleotide or polynucleotides of interest encode a polypeptide, the encoded polypeptide is produced at a higher level.

The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the herbicide-tolerance polynucleotide to be under the transcriptional regulation of the regulatory regions. The expression cassette may additionally contain other genes, including other selectable marker genes. Where a cassette contains more than one polynucleotide, the polynucleotides in the cassette may be transcribed in the same direction or in different directions (also called "divergent" transcription).

An expression cassette comprising a herbicide-tolerance polynucleotide will include in the 5'-3' direction of transcription a transcriptional and translational initiation region (i.e., a promoter), a herbicide-tolerance polynucleotide, and a transcriptional and translational termination region (i.e., termination region) functional in plants or the other organism of interest. Accordingly, plants having such expression cassettes are also provided. The regulatory regions (i.e., promoters, transcriptional regulatory regions, and translational termination regions) and/or the herbicide-tolerance polynucleotide may be native (i.e., analogous) to the host cell or to each other. Alternatively, the regulatory regions and/or the herbicide-tolerance polynucleotide may be heterologous to the host cell or to each other.

While it may be optimal to express polynucleotides using heterologous promoters, native promoter sequences may be used. Such constructs can change expression levels and/or expression patterns of the encoded polypeptide in the plant or plant cell. Expression levels and/or expression patterns of the encoded polypeptide may also be changed as a result of an additional regulatory element that is part of the construct, such as, for example, an enhancer. Thus, the phenotype of the plant or cell can be altered even though a native promoter is used.

The termination region may be native with the transcriptional initiation region, may be native with the operably linked herbicide-tolerance polynucleotide of interest, may be native with the plant host, or may be derived from another source (i.e., foreign or heterologous) to the promoter, the herbicide-tolerance polynucleotide of interest, the plant host, or any combination thereof. Convenient termination regions are available from the Ti-plasmid of *A. tumefaciens*, such as the octopine synthase and nopaline synthase termination regions, or can be obtained from plant genes such as the *Solanum tuberosum* proteinase inhibitor II gene. See Guerineau et al. (1991) Mol. Gen. Genet. 262: 141-144; Proudfoot (1991) Cell 64: 671-674; Sanfacon et al. (1991) Genes Dev. 5: 141-149; Mogen et al. (1990) Plant Cell 2: 1261-1272; Munroe et al. (1990) Gene 91: 151-158; Ballas et al. (1989) Nucleic Acids Res. 17: 7891-7903; and Joshi et al. (1987) Nucleic Acids Res. 15: 9627-9639.

A number of promoters can be used, including the native promoter of the polynucleotide sequence of interest. The promoters can be selected based on the desired outcome. The polynucleotides of interest can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313: 810-812); rice actin (McElroy et al. (1990) Plant Cell 2: 163-171); the maize actin promoter; the ubiquitin promoter (see, e.g., Christensen et al. (1989) Plant Mol. Biol. 12: 619-632; Christensen et al. (1992) Plant Mol. Biol. 18: 675-689; Callis et al. (1995) Genetics 139: 921-39); pEMU (Last et al. (1991) Theor. Appl. Genet. 81: 581-588); MAS (Velten et al. (1984) EMBO J. 3: 2723-2730); ALS promoter (U.S. Pat. No. 5,659,026), and the like. Other constitutive promoters include, for example, those described in U.S. Pat. Nos. 5,608,149; 5,608,144; 5,604,121; 5,569,597; 5,466,785; 5,399,680; 5,268,463; 5,608,142; and 6,177,611. Some promoters show improved expression when they are used in conjunction with a native 5' untranslated region and/or other elements such as, for example, an intron. For example, the maize ubiquitin promoter is often placed upstream of a polynucleotide of interest along with at least a portion of the 5' untranslated region of the ubiquitin gene, including the first intron of the maize ubiquitin gene.

Chemical-regulated promoters can be used to modulate the expression of a gene in a plant through the application of an exogenous chemical regulator. Depending upon the objective, the promoter may be a chemical-inducible promoter for which application of the chemical induces gene expression or the promoter may be a chemical-repressible promoter for which application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, e.g., the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, e.g., Gatz et al. (1991) Mol. Gen. Genet. 227: 229-237, and U.S. Pat. Nos. 5,814,618 and 5,789,156), herein incorporated by reference).

Tissue-preferred promoters can be utilized to target enhanced herbicide-tolerance polypeptide expression within a particular plant tissue. Tissue-preferred promoters include Yamamoto et al. (1997) Plant J. 12: 255-265; Kawamata et al. (1997) Plant Cell Physiol. 38: 792-803; Hansen et al. (1997) Mol. Gen. Genet. 254: 337-343; Russell et al. (1997) Transgenic Res. 6: 157-168; Rinehart et al. (1996) Plant Physiol. 112:1331-1341; Van Camp et al. (1996) Plant Physiol. 112: 525-535; Canevascini et al. (1996) Plant Physiol. 112: 513-524; Yamamoto et al. (1994) Plant Cell Physiol. 35: 773-778; Lam (1994) Results Probl. Cell Differ. 20: 181-196; Orozco et al. (1993) Plant Mol. Biol. 23: 1129-1138; Matsuoka et al. (1993) Proc Natl. Acad. Sci. USA 90: 9586-9590; and Guevara-Garcia et al. (1993) Plant J. 4: 495-505. Such promoters can be modified, if necessary, for weak expression.

Leaf-preferred promoters are known in the art. See, e.g., Yamamoto et al. (1997) Plant J. 12: 255-265; Kwon et al. (1994) Plant Physiol. 105: 357-67; Yamamoto et al. (1994) Plant Cell Physiol. 35: 773-778; Gotor et al. (1993) Plant J. 3: 509-18; Orozco et al. (1993) Plant Mol. Biol. 23: 1129-1138; and Matsuoka et al. (1993) Proc. Natl. Acad. Sci. USA 90: 9586-9590.

Root-preferred promoters are known and can be selected from the many available from the literature or isolated de novo from various compatible species. See, e.g., Hire et al. (1992) Plant Mol. Biol. 20(2): 207-218 (soybean root-specific glutamine synthetase gene); Keller and Baumgartner (1991) Plant Cell 3: 1051-1061 (root-specific control element in the GRP 1.8 gene of French bean); Sanger et al. (1990) Plant Mol. Biol. 14: 433-443 (root-specific promoter of the mannopine synthase (MAS) gene of *Agrobacterium tumefaciens*); and Miao et al. (1991) Plant Cell 3: 11-22 (full-length cDNA clone encoding cytosolic glutamine synthetase (GS), which is expressed in roots and root nodules of soybean). See also Bogusz et al. (1990) Plant Cell 2: 633-641, where two root-specific promoters are described. Leach and Aoyagi (1991) describe their analysis of the promoters of the highly expressed rolC and rolD root-inducing genes of *Agrobacterium rhizogenes* (see Plant Science (Limerick) 79: 69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8: 343-350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29: 759-772); and rolB promoter (Capana et al. (1994) Plant Mol. Biol. 25: 681-691. See also U.S. Pat. Nos. 5,837,876; 5,750,386; 5,633,363; 5,459,252; 5,401,836; 5,110,732; and 5,023,179.

Seed-preferred promoters include both seed-specific promoters (those promoters active during seed development such as promoters of seed storage proteins) as well as "seed-germinating" promoters (those promoters active during seed germination). See Thompson et al. (1989) BioEssays 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean .beta.-phaseolin, napin, .beta.-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

Additional promoters of interest include the SCP1 promoter (U.S. Pat. No. 6,072,050), the HB2 promoter (U.S. Pat. No. 6,177,611) and the SAMS promoter (US20030226166 and SEQ ID NO: 87 and biologically active variants and fragments thereof); each of which is herein incorporated by reference. In addition, as discussed elsewhere herein, various enhancers can be used with these promoters including, for example, the ubiquitin intron (i.e, the maize ubiquitin intron 1 (see, e.g., NCBI sequence S94464), the omega enhancer or the omega prime enhancer (Gallie et al. (1989) Molecular Biology of RNA ed. Cech (Liss, N.Y.) 237-256 and Gallie et al. Gene (1987) 60:217-25), or the 35S enhancer; each of which is incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as .beta.-galactosidase and fluorescent proteins such as green fluorescent protein (GFP) (Su et al. (2004) Biotechnol Bioeng 85: 610-9 and Fetter et al. (2004) Plant Cell 16: 215-28), cyan florescent protein (CYP) (Bolte et al. (2004) J. Cell Science 117: 943-54 and Kato et al. (2002) Plant Physiol 129: 913-42), and yellow fluorescent protein (PhiYFP from Evrogen, see, Bolte et al. (2004) J. Cell Science 117: 943-54). For additional selectable markers, see generally Yarranton (1992) Curr. Opin. Biotech. 3: 506-511; Christopherson et al. (1992) Proc. Natl. Acad. Sci. USA 89: 6314-6318; Yao et al. (1992) Cell 71: 63-72; Reznikoff (1992) Mol. Microbiol. 6: 2419-2422; Barkley et al. (1980) in The Operon, pp. 177-220; Hu et al. (1987) Cell 48: 555-566; Brown et al. (1987) Cell 49: 603-612; Figge et al. (1988) Cell 52: 713-722; Deuschle et al. (1989) Proc. Natl. Acad. Aci. USA 86: 5400-5404; Fuerst et al. (1989) Proc. Natl. Acad. Sci. USA 86: 2549-2553; Deuschle et al. (1990) Science 248: 480-483; Gossen (1993) Ph.D. Thesis, University of Heidelberg; Reines et al. (1993) Proc. Natl. Acad. Sci. USA 90: 1917-1921; Labow et al. (1990) Mol. Cell. Biol. 10: 3343-3356; Zambretti et al. (1992) Proc. Natl. Acad. Sci. USA 89: 3952-3956; Baim et al. (1991) Proc. Natl. Acad. Sci. USA 88: 5072-5076; Wyborski et al. (1991) Nucleic Acids Res. 19: 4647-4653; Hillenand-Wissman (1989) Topics Mol. Struc. Biol. 10: 143-162; Degenkolb et al. (1991) Antimicrob. Agents Chemother. 35: 1591-1595; Kleinschnidt et al. (1988) Biochemistry 27: 1094-1104; Bonin (1993) Ph.D. Thesis, University of Heidelberg; Gossen et al. (1992) Proc. Natl. Acad. Sci. USA 89: 5547-5551; Oliva et al. (1992) Antimicrob. Agents Chemother. 36: 913-919; Hlavka et al. (1985) Handbook of Experimental Pharmacology, Vol. 78 (Springer-Verlag, Berlin); Gill et al. (1988) Nature 334: 721-724. Such disclosures are herein incorporated by reference. The above list of selectable marker genes is not meant to be limiting. Any selectable marker gene can be used, including the GAT gene and/or HRA gene.

Methods are known in the art of increasing the expression level of a polypeptide in a plant or plant cell, for example, by inserting into the polypeptide coding sequence one or two G/C-rich codons (such as GCG or GCT) immediately adjacent to and downstream of the initiating methionine ATG codon. Where appropriate, the polynucleotides may be modified for increased expression in the transformed plant. That is, the polynucleotides can be synthesized substituting in the polypeptide coding sequence one or more codons which are less frequently utilized in plants for codons encoding the same amino acid(s) which are more frequently utilized in plants, and introducing the modified coding sequence into a plant or plant cell and expressing the modified coding sequence. See, e.g., Campbell and Gowri (1990) Plant Physiol. 92: 1-11 for a discussion of host-preferred codon usage. Methods are available in the art for synthesizing plant-preferred genes. See, e.g., U.S. Pat. Nos. 5,380,831, and 5,436,391, and Murray et al. (1989) Nucleic Acids Res. 17: 477-498, herein incorporated by reference. Embodiments comprising such modifications are also a feature disclosed.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. "Enhancers" such as the CaMV 35S enhancer may also be used (see, e.g., Benfey et al. (1990) EMBO J. 9: 1685-96), or other enhancers may be used. For example, the sequence set forth in SEQ ID NO: 1, 72, 79, 84, 85, 88, or 89 or a biologically active variant or fragment thereof can be used. See also U.S. Utility application Ser. No. 11/508,045, entitled "Methods and Compositions for the Expression of a Polynucleotide of Interest." As used herein, an enhancer, when operably linked to an appropriate promoter, will modulate the level of transcription of an operably linked polynucleotide of interest. Biologically active fragments and variants of the enhancer domain may retain the biological activity of modulating (increase or decrease) the level of transcription when operably linked to an appropriate promoter.

Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to another polynucleotide as determined by sequence alignment programs and parameters. Variants of a particular polynucleotides also include those encoding a polypeptide having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to a reference polypeptide as determined by sequence alignment programs and parameters. Polypeptide variants include those encoded by variant polynucleotides, and those having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to a reference polypeptide as determined by sequence alignment programs and parameters.

The expression cassette may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86: 6126-6130); potyvirus leaders, for example, TEV leader (Tobacco Etch Virus) (Gallie et al. (1995) Gene 165(2): 233-238), MDMV leader (Maize Dwarf Mosaic Virus) (Virology 154: 9-20), and human immunoglobulin heavy-chain binding protein (BiP) (Macejak et al. (1991) Nature 353: 90-94); untranslated leader from the coat protein mRNA of alfalfa mosaic virus (AMV RNA 4) (Jobling et al. (1987) Nature 325: 622-625); tobacco mosaic virus leader (TMV) (Gallie et al. (1989) in Molecular Biology of RNA, ed. Cech (Liss, N.Y.), pp. 237-256); and maize chlorotic mottle virus leader (MCMV) (Lommel et al. (1991) Virology 81: 382-385). See also, Della-Cioppa et al. (1987) Plant Physiol. 84: 965-968.

In preparing the expression cassette, the various polynucleotide fragments may be manipulated, so as to provide for sequences to be in the proper orientation and, as appropriate, in the proper reading frame. Toward this end, adapters or linkers may be employed to join the fragments or other manipulations may be involved to provide for convenient restriction sites, removal of superfluous material such as the removal of restriction sites, or the like. For this purpose, in vitro mutagenesis, primer repair, restriction, annealing, resubstitutions, e.g., transitions and transversions, may be involved. Standard recombinant DNA and molecular cloning techniques used herein are well known in the art and are described more fully, for example, in Sambrook et al. (1989) Molecular Cloning: A Laboratory Manual (Cold Spring Harbor Laboratory Press, Cold Spring Harbor) (also known as "Maniatis").

In some embodiments, the polynucleotide of interest is targeted to the chloroplast for expression. In this manner, where the polynucleotide of interest is not directly inserted into the chloroplast, the expression cassette will additionally contain a nucleic acid encoding a transit peptide to direct the gene product of interest to the chloroplasts. Such transit peptides are known in the art. See, e.g., Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84: 965-968; Romer et al. (1993) Biochem. Biophys. Res. Commun. 196: 1414-1421; and Shah et al. (1986) Science 233: 478-481.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30: 769-780; Schnell et al. (1991) J. Biol. Chem. 266(5): 3335-3342); 5-(enolpyruvyl)shikimate-3-phosphate synthase (EPSPS) (Archer et al. (1990) J. Bioenerg Biomemb. 22(6): 789-810); tryptophan synthase (Zhao et al. (1995) J. Biol. Chem. 270(11): 6081-6087); plastocyanin (Lawrence et al. (1997) J. Biol. Chem. 272(33): 20357-20363); chorismate synthase (Schmidt et al. (1993) J. Biol. Chem. 268(36): 27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84: 965-968; Romer et al. (1993) Biochem. Biophys. Res. Commun. 196: 1414-1421; and Shah et al. (1986) Science 233: 478-481.

Methods for transformation of chloroplasts are known in the art. See, e.g., Svab et al. (1990) Proc. Natl. Acad. Sci. USA 87: 8526-8530; Svab and Maliga (1993) Proc. Natl. Acad. Sci. USA 90: 913-917; Svab and Maliga (1993) EMBO J. 12: 601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91: 7301-7305.

The polynucleotides of interest to be targeted to the chloroplast may be optimized for expression in the chloroplast to account for differences in codon usage between the plant nucleus and this organelle. In this manner, the polynucleotide of interest may be synthesized using chloroplast-preferred codons. See, e.g., U.S. Pat. No. 5,380,831, herein incorporated by reference.

Methods of Introducing

Compositions include plants generated by introducing a polypeptide or polynucleotide into a plant. "Introducing" is intended to mean presenting to the plant the polynucleotide or polypeptide in such a manner that the sequence gains access to the interior of a cell of the plant. The methods do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, virus-mediated methods, and breeding.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell (i.e., monocot or dicot) targeted for transformation. Suitable methods of introducing polypeptides and polynucleotides into plant cells include microinjection (Crossway et al. (1986) Biotechniques 4: 320-334), electroporation (Riggs et al. (1986) Proc. Natl. Acad. Sci. USA 83: 5602-5606, *Agrobacterium*-mediated transformation (U.S. Pat. No. 5,563,055 and U.S. Pat. No. 5,981,840), direct gene transfer (Paszkowski et al. (1984) EMBO J. 3: 2717-2722), and ballistic particle acceleration (see, for example, U.S. Pat. No. 4,945,050; U.S. Pat. No. 5,879,918; U.S. Pat. Nos. 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) Biotechnology 6: 923-926); and Lec1 transformation (WO 00/28058). Also see Weissinger et al. (1988) Ann. Rev. Genet. 22: 421-477; Sanford et al. (1987) Particulate Science and Technology 5: 27-37 (onion); Christou et al. (1988) Plant Physiol. 87: 671-674 (soybean); McCabe et al. (1988) Bio/Technology 6: 923-926 (soybean); Finer and McMullen (1991) In Vitro Cell Dev. Biol. 27P: 175-182 (soybean); Singh et al. (1998) Theor. Appl. Genet. 96:319-324 (soybean); Datta et al. (1990) Biotechnology 8: 736-740 (rice); Klein et al. (1988) Proc. Natl. Acad. Sci. USA 85:4305-4309 (maize); Klein et al. (1988) Biotechnology 6:559-563 (maize); U.S. Pat. Nos. 5,240,855; 5,322,783; and, 5,324,646; Klein et al. (1988) Plant Physiol. 91: 440-444 (maize); Fromm et al. (1990) Biotechnology 8: 833-839 (maize); protocols published electronically by "IP.com" under the permanent publication identifiers IPCOM000033402D, IPCOM000033402D, and IPCOM000033402D and available at the "IP.com" website (cotton); Hooykaas-Van Slogteren et al. (1984) Nature (London) 311: 763-764; U.S. Pat. No. 5,736,369 (cereals); Bytebier et al. (1987) Proc. Natl. Acad. Sci. USA 84: 5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9: 415-418 and Kaeppler et al. (1992) Theor. Appl. Genet. 84: 560-566 (whisker-mediated transformation); D'Halluin et al. (1992) Plant Cell 4: 1495-1505 (electroporation); Li et al. (1993) Plant Cell Reports 12: 250-255 and Christou and Ford (1995) Annals of Botany 75: 407-413 (rice); Osjoda et al. (1996) Nature Biotechnology 14: 745-750 (maize via *Agrobacterium tumefaciens*); all of which are herein incorporated by reference.

In specific embodiments, herbicide-tolerance or other desirable sequences can be provided to a plant using a variety of transient transformation methods. Such transient transformation methods include, but are not limited to, the introduction of the polypeptide or variants and fragments thereof directly into the plant or the introduction of a transcript into the plant. Such methods include, for example, microinjection or particle bombardment. See, e.g., Crossway et al. (1986) Mol. Gen. Genet. 202: 179-185; Nomura et al. (1986) Plant Sci. 44: 53-58; Hepler et al. (1994) Proc. Natl. Acad. Sci. 91: 2176-2180 and Hush et al. (1994) The Journal of Cell Science 107: 775-784, all of which are herein incorporated by reference. Alternatively, a herbicide-tolerance polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3143).

In other embodiments, polynucleotides may be introduced into plants by contacting plants with a virus or viral nucleic acids. Generally, such methods involve incorporating a nucleotide construct within a viral DNA or RNA molecule. It is recognized that a polypeptide of interest may be initially synthesized as part of a viral polyprotein, which later may be processed by proteolysis in vivo or in vitro to produce the desired recombinant protein. Further, it is recognized that useful promoters may include promoters utilized for transcription by viral RNA polymerases. Methods for introducing polynucleotides into plants and expressing a polypeptide encoded thereby, involving viral DNA or RNA molecules, are known in the art. See, e.g., U.S. Pat. Nos. 5,889,191, 5,889,190, 5,866,785, 5,589,367, 5,316,931, and Porta et al. (1996) Molecular Biotechnology 5: 209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, e.g., WO99/25821, WO99/25854, WO99/25840, WO99/25855, and WO99/25853, all of which are herein incorporated by reference. Briefly, a polynucleotide can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, e.g., McCormick et al. (1986) Plant Cell Reports 5: 81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having a polynucleotide conferring tolerance to a PPO inhibitor stably incorporated into their genome are provided.

In specific embodiments, a polypeptide or the polynucleotide of interest is introduced into the plant cell. Subsequently, a plant cell having the introduced sequence is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides in the plant. Plant forming conditions are well known in the art and discussed briefly elsewhere herein.

It is also recognized that the level and/or activity of a polypeptide of interest may be modulated by employing a polynucleotide that is not capable of directing, in a transformed plant, the expression of a protein or an RNA. For example, the polynucleotides may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96: 8774-8778; herein incorporated by reference.

It is therefore recognized that methods disclosed do not depend on the incorporation of the entire polynucleotide into the genome, only that the plant or cell thereof is altered as a result of the introduction of the polynucleotide into a cell. In one embodiment, the genome may be altered following the introduction of the polynucleotide into a cell. For example, the polynucleotide, or any part thereof, may incorporate into the genome of the plant. Alterations to the genome include, but are not limited to, additions, deletions, and substitutions of nucleotides into the genome. While the methods disclosed do not depend on additions, deletions, and substitutions of any particular number of nucleotides, it is recognized that such additions, deletions, or substitutions comprises at least one nucleotide.

Plants may be produced by any suitable method, including breeding. Plant breeding can be used to introduce desired characteristics (e.g., a stably incorporated transgene or a genetic variant or genetic alteration of interest) into a particular plant line of interest, and can be performed in any of several different ways. Pedigree breeding starts with the crossing of two genotypes, such as an elite line of interest and one other elite inbred line having one or more desirable characteristics (i.e., having stably incorporated a polynucleotide of interest, having a modulated activity and/or level of the polypeptide of interest, etc.) which complements the elite plant line of interest. If the two original parents do not provide all the desired characteristics, other sources can be included in the breeding population. In the pedigree method, superior plants are selfed and selected in successive filial generations. After a sufficient amount of inbreeding, successive filial generations will serve to increase seed of the developed inbred. In specific embodiments, the inbred line comprises homozygous alleles at about 95% or more of its loci. Various techniques known in the art can be used to facilitate and accelerate the breeding (e.g., backcrossing) process, including, for example, the use of a greenhouse or growth chamber with accelerated day/night cycles, the analysis of molecular markers to identify desirable progeny, and the like.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, a method of making a backcross conversion of an inbred line of interest comprising the steps of crossing a plant from the inbred line of interest with a donor plant comprising at least one mutant gene or transgene conferring a desired trait (e.g., herbicide tolerance), selecting an F1 progeny plant comprising the mutant gene or transgene conferring the desired trait, and backcrossing the selected F1 progeny plant to a plant of the inbred line of interest is provided. This method may further comprise the step of obtaining a molecular marker profile of the inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of the inbred line of interest with a different plant to make F1 hybrid seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation such as X-rays, Gamma rays (e.g., cobalt 60 or cesium 137), neutrons, (product of nuclear fission of uranium 235 in an atomic reactor), Beta radiation (emitted from radioisotopes such as phosphorus 32 or carbon 14), or ultraviolet radiation (typically from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

Methods of Modulating Expression

In some embodiments, the activity and/or level of the polypeptide is modulated (i.e., increased or decreased). An increase in the level and/or activity of the polypeptide can be achieved by providing the polypeptide to the plant. As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having the desired activity.

Methods of Controlling Weeds

Methods are provided for controlling weeds in an area of cultivation, preventing the development or the appearance of herbicide resistant weeds in an area of cultivation, producing a crop, and increasing crop safety. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

The PPO inhibitor plants display tolerance to herbicides and therefore allow for the application of one or more herbicides at rates that would significantly damage control plants and further allow for the application of combinations of herbicides at lower concentrations than normally applied which still continue to selectively control weeds. In addition, the PPO inhibitor-tolerant plants can be used in combination with herbicide blends technology and thereby make the application of chemical pesticides more convenient, economical, and effective for the producer.

The methods comprise planting the area of cultivation with PPO inhibitor-tolerant crop seeds or plants, and applying to any crop, crop part, weed or area of cultivation thereof an effective amount of a PPO inhibitor containing herbicide of interest. It is recognized that the herbicide can be applied before and/or after the crop is planted in the area of cultivation. Such herbicide applications can include an application of any PPO inhibitor chemistry, or any combination thereof. In some examples, a diphenyl ether, triazolinone, N-phenylphthalimide, pyrimidindione and/or oxadiazole containing herbicide formulation is applied. In some examples the herbicide formulation comprises acifluorfen, fomesafen, oxyfluorfen, lactofen, sulfentrazone, carfentrasone, azafeniden flumiclorac, flumioxazin, oxadiazon, fluthiacet benzfendizone, butagenacil and/or saflufenacil.

In other examples, the combination of herbicides comprises a glyphosate, a glufosinate, a dicamba, a bialaphos, a phosphinothricin, a protox inhibitor, a sulfonylurea, an imidazolinone, a chlorsulfuron, an imazapyr, a chlorimuron-ethyl, a quizalofop, an HPPD, a PPO inhibitor, and/or a fomesafen, or combinations thereof, wherein said effective amount is tolerated by the crop and controls weeds. Any effective amount of these herbicides can be applied, wherein the effective amount is any amount that differentiates between plant cells, plants, and/or seed comprising a PPO inhibitor tolerance allele, a PPO inhibitor polynucleotide, and/or a polynucleotide encoding an ABC transporter protein that confers tolerance to herbicide formulations comprising a PPO inhibitor. In some examples the herbicides are applied simultaneously, in some examples the herbicides are applied sequentially, in some examples the herbicides are applied as pre-emergent treatments, in some examples the herbicides are applied as post-emergent treatments, in some examples the herbicides are applied as a combination of pre- and post-emergent treatments.

In some examples, the method of controlling weeds comprises planting the area with PPO inhibitor tolerant crop seeds or plants and applying to the crop, crop part, seed of said crop or the area under cultivation, an effective amount of a herbicide, wherein said effective amount comprises an amount that is not tolerated by a control crop when applied to the control crop, crop part, seed or the area of cultivation, wherein the control crop does not express a polynucleotide that encodes an herbicide-tolerance polypeptide. In specific embodiments, combinations of herbicides may be used, such as when an additional tolerance trait is incorporated into the plant.

In another embodiment, the method of controlling weeds comprises planting the area with a PPO inhibitor-tolerant crop seeds or plant and applying to the crop, crop part, seed of said crop or the area under cultivation, an effective amount of a herbicide, wherein said effective amount comprises a level that is above the recommended label use rate for the crop, wherein said effective amount is tolerated when applied to the PPO inhibitor-tolerant crop, crop part, seed, or the area of cultivation thereof.

Any herbicide can be applied to the tolerant crop, crop part, or the area of cultivation containing said crop plant. Classifications of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith (1997) Weed Technology 11: 384-393). An abbreviated version of the HRAC classification (with notes regarding the corresponding WSSA group) is set forth below:

| HRAC Group | Mode of Action | Chemical Family | Active Ingredient | WSSA Group |
|---|---|---|---|---|
| A | Inhibition of acetyl CoA carboxylase (ACCase) | Aryloxyphenoxy-propionate "FOPs" | clodinafop-propargyl<br>cyhalofop-butyl<br>diclofop-methyl<br>fenoxaprop-P-ethyl<br>fluazifop-P-butyl<br>haloxyfop-R-methyl<br>propaquizafop<br>quizalofop-P-ethyl | 1 |
| | | Cyclohexanedione "DIMs" | alloxydim<br>butroxydim<br>clethodim<br>cycloxydim<br>profoxydim<br>sethoxydim<br>tepraloxydin<br>tralkoxydim | |
| | | Phenylpyrazoline "DEN" | pinoxaden | |
| B | Inhibition of acetolactate synthase ALS (acetohydroxyacid synthase AHAS) | Sulfonylurea | amidosulfuron<br>azimsulfuron<br>bensulfuron-methyl<br>chlorimuron-ethyl<br>chlorsulfuron<br>cinosulfuron<br>cyclosulfamuron<br>ethametsulfuron-methyl<br>ethoxysulfuron<br>flazasulfuron<br>flupyrsulfuron-methyl-Na<br>foramsulfuron<br>halosulfuron-methyl<br>imazosulfuron<br>iodosulfuron<br>mesosulfuron<br>metsulfuron-methyl<br>nicosulfuron<br>oxasulfuron | 2 |

-continued

| HRAC Group | Mode of Action | Chemical Family | Active Ingredient | WSSA Group |
|---|---|---|---|---|
| | | | primisulfuron-methyl | |
| | | | prosulfuron | |
| | | | pyrazosulfuron-ethyl | |
| | | | rimsulfuron | |
| | | | sulfometuron-methyl | |
| | | | sulfosulfuron | |
| | | | thifensulfuron-methyl | |
| | | | triasulfuron | |
| | | | tribenuron-methyl | |
| | | | trifloxysulfuron | |
| | | | triflusulfuron-methyl | |
| | | | tritosulfuron | |
| | | Imidazolinone | imazapic | |
| | | | imazamethabenz-methyl | |
| | | | imazamox | |
| | | | imazapyr | |
| | | | imazaquin | |
| | | | imazethapyr | |
| | | Triazolopyrimidine | cloransulam-methyl | |
| | | | diclosulam | |
| | | | florasulam | |
| | | | flumetsulam | |
| | | | metosulam | |
| | | | penoxsulam | |
| | | Pyrimidinyl(thio)benzoate | bispyribac-Na | |
| | | | pyribenzoxim | |
| | | | pyriftalid | |
| | | | pyrithiobac-Na | |
| | | | pyriminobac-methyl | |
| | | Sulfonylaminocarbonyl-triazolinone | flucarbazone-Na | |
| | | | propoxycarbazone-Na | |
| C1 | Inhibition of photosynthesis at photosystem II | Triazine | ametryne | 5 |
| | | | atrazine | |
| | | | cyanazine | |
| | | | desmetryne | |
| | | | dimethametryne | |
| | | | prometon | |
| | | | prometryne | |
| | | | propazine | |
| | | | simazine | |
| | | | simetryne | |
| | | | terbumeton | |
| | | | terbuthylazine | |
| | | | terbutryne | |
| | | | trietazine | |
| | | Triazinone | hexazinone | |
| | | | metamitron | |
| | | | metribuzin | |
| | | Triazolinone | amicarbazone | |
| | | Uracil | bromacil | |
| | | | lenacil | |
| | | | terbacil | |
| | | Pyridazinone | pyrazon = chloridazon | |
| | | Phenyl-carbamate | desmedipham | |
| | | | phenmedipham | |
| C2 | Inhibition of photosynthesis at photosystem II | Urea | chlorbromuron | 7 |
| | | | chlorotoluron | |
| | | | chloroxuron | |
| | | | dimefuron | |
| | | | diuron | |
| | | | ethidimuron | |
| | | | fenuron | |
| | | | fluometuron (see F3) | |
| | | | isoproturon | |
| | | | isouron | |
| | | | linuron | |
| | | | methabenzthiazuron | |

| HRAC Group | Mode of Action | Chemical Family | Active Ingredient | WSSA Group |
|---|---|---|---|---|
| | | | metobromuron | |
| | | | metoxuron | |
| | | | monolinuron | |
| | | | neburon | |
| | | | siduron | |
| | | | tebuthiuron | |
| | | Amide | propanil | |
| | | | pentanochlor | |
| C3 | Inhibition of photosynthesis at photosystem II | Nitrile | bromofenoxim | 6 |
| | | | bromoxynil | |
| | | | ioxynil | |
| | | Benzothiadiazinone | bentazon | |
| | | Phenyl-pyridazine | pyridate | |
| | | | pyridafol | |
| D | Photosystem-I-electron diversion | Bipyridylium | diquat | 22 |
| | | | paraquat | |
| E | Inhibition of protoporphyrinogen oxidase (PPO) | Diphenylether | acifluorfen-Na | 14 |
| | | | bifenox | |
| | | | chlomethoxyfen | |
| | | | fluoroglycofen-ethyl | |
| | | | fomesafen | |
| | | | halosafen | |
| | | | lactofen | |
| | | | oxyfluorfen | |
| | | Phenylpyrazole | fluazolate | |
| | | | pyraflufen-ethyl | |
| | | N-phenylphthalimide | cinidon-ethyl | |
| | | | flumioxazin | |
| | | | flumiclorac-pentyl | |
| | | Thiadiazole | fluthiacet-methyl | |
| | | | thidiazimin | |
| | | Oxadiazole | oxadiazon | |
| | | | oxadiargyl | |
| | | Triazolinone | azafenidin | |
| | | | carfentrazone-ethyl | |
| | | | sulfentrazone | |
| | | Oxazolidinedione | pentoxazone | |
| | | Pyrimidindione | benzfendizone | |
| | | | butafenacil | |
| | | Other | pyraclonil | |
| | | | profluazol | |
| | | | flufenpyr-ethyl | |
| F1 | Bleaching: Inhibition of carotenoid biosynthesis at the phytoene desaturase step (PDS) | Pyridazinone | norflurazon | 12 |
| | | Pyridinecarboxamide | diflufenican | |
| | | | picolinafen | |
| | | Other | beflubutamid | |
| | | | fluridone | |
| | | | flurochloridone | |
| | | | flurtamone | |
| F2 | Bleaching: Inhibition of 4-hydroxyphenyl-pyruvate-dioxygenase (4-HPPD) | Triketone | mesotrione | 27 |
| | | | sulcotrione | |
| | | Isoxazole | isoxachlortole | |
| | | | isoxaflutole | |
| | | Pyrazole | benzofenap | |
| | | | pyrazolynate | |
| | | | pyrazoxyfen | |
| | | Other | benzobicyclon | |
| F3 | Bleaching: Inhibition of carotenoid biosynthesis (unknown target) | Triazole | amitrole (in vivo inhibition of lycopene cyclase | 11 |
| | | Isoxazolidinone | clomazone | 13 |
| | | Urea | fluometuron (see C2) | |
| | | Diphenylether | aclonifen | |

-continued

| HRAC Group | Mode of Action | Chemical Family | Active Ingredient | WSSA Group |
|---|---|---|---|---|
| G | Inhibition of EPSP synthase | Glycine | glyphosate sulfosate | 9 |
| H | Inhibition of glutamine synthetase | Phosphinic acid | glufosinate-ammonium bialaphos = bilanaphos | 10 |
| I | Inhibition of DHP (dihydropteroate) synthase | Carbamate | asulam | 18 |
| K1 | Microtubule assembly inhibition | Dinitroaniline | benefin = benfluralin butralin dinitramine ethalfluralin oryzalin pendimethalin trifluralin | 3 |
| | | Phosphoroamidate | amiprophos-methyl butamiphos | |
| | | Pyridine | dithiopyr thiazopyr | |
| | | Benzamide | propyzamide = pronamide tebutam | |
| | | Benzoic acid | DCPA = chlorthal-dimethyl | |
| K2 | Inhibition of mitosis/ microtubule organisation | Carbamate | chlorpropham propham carbetamide | 23 |
| K3 | Inhibition of VLCFAs (Inhibition of cell division) | Chloroacetamide | acetochlor alachlor butachlor dimethachlor dimethanamid metazachlor metolachlor pethoxamid pretilachlor propachlor propisochlor thenylchlor | 15 |
| | | Acetamide | diphenamid napropamide naproanilide | |
| | | Oxyacetamide | flufenacet mefenacet | |
| | | Tetrazolinone | fentrazamide | |
| | | Other | anilofos cafenstrole piperophos | |
| L | Inhibition of cell wall (cellulose) synthesis | Nitrile | dichlobenil chlorthiamid | 20 |
| | | Benzamide | isoxaben | 21 |
| | | Triazolocarboxamide | flupoxam | |
| | | Quinoline carboxylic acid | quinclorac (for monocots) (also group O) | 26 |
| M | Uncoupling (Membrane disruption) | Dinitrophenol | DNOC dinoseb dinoterb | 24 |
| N | Inhibition of lipid synthesis - not ACCase inhibition | Thiocarbamate | butylate cycloate dimepiperate EPTC esprocarb molinate orbencarb pebulate prosulfocarb thiobencarb = benthiocarb tiocarbazil triallate vernolate | 8 |

-continued

| HRAC Group | Mode of Action | Chemical Family | Active Ingredient | WSSA Group |
|---|---|---|---|---|
| | | Phosphorodithioate | bensulide | |
| | | Benzofuran | benfuresate | |
| | | | ethofumesate | |
| | | Chloro-Carbonic-acid | TCA | 26 |
| | | | dalapon | |
| | | | flupropanate | |
| O | Action like indole acetic acid (synthetic auxins) | Phenoxy-carboxylic-acid | clomeprop | 4 |
| | | | 2,4-D | |
| | | | 2,4-DB | |
| | | | dichlorprop = 2,4-DP | |
| | | | MCPA | |
| | | | MCPB | |
| | | | mecoprop = MCPP = CMPP | |
| | | Benzoic acid | chloramben | |
| | | | dicamba | |
| | | | TBA | |
| | | Pyridine carboxylic acid | clopyralid | |
| | | | fluroxypyr | |
| | | | picloram | |
| | | | triclopyr | |
| | | Quinoline carboxylic acid | quinclorac (also group L) | |
| | | | quinmerac | |
| | | Other | benazolin-ethyl | |
| P | Inhibition of auxin transport | Phthalamate | naptalam | 19 |
| | | Semicarbazone | diflufenzopyr-Na | |
| Z | Unknown (actual mode of action unknown, but likely that they differ in mode of action between themselves and from other groups) | Arylaminopropionic acid | Flamprop-M-methyl/-isopropyl | 25 |
| | | Pyrazolium | difenzoquat | 26 |
| | | Organoarsenical | DSMA | 17 |
| | | | MSMA | |
| | | Other | bromobutide | 27 |
| | | | (chloro)-flurenol | |
| | | | cinmethylin | |
| | | | cumyluron | |
| | | | dazomet | |
| | | | dymron = daimuron | |
| | | | methyl-dimuron = methyl-dymron | |
| | | | etobenzanid | |
| | | | fosamine | |
| | | | indanofan | |
| | | | metam | |
| | | | oxaziclomefone | |
| | | | oleic acid | |
| | | | pelargonic acid | |
| | | | pyributicarb | |

Herbicides can be classified by their mode of action and/or site of action and can also be classified by the time at which they are applied (e.g., pre-emergent or post-emergent), by the method of application (e.g., foliar application or soil application), or by how they are taken up by or affect the plant. Mode of action generally refers to the metabolic or physiological process within the plant that the herbicide inhibits or otherwise impairs, whereas site of action generally refers to the physical location or biochemical site within the plant where the herbicide acts or directly interacts. Herbicides can be classified in various ways, including by mode of action and/or site of action. Often, a herbicide-tolerance gene that confers tolerance to a particular herbicide or other chemical on a plant expressing it will also confer tolerance to other herbicides or chemicals in the same class or subclass, for example, a class or subclass set forth in the table above. Thus, in some examples, a transgenic plant is tolerant to more than one herbicide or chemical in the same class or subclass, such as, for example, an inhibitor of PPO, a sulfonylurea, or a synthetic auxin. In some examples the plant is transgenic for one or more of the herbicide tolerance traits, non-transgenic for one of more of the tolerance traits, or any combination thereof.

Typically, the plants provided can tolerate treatment with different types of herbicides (i.e., herbicides having different modes of action and/or different sites of action) as well as with higher amounts of herbicides than previously known plants, thereby permitting improved weed management strategies that are recommended in order to reduce the incidence and prevalence of herbicide-tolerant weeds. Specific herbicide combinations can be employed to effectively control weeds.

A transgenic crop plant which can be selected for use in crop production based on the prevalence of herbicide-tolerant weed species in the area where the transgenic crop is to be grown is provided. Methods are known in the art for assessing the herbicide tolerance of various weed species. Weed management techniques are also known in the art, such as for example, crop rotation using a crop that is tolerant to a herbicide to which the local weed species are not tolerant. A number of entities monitor and publicly report the incidence and characteristics of herbicide-tolerant weeds, including the Herbicide Resistance Action Committee (HRAC), the Weed Science Society of America, and various state agencies (see, e.g., herbicide tolerance scores for various broadleaf weeds from the 2004 Illinois Agricultural Pest Management Handbook), and one of skill in the art would be able to use this information to determine which crop and herbicide combinations should be used in a particular location.

These entities also publish advice and guidelines for preventing the development and/or appearance of and controlling the spread of herbicide tolerant weeds (see, e.g., Owen and Hartzler (2004), 2005 Herbicide Manual for Agricultural Professionals, Pub. WC 92 Revised (Iowa State University Extension, Iowa State University of Science and Technology, Ames, Iowa); Weed Control for Corn, Soybeans, and *Sorghum, Chapter* 2 of "2004 Illinois Agricultural Pest Management Handbook" (University of Illinois Extension, University of Illinois at Urbana-Champaign, Ill.); Weed Control Guide for Field Crops, MSU Extension Bulletin E434 (Michigan State University, East Lansing, Mich.)).

Also included are plant cells, plants, and/or seeds produced by any of the foregoing methods.

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLES

Example 1

Identification of Sulfentrazone Tolerant and Sensitive Soybean Lines—Herbicide Screening Bioassay and Intergroup Association Marker Based Diagnostic Sulfentrazone is a PPO inhibitor and is the active ingredient in Authority® herbicide. Authority® 75DF (FMC Corp., Philadelphia, Pa., USA) is a 75% active ingredient formulation of sulfentrazone containing no other active ingredients.
Part 1: Herbicide Bioassay
One hundred sixteen (116) elite soybean lines were screened for sulfentrazone tolerance using the following protocol. Seed of soybean varieties with adequate seed quality, having greater than 85% warm germination were used.
Design and Replication:
After planting, entries were set up in a randomized complete block design, blocked by replication. Three replications per experiment were used. One or more of well established check variety were included in the experiment, such as available public sector check lines.

| | |
|---|---|
| Non-tolerant check: | Pioneer 9692, Asgrow A4715 |
| Tolerant check: | Pioneer 9584, Syngenta S5960 |

Growing conditions were as follows (greenhouse/growth chamber): 16 hr photoperiod @ 85° F. (w/75° nighttime set back). Lighting is critical to the success of the screening as stated below.
Method of Screening:
Four inch plastic pots were filled with a high quality universal potting soil. Entries were planted 1 inch deep at the rate of 5 seeds/pot. A bar-coded plastic stake was used to identify each entry. After planting the pots were allowed to sit in greenhouse overnight to acclimate to soil and improve germination. The following day a sulfentrazone herbicide solution was slowly poured over each pot and allowed to evenly soak through entire soil profile. This ensured that each seed was exposed to an equal amount of sulfentrazone. Pots were placed on aluminum trays and placed in a greenhouse or growth chamber under high intensity light conditions with photosynthetic photon flux density (PPFD) of at least 500 mmol/m/s. Proper lighting conditions were necessary for this screening due to the nature of the PPO inhibitor used. Pots were lightly watered so that herbicide was not leached from the soil profile. After soybean emergence the pots were watered by keeping aluminum trays filled with ¾" of water under each pot.
Herbicide Solution:
A) Mix a stock solution of 0.926 g Authority® 75DF (FMC Corp.), thoroughly dissolved in 1000 ml of water.
B) Mix 10 ml of STOCK SOLUTION in 1000 ml of water to create final solution.
C) Pour 100 ml of FINAL SOLUTION over each pot.
Recording Data:
10-14 days after treatment, plants were ready to be scored. All scores were based on a comparison to the checks and evaluated as follows:
  9=Equivalent or better when compared to the tolerant check
  7=Very little damage or response noted.
  5=Intermediate response or damage
  3=Major damage, including stunting and foliar necrosis
  1=Severe damage, including severe stunting and necrosis; equivalent or worse when compared to the non-tolerant check Of the 116 soybean lines screened, 102 showed at least some tolerance to sulfentrazone based herbicides and 11 showed high sensitivity. A reference relevant to this protocol would be: Dayan et al. (1997) 'Soybean (*Glycine max*) cultivar differences in response to sulfentrazone' Weed Science 45:634-641.
Part 2: Intergroup Analysis
An "Intergroup Allele Frequency Distribution" analysis was conducted using GeneFlow™ version 7.0 software. An intergroup allele frequency distribution analysis provides a method for finding non-random distributions of alleles between two phenotypic groups.

During processing, a contingency table of allele frequencies was constructed and from this a G-statistic and probability were calculated. The G statistic was adjusted by using the William's correction factor. The probability value was adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the tolerance phenotype and the marker will co-segregate. A more complete discussion of the derivation of the probability values can be found in the GeneFlow™ version 7.0 software documentation. See also Sokal and Rolf (1981), Biometry:

The Principles and Practices of Statistics in Biological Research, 2nd ed., San Francisco, W.H. Freeman and Co.

The underlying logic is that markers with significantly different allele distributions between the tolerant and non-tolerant groups (i.e., non-random distributions) might be associated with the trait and can be used to separate them for purposes of marker assisted selection of soybean lines with previously uncharacterized tolerance or non-tolerance to protoporphyrinogen oxidase inhibitors. The present analysis examined one marker locus at a time and determined if the allele distribution within the tolerant group is significantly different from the allele distribution within the non-tolerant group. A statistically different allele distribution is an indication that the marker is linked to a locus that is associated with tolerance or non-tolerance to protoporphyrinogen oxidase inhibitors. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In this analysis, 1043 marker loci had enough observations for analysis.

This analysis compares the plants' phenotypic score with the genotypes at the various loci. This type of intergroup analysis neither generates nor requires any map data. Subsequently, map data (for example, a composite soybean genetic map) is relevant in that multiple significant markers that are also genetically linked can be considered as collaborating evidence that a given chromosomal region is associated with the trait of interest.

Results

Table 1 below provides a table listing the soybean markers that demonstrated linkage disequilibrium with the tolerance to protoporphyrinogen oxidase inhibitor phenotype. There were 1043 markers used in this analysis. Also indicated in that table are the chromosomes on which the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the Adjusted Probability values. Out of 584 loci studied in 38 sensitive and 160 tolerant soybean lines, QTLs on Lg L and on Lg N were highly significant, as shown in the table below.

TABLE 1

Intergroup analysis results for LgL and LgN markers

| Locus | Test | Chrom# | Position | G-value | df | Prob (G) | Adj Prob |
|---|---|---|---|---|---|---|---|
| S00224-1 | GW | L | 12.03 | 89.87 | −1 | 0 | 0 |
| P10649C-3 | ASH | L | 3.6 | 86.01 | −1 | 0 | 0 |
| SATT523 | SSR | L | 32.4 | 24.02 | −1 | 0.000001 | 0.000592 |
| S60167-TB | SSR | N | 26 | 62.35 | −1 | 0 | 0 |
| P5467A-1 | ASH | N | 25 | 16.25 | −1 | 0.000056 | 0.032192 |
| P5467A-2 | ASH | N | 25 | 16.2 | −1 | 0.000057 | 0.032731 |

Table 2 below shows the allele distribution between 101 tolerant lines and 32/33 non-tolerant lines analyzed. Lines exhibiting tolerance are indicated in the first column as "TOL," and lines exhibiting non-tolerance are indicated in the first column as "NON." Marker calls for the P10649C-3 locus and the S60167-TB locus were available for 132 and 63 of the lines respectively.

TABLE 2

| | Allele distribution | |
|---|---|---|
| Phenotype | P10649C-3 allele LG-L | S60167-TB allele LG-N |
| TOL | 1 | 1 |
| TOL | 1 | 1 |
| TOL | 1 | |
| TOL | 1 | |
| TOL | 1 | |
| TOL | 1 | 2 |
| TOL | 1 | |
| TOL | 1 | |
| TOL | 1 | 1 |
| TOL | 1 | |
| TOL | 1 | 1 |
| TOL | 1 | |
| TOL | 1 | 1 |
| TOL | 1 | 1 |
| TOL | 1 | 1 |
| TOL | 1 | 1 |
| TOL | 1 | |
| TOL | 1 | 1 |
| TOL | 1 | |
| TOL | 1 | |
| TOL | 1 | 1 |
| TOL | 1 | 1 |
| TOL | 1 | |
| TOL | 1 | 1 |
| TOL | 1 | 1 |
| TOL | 1 | 1 |
| TOL | 1 | |
| TOL | 1 | 1 |
| TOL | 1 | 1 |
| TOL | 1 | |
| TOL | 1 | |
| TOL | 1 | 1 |
| TOL | 1 | 1 |
| TOL | 1 | |
| TOL | 1 | 1 |
| TOL | 1 | |
| TOL | 1 | |
| TOL | 1 | 1 |
| TOL | 1 | 1 |
| TOL | 1 | 1 |
| TOL | 1 | 1 |
| TOL | 1 | |
| TOL | 1 | 1 |
| TOL | 1 | 1 |
| TOL | 1 | |
| TOL | 1 | 1 |
| TOL | 1 | 1 |
| TOL | 1 | |
| TOL | 1 | |
| TOL | 1 | 1 |
| TOL | 1 | 1 |
| TOL | 1 | 1 |
| TOL | 1 | 1 |
| TOL | 1 | |
| TOL | 1 | |
| TOL | 1 | 1 |
| TOL | 1 | 1 |
| TOL | 1 | |
| TOL | 1 | |
| TOL | 1 | |
| TOL | 1 | |
| TOL | 1 | |
| TOL | 1 | 1 |
| TOL | 1 | |
| TOL | 1 | 1 |
| TOL | 1 | 1 |

TABLE 2-continued

| Phenotype | P10649C-3 allele LG-L | S60167-TB allele LG-N |
|---|---|---|
| TOL | 1 | |
| TOL | 1 | |
| TOL | 1 | |
| TOL | 1 | |
| TOL | 1 | 1 |
| TOL | 1 | |
| TOL | 1 | |
| TOL | 1 | |
| TOL | 1 | |
| TOL | 1 | 1 |
| TOL | 1 | 1 |
| TOL | 1 | 1 |
| TOL | 1 | |
| TOL | 1 | |
| TOL | 1 | 1 |
| TOL | 1 | |
| TOL | 1 | |
| TOL | 1 | |
| TOL | 1 | |
| TOL | 1 | |
| TOL | 1 | |
| TOL | 1 | |
| TOL | | |
| TOL | 1 | |
| TOL | 1 | |
| TOL | 2 | 2 |
| TOL | 1 | |
| TOL | 1 | |
| TOL | 1 | |
| NON | 3 | 2 |
| NON | 3 | |
| NON | 1 | 1 |
| NON | 1_2 | 2 |
| NON | 3 | 2 |
| NON | 3 | |
| NON | 1 | 1_2 |
| NON | 3 | 2 |
| NON | 2 | 1_2 |
| NON | 3 | 2 |
| NON | 2 | |
| NON | 2 | 2 |
| NON | 2 | 2 |
| NON | 1 | 1 |
| NON | 2_3 | |
| NON | 3 | 2 |
| NON | 3 | 2 |
| NON | 2_3 | |
| NON | 3 | |
| NON | 3 | |
| NON | 1 | 1 |
| NON | 2 | |
| NON | 3 | |
| NON | 3 | 2 |
| NON | 3 | |
| NON | 2 | 2 |
| NON | 3 | 2 |
| NON | 1_3 | 2 |
| NON | 3 | |
| NON | 2 | |
| NON | 1 | |
| NON | 3 | |

The non-random distribution of alleles between the tolerant and non-tolerant plant groups at the marker loci in Table 2 is good evidence that a QTL influencing tolerance to protoporphyrinogen oxidase inhibitors is linked to these marker loci.

Example 2

Predication and Confirmation of Marker Based Selection for Response to PPO Chemistries in a Set of Diverse Public Soybean Lines Marker haplotype data for a set of 17 diverse public soybean lines was determined for two QTL identified in Example 1 for Linkage Group L molecular markers P10649C-3 (approximate position 3.6) and S00224-1 (approximate position 12.0). The response of these lines to sulfentrazone herbicide was published by Hulting et al. (Soybean (*Glycine max* (L.) Merr.) cultivar tolerance to sulfentrazone. 2001 Science Direct, Vol. 20(8): 679-683). The phenotypic response was reported as a growth reduction index: plant height and visual injury as expressed as a percentage of check plot of each cultivar. Data for the marker haplotype on Linkage Group L and the herbicide bioassay results are presented in Table 3. Use of the molecular diagnostic P10649C-3 (linked QTL on Linkage Group L, approximate position 3.6) for this set of phentoyped soybean lines is 92% predictive of tolerance to sulfentrazone when injury is set at 39% or less GRI and is 100% predictive of non-tolerance to sulfentrazone when injury is set at 40% or higher GRI. Use of the S00224-1 marker (approximate position 12.0) for this set of soybean lines is 88% predictive of tolerance to sulfentrazone when injury is set at 39% or less GRI and is 100% predictive of non-tolerance to sulfentrazone when injury is set at 40% or more GRI.

TABLE 3

Marker haplotype at/near QTL on Linkage Group L for PPO herbicide (sulfentrazone) response and phenotypic measure of crop response, expressed in terms of Growth Reduction Index, for soybean cultivars (italicized items indicate deviations from expected)

| Cultivar | Growth Reduction Index* | Linkage Group L QTLs Position 3.6 P10649C-3 | Position 12.0 S00224-1 |
|---|---|---|---|
| PI88788 | 2 | 1, 1 | 3, 3 |
| Richland | 4 | 1, 1 | 3, 3 |
| Lincoln | 5 | 1, 1 | 3, 3 |
| PI180501 | 8 | 1, 1 | 3, 3 |
| Illini | 8 | 1, 1 | 3, 3 |
| S100 | 8 | 1, 1 | 3, 3 |
| Mukden | 8 | 1, 1 | 3, 3 |
| Arksoy | 10 | 1, 1 | 3, 3 |
| Capital | 10 | 1, 1 | 3, 3 |
| Haberlandt | 10 | *3, 3* | *2, 2* |
| Ralsoy | 13 | 1, 1 | *2, 3* |
| Dunfield | 16 | 1, 1 | 3, 3 |
| Peking | 22 | 1, 1 | 3, 3 |
| Roanoke | 40 | 3, 3 | 2, 2 |
| Ogden | 42 | 3, 3 | 2, 2 |
| Hutcheson | 46 | 3, 3 | 2, 2 |
| Ransom | 52 | 3, 3 | 2, 2 |
| allele call load percent accuracy correct tolerant | | (alleles 1) 24/26 = 92% | (allele 3) 23/26 = 88% |
| correct non-tolerant | | (allele 3) 8/8 = 100% | (allele 2) = 8/8 = 100% |

*growth reduction index (plant height and visual injury as expressed as a percentage of check plot of each cultivar);
Pre-emergence sulfentrazone application of 0.28 kg ai/ha, from Hulting, et al. (supra)

Haplotype data for a set of 15 diverse public soybean lines was determined for two QTL identified in Example 1 for Linkage Group N molecular marker S60167 (approximate position 26.0). The response of these 15 lines to sulfentrazone herbicide was determined and published upon by Hulting et al. (Soybean (*Glycine max* (L.) Merr.) cultivar tolerance to sulfentrazone. 2001 Science Direct, Vol. 20(8): 679-683). The phenotypic response was reported as a growth reduction index: plant height and visual injury as expressed as a percentage of check plot of each cultivar. Data for the marker haplotype on Linkage Group N and the herbicide bioassay results are presented in Table 4. The cultivar Ralsoy is heterozygous for the 560167 marker. Use of the 560167 marker for this set of phentoyped soybean lines is 88% predictive of tolerance to sulfentrazone when injury is set at 39% or less GRI and is 100% predictive of tolerance to sulfentrazone when injury is set at 40% or higher GRI.

TABLE 4

Marker haplotype at/near QTL on Linkage Group N for PPO herbicide (sulfentrazone) response and phenotypic measure of crop response, expressed in terms of Growth Reduction Index, for soybean cultivars (italicized items indicate deviations from expected)

| Cultivar | Growth Reduction Index* | Linkage Group N QTL Position 26 S60167-TB |
|---|---|---|
| PI88788 | 2 | 1, 1 |
| Richland | 4 | 1, 1 |
| Lincoln | 5 | 1, 1 |
| Illini | 8 | 1, 1 |
| S100 | 8 | 1, 1 |
| Mukden | 8 | 1, 1 |
| Arksoy | 10 | 1, 1 |
| Haberlandt | 10 | 1, 1 |
| Ralsoy | 13 | 1, *2* |
| Dunfield | 16 | 1, 1 |
| CNS | 20 | *2, 2* |
| Peking | 22 | 1, 1 |
| Roanoke | 40 | 2, 2 |
| Ogden | 42 | 2, 2 |
| Hutcheson | 46 | 2, 2 |
| allele call load percent accuracy | | |
| correct tolerant | (allele 1) | 21/24 = 88% |
| correct non-tolerant | (allele 2) | 6/6 = 100% |

Example 3

Predication and Confirmation of Marker Based Selection For Response to PPO Chemistries in a Set of Soybean Commercial Lines Haplotype data for a set of 7 commercial soybean lines was determined for two QTL identified in the previous example for Linkage Group L molecular markers P10649C-3 (position 3.6) and S00224-1 (position 12.0). The response of these lines to sulfentrazone herbicide was determined by method used in Example 1. In addition, the same scale was used for scoring such that:

9=Equivalent or better when compared to the tolerant check
7=Very little damage or response noted.
5=Intermediate response or damage
3=Major damage, including stunting and foliar necrosis
1=Severe damage, including severe stunting and necrosis; equivalent or worse when compared to the non-tolerant check Data for the marker haplotype on Linkage Group L and the herbicide bioassay results are presented in Table 5. Use of either/both of these markers for this set of phentoyped soybean lines is 100% predictive of both tolerance (score of a 7 or 9) and non-tolerance (score of a 1 for the non-tolerant check).

TABLE 5

Prediction and confirmation of marker based selection at QTL for linkage group L for response to PPO chemistry (sulfentrazone) in a set of commercial soybean varieties.

| Variety | sulfentrazone injury score | Position 3.6 P10649C-3 | Position 12.0 S00224-1 |
|---|---|---|---|
| 93B41 | 9 | 1, 1 | 3, 3 |
| 93B82 | 9 | 1, 1 | 3, 3 |
| 9281 | 9 | 1, 1 | 3, 3 |
| 9584 | 9 | 1, 1 | 3, 3 |
| 92B52 | 7 | 1, 1 | 3, 3 |
| 92B61 | 7 | 1, 1 | 3, 3 |
| 9692 | 1 | 3, 3 | 2, 2 |

Example 4

Predication and Confirmation of Marker Based Selection for Response to PPO Chemistries (Sulfentrazone) in Ten Lines from a Set of Soybean Lines Phenotyped at the University of Illinois A comparison for the marker predictiveness of PPO response was conducted. The herbicide bioassay experiment used is described in Phytoxic Response and Yield of Soybean (*Glycine max*) Varieties Treated with Sulfentrazone or Flumioxazin (Taylor-Lovell et al., 2001 Weed Technology 15:96-102). Phenotypic data was taken from Table 2 of the publication for those varieties for which in-house marker data was available. Phenotypic score and haplotype data for a set of 10 soybean lines (1 public and 9 commercial) in the chromosomal regions around the QTL for Linkage group L is presented in Table 6. The phenotypic score was determined as percent injury which is defined as visible injury ratings including stunting, chlorosis, and bronzing symptomology (0=no injury; 100=complete death) with 448 g ai/ha field application. Ratings were taken 12 days after treatment. Use of marker P10649C (linked QTL on Linkage Group L, approximate position 3.6, allele call 1) for this set of phentoyped soybean lines is 100% predictive of tolerance (allele call 1) to sulfentrazone when injury is 21% or less and is 100% predictive of non-tolerance (allele call 2 or 3) to sulfentrazone when injury is 43% or greater. The predictiveness of marker S00224-1 is also 100% accurate for tolerance (allele 3) and non-tolerance (allele 2) for this set of material.

TABLE 6

Marker haplotype at/near QTL on Linkage Group L for PPO herbicide (sulfentrazone) response and phenotypic measure of crop injury

| Variety | sulfentrazone injury score | Position 3.6 P10649C-3 | Position 12.0 S00224-1 |
|---|---|---|---|
| P9584 | 5 | 1, 1 | 3, 3 |
| P9671 | 5 | 1, 1 | 3, 3 |
| P9151 | 8 | 1, 1 | 3, 3 |
| P9306 | 15 | 1, 1 | 3, 3 |
| Elgin | 18 | 1, 1 | 3, 3 |
| P9282 | 19 | 1, 1 | 3, 3 |
| P9352 | 21 | 1, 1 | 3, 3 |

TABLE 6-continued

Marker haplotype at/near QTL on Linkage Group L for PPO herbicide (sulfentrazone) response and phenotypic measure of crop injury

| Variety | sulfentrazone injury score | Position 3.6 P10649C-3 | Position 12.0 S00224-1 |
|---|---|---|---|
| P9362 | 43 | 2, 2 | 2, 2 |
| 91B01 | 58 | 3, 3 | 2, 2 |
| P9552 | 61 | 3, 3 | 2, 2 |
| LSD (0.05) | 8 | | |
| allele call load percent accuracy correct tolerant | | (alleles 1 or 2) 14/14 = 100% | (allele 3) 14/14 = 100% |
| correct non-tolerant | | (allele 3) 8/8 = 100% | (allele 2) = 8/8 = 100% |

Example 5

Figure 6:
FIG. 6 provides an example of cultivars with vastly different protoporphyrinogen oxidase (PPOase) inhibitor tolerance phenotypes. Shown are greenhouse samples, with a non-tolerant variety with non-tolerant (arrow, left side) and tolerant (right side) variety checks, showing treated plants in the foreground, and untreated plants in the background.

Pictures of Soybean Variety Response (Tolerant and Non-Tolerant Check Varieties) to Sulfentrazone Injury in the Field and in the Greenhouse/Growth Chamber Bioassay Known non-tolerant (i.e., Pioneer variety 9692, Asgrow variety A4715) and tolerant (i.e., Pioneer variety 9584, Syngenta variety S5960) germplasm can exhibit severe differences in symptomology when field conditions are conducive to damage and when lab conditions for bioassays are optimized for selection purposes. FIGS. 5 and 6 show these differences in phenotype. FIG. 5 shows a field sample, with a non-tolerant variety on the left (stunted, necrotic) and tolerant variety on the right (normal growth). FIG. 6 shows a greenhouse sample, with non-tolerant (left side) and tolerant (right side) variety checks, treated in the foreground, untreated in the background.

Example 6

Fine Mapping of PPO Herbicide Tolerance QTL

The PPO herbicide tolerance QTL was mapped in two mapping populations, GEID1653063×GEID3495695 and GEID4520632×GEID7589905 PPO tolerance mapped to chromosome GM19 (LG-L) near the closely linked marker S03859-1-A, which explains 80% of the phenotypic variation. From these two populations, lines with recombination breakpoints near S03859-1-A were identified to define the borders of the QTL and to facilitate fine-mapping.

Subsequent analysis of the recombinants indicated that the closely linked marker S03859-1-A was actually the left flanking marker. The GEID1653063×GEID3495695 population had 37 recombinants that set the flanking markers for the PPO QTL as S04867-1-A (GM19: 841543-841958) and S03859-1-A (GM19: 1634882-1635399) (Table 10). The GEID4520632×GEID7589905 population had 42 recombinants that delimit the QTL to the same interval (Table 11).

Because S03859-1-A was determined to be closely linked to the PPO QTL, annotated loci in the vicinity of this marker were targeted for SNP discovery and marker development. Primers were designed from target loci using Primer3 and checked for uniqueness using bioinformatics software. A panel composed of 20 PPO tolerant and 8 PPO susceptible lines, including the four mapping parents from the mapping population, was re-sequenced at the target loci to identify informative SNPs. DNA was extracted using the urea extraction protocol below and PCR amplified using standard lab protocols (see Tables 7-8). The PCR was then cleaned up using the ExoSAP-IT® protocol (USB-Cleveland, Ohio, USA) (Table 9) before being sequenced by Sanger sequencing.

In total, 104 loci were re-sequenced and 235 informative SNPs were identified. From these SNPs, 22 Taqman® probe markers were designed to distinguish between tolerant versus susceptible alleles in the mapping populations. Taqman® assays were designed generally following ABI suggested parameters. These markers were then run on the recombinants from the two mapping populations to facilitate fine-mapping and to further delimit the PPO QTL interval.

Urea Extraction Protocol

1. Grind 2 g fresh tissue or 0.5 g lyophilized tissue and add it to 6 mL Urea Extraction Buffer and mix well.
2. Add RNase A (100 mg/mL) and incubate @ 37° C. for 20 min.
   a. 3 uL—Leaf
   b. 12 uL—Seed
3. Add 4-5 mL Phenol:Chloroform:Isoamyl 25:24:1. Mix well. (Sigma P3803)
4. Put on rocker inside hood.
   a. Fresh—15 min
   b. Lyophilized—30 min
5. Centrifuge @ 8000 rpm at 10° C. for 10 min.
6. Transfer supernatant to clean tube.
7. Add 700 uL of 3M NaOAC (pH 5.0) and 5 mL cold isopropanol. Mix well.
8. Hook DNA and wash in 70% EtOH.
9. Repeat 70% wash.
10. Transfer pellet to 1.5 mL tube and allow to dry.
11. Dissolve pellet in 1 mL 10 mM Tris.

| 7M Urea Extraction Buffer | |
|---|---|
| Water | 350 mL |
| Urea | 336 g |
| 5M NaCl | 50 mL (14.61 g) |
| 1M Tris | 40 mL (pH 8.0) |
| .5M EDTA | 32 mL (pH 8.0) |
| 20% Sarcosine Sol. | 40 mL (8 g) |

Adjust volume to 800 mL with ddH2O

TABLE 7

PCR Reaction Mix for SNP Discovery.

| | 1X (uL) | 24 plate (ul) | 36 plate (uL) | 48 plate (uL) |
|---|---|---|---|---|
| gDNA (~50-100 ng) | 2.0 | — | — | — |
| 10x PCR Buffer | 2.0 | 5,952 | 7,680 | 10,944 |
| 1 mM dNTP | 2.0 | 5,952 | 7,680 | 10,944 |
| Taq | 0.1 | 297.6 | 384 | 547.2 |
| 0.5 uM Primer (F + R) | 4.0 | — | — | — |
| ddH2O | 9.9 | 29,462 | 38,016 | 54,173 |
| Total | 20.0 | 41,664 | 53,760 | 76,608 |

TABLE 8

PCR Setup for SNP Discovery.
Dipper Setup

| PCR conditions | Temp | Time | # Cycles |
|---|---|---|---|
| initial denature | 94 C. | 3 min | 1X |
| denature | 94 C. | 45 sec | 35X |
| anneal | 65 C. | 60 sec | |
| extension | 72 C. | 75 sec | |
| final extension | 72 C. | 5 min | 1X |
| end | | | |

TABLE 9

Exo/SAP Protocol for PCR clean up.
PCR clean up Exo/SAP Mix (pre-sequencing)
add 3.6 ul of mastermix to 7 μl final PCR product

| | 24 plate (μl) | 36 plate (μl) | 48 plate (μl) |
|---|---|---|---|
| ddH2O | 4,285.4 | 5,944.3 | 7,326.7 |
| SAP | 4,285.4 | 5,944.3 | 7,326.7 |
| Exo | 2,142.7 | 2,972.2 | 3,663.4 |
| total | 10,714 | 14,861 | 18,317 |

TABLE 10

Initial recombinants identified from GEID1653063 × GEID3495695 mapping population that delimited PPO herbicide tolerance QTL to interval between S01659-1-A and S03859-1-A.

| SAMPLE | S04867-1-A | S03859-1-A | Call | Average | Comment |
|---|---|---|---|---|---|
| Genetic Pos | 12.55 | 16.08 | | | |
| GEID1653063 | A | A | SUS | 1 | Control |
| GEID3495695 | B | B | TOL | 9 | Control |
| SJ22185567 | A | B | TOL | 9 | L border |
| SJ22185980 | A | B | TOL | 9 | L border |
| SJ22186045 | A | B | TOL | 9 | L border |
| SJ22186929 | A | B | TOL | 9 | L border |
| SJ22186019 | B | H | TOL | 9 | R border |
| SJ22185608 | H | B | TOL | 9 | L border |
| SJ22186913 | H | B | TOL | 9 | L border |
| SJ22185928 | H | B | TOL | 9 | L border |
| SJ22186923 | H | B | TOL | 8.333333 | L border |
| SJ22185569 | A | H | SEG | 5 | L border |
| SJ22186052 | A | H | SEG | 6.333333 | L border |
| SJ22186882 | A | H | SEG | 5 | L border |
| SJ22186919 | B | H | SEG | 5.666667 | L border |
| SJ22186968 | B | H | SEG | 6.333333 | L border |
| SJ22186824 | B | H | SEG | 6.333333 | L border |
| SJ22185604 | H | B | SEG | 6.333333 | R border |
| SJ22185573 | H | A | SEG? | 3.666667 | R border |
| SJ22185983 | A | B | SUS | 1 | R border |
| SJ22186894 | A | B | SUS | 2.333333 | R border |
| SJ22185562 | A | H | SUS | 1.666667 | R border |
| SJ22185941 | A | H | SUS | 1 | R border |
| SJ22185534 | B | A | SUS | 3 | L border |
| SJ22185545 | B | A | SUS | 1.666667 | L border |
| SJ22185559 | B | A | SUS | 2.333333 | L border |
| SJ22186023 | B | A | SUS | 3 | L border |
| SJ22186057 | B | A | SUS | 1 | L border |
| SJ22186065 | B | A | SUS | 1 | L border |
| SJ22186837 | B | A | SUS | 3 | L border |
| SJ22185957 | B | A | SUS | 1 | L border |
| SJ22186846 | B | A | SUS | 1.666667 | L border |
| SJ22186840 | H | A | SUS | 1 | L border |
| SJ22186950 | H | A | SUS | 1 | L border |
| SJ22186872 | H | A | SUS | 2.333333 | L border |
| SJ22186836 | H | A | SUS | 1.666667 | L border |
| SJ22186074 | H | A | SUS | 1 | L border |
| SJ22186906 | H | A | SUS | 1 | L border |
| SJ22185984 | H | A | SUS | 1 | L border |

TABLE 11

Initial recombinants identified from GEID4520632 × GEID7589905 mapping population that delimited PPO herbicide tolerance QTL to interval between S04867-1-A and S03859-1-A

| SAMPLE | S04867-1-A | S03859-1-A | Call | Ave | Comment |
|---|---|---|---|---|---|
| Genetic Pos | 12.55 | 16.08 | | | |
| GEID7589905 | A | A | SUS | 1 | Control |
| GEID4520632 | B | B | TOL | 9 | Control |
| SP21669231 | A | B | TOL | 9 | L border |
| SP21669401 | A | B | TOL | 9 | L border |
| SP21669240 | A | B | TOL | 9 | L border |
| SP21669613 | A | B | TOL | 9 | L border |
| SP21669249 | H | B | TOL | 9 | L border |
| SP21669645 | H | B | TOL | 9 | L border |
| SP21669670 | H | B | TOL | 9 | L border |
| SP21669563 | H | B | TOL | 9 | L border |
| SP21669592 | H | B | TOL | 9 | L border |
| SP21669260 | B | A | SUS | 1 | L border |
| SP21669265 | B | A | SUS | 1 | L border |
| SP21669778 | B | A | SUS | 1.666667 | L border |
| SP21669590 | B | A | SUS | 1 | L border |
| SP21669751 | A | H | SUS | 1 | R border |
| SP21669380 | H | A | SUS | 2.666667 | L border |
| SP21669679 | H | A | SUS | 1 | L border |
| SP21669708 | H | A | SUS | 1 | L border |
| SP21669755 | H | A | SUS | 1 | L border |
| SP21669214 | H | A | SUS | 1 | L border |
| SP21669573 | H | A | SUS | 1.666667 | L border |
| SP21669612 | H | A | SUS | 2.333333 | L border |
| SP21669336 | H | A | SUS | 3.666667 | L border |
| SP21669201 | B | H | SEG | 5 | L border |
| SP21669503 | B | H | SEG | 5 | L border |
| SP21669664 | B | H | SEG | 5 | L border |
| SP21669540 | B | H | SEG | 5 | L border |
| SP21669752 | B | H | SEG | 5.666667 | L border |
| SP21669230 | B | H | SEG | 5.666667 | L border |
| SP21669331 | A | H | SEG | 6.333333 | L border |
| SP21669371 | A | H | SEG | 5 | L border |
| SP21669542 | A | H | SEG | 6.333333 | L border |
| SP21669584 | A | H | SEG | 5 | L border |
| SP21669694 | A | H | SEG | 5.666667 | L border |
| SP21669763 | A | H | SEG | 5 | L border |
| SP21669533 | A | H | SEG | 5 | L border |
| SP21669417 | A | H | SEG | 6.333333 | L border |
| SP21669647 | A | H | SEG? | 7.666667 | L border |
| SP21669651 | A | H | SEG? | 7.666667 | L border |
| SP21669541 | H | B | SEG? | 7.666667 | R border |
| SP21669749 | H | A | SEG | 5 | R border |
| SP21669356 | H | A | SEG | 5 | R border |
| SP21669674 | H | A | SEG? | 3.666667 | R border |

From the GEID1653063×GEID3495695 mapping population, four key recombinants were identified which served to further fine-map the PPO QTL interval (Table 13). A recombination breakpoint at S08110-1-Q1 in line SJ22186052 set the left border, while breakpoints at S08105-1-Q1 in SJ22186019, SJ22186894, and SJ22185941 set the right border. These recombinants delimit the PPO QTL to ±70 kb interval. From the GEID4520632×GEID7589905 mapping population, eight key recombinants were identified (Table 14). A recombination breakpoint in line SP21669503 at S08117-1-Q1 set the left border, while breakpoints in SP21669249, SP21669332, SP21669615, SP21669616, SP21669670, SP21669458, and SP21669760 set the right border at S08010-1-Q1. These recombinants delimit the PPO QTL to a ~526 kb interval. However, when the data from these two mapping populations are combined into a single set, the PPO QTL interval is delimited to a ~56 kb interval between S08117-1-Q1 and S08105-1-Q1 (Table 12).

TABLE 12

Summary of SNP markers used for initial QTL mapping and fine-mapping of PPO herbicide tolerance QTL. Combined data from the two populations delimits the QTL to a ~56 kb interval between S08117-1-Q1 and S8105-1-Q1.

| Marker | Amplicon | Loci | First Base Coordinate | Last base coordinate | Population | Fine-mapping | Comment |
|---|---|---|---|---|---|---|---|
| S04867-1-A | | Glyma19g01220.1 | 841543 | 841958 | Both | | |
| S08102-1-Q1 | PPO_Gm19_1487k3-1 | Glyma19g01860.1 | 1489113 | 1489545 | Both | | |
| S08103-1-Q1 | PPO_Gm19_1491k1-1 | X | 1491603 | 1492136 | Both | | |
| S08104-1-Q1 | PPO_Gm19_1491k2-1 | Glyma19g01870.1 | 1492364 | 1492948 | Both | | |
| S08106-1-Q1 | PPO_Gm19_1499k2-1 | Glyma19g01880.1 | 1500732 | 1501392 | GEID1653063/ GEID3495695 | | |
| S08107-1-Q1 | PPO_Gm19_1541k3-1 | Glyma19g01900.1 | 1542880 | 1543693 | GEID1653063/ GEID3495695 | | |
| S08109-1-Q1 | PPO_Gm19_1541k4-1 | Glyma19g01900.1 | 1543868 | 1544588 | GEID1653063/ GEID3495695 | | |
| S08110-1-Q1 | PPO_Gm19_1548k1-1 | Glyma19g01910.1 | 1548367 | 1548822 | GEID1653063/ GEID3495695 | L border GEID1653063/ GEID3495695 | |
| S08111-1-Q1 | PPO_Gm19_1548k2-1 | Glyma19g01910.1 | 1548902 | 1549558 | GEID1653063/ GEID3495695 | | |
| S08115-2-Q1 | PPO_Gm19_1563k1-1 | X | 1563958 | 1564512 | Both | | |
| S08117-1-Q1 | PPO_Gm19_1563k2-1 | X | 1564563 | 1564960 | Both | L border GEID4520632/ GEID7589905 | |
| S08119-1-Q1 | PPO_Gm19_1566k2-1 | Glyma19g01920.1 | 1567791 | 1568282 | Both | | histone deacetylase |
| S08118-1-Q1 | PPO_Gm19_1566k4-1 | Glyma19g01920.1 | 1569273 | 1569748 | Both | | histone deacetylase |
| S08116-1-Q1 | PPO_Gm19_1566k5-1 | Glyma19g01920.1 | 1570198 | 1570729 | Both | | histone deacetylase |
| S08101-1-Q1 | PPO_Gm19_1586k1-1 | Glyma19g01940.1 | 1587051 | 1587687 | Both | | multidrug/ pheromone exporter, ABC superfamily |
| S08112-1-Q1 | PPO_Gm19_1586k1-1 | Glyma19g01940.1 | 1587051 | 1587687 | Both | | multidrug/ pheromone exporter, ABC superfamily |
| S08108-1-Q1 | PPO_Gm19_1586k2-1 | Glyma19g01940.1 | 1587805 | 1588500 | Both | | multidrug/ pheromone exporter, ABC superfamily |
| S08101-1-Q1 | PPO_Gm19_1586k4-1 | Glyma19g01940.1 | 1589409 | 1590062 | Both | | multidrug/ pheromone exporter, ABC superfamily |
| S08101-2-Q1 | PPO_Gm19_1586k4-1 | Glyma19g01940.1 | 1589409 | 1590062 | Both | | multidrug/ pheromone exporter, ABC superfamily |
| S08101-3-Q1 | PPO_Gm19_1586k4-1 | Glyma19g01940.1 | 1589409 | 1590062 | Both | | multidrug/ pheromone exporter, ABC superfamily |
| S08101-4-Q1 | PPO_Gm19_1586k4-1 | Glyma19g01940.1 | 1589409 | 1590062 | Both | | multidrug/ pheromone exporter, ABC superfamily |
| S08105-1-Q1 | PPO_Gm19_1618k2-1 | X | 1619657 | 1620279 | Both | R border GEID1653063/ GEID3495695 | |
| S03859-1-A | sbacm.pk005.c3.f | X | 1634882 | 1635399 | Both | | |
| S08010-1-Q1 | PPO_Gm19_2089k4-1 | Glyma19g02370.1 | 2091644 | 2092359 | Both | R border GEID4520632/ GEID7589905 | |
| S08010-2-Q2 | PPO_Gm19_2089k4-1 | Glyma19g02370.1 | 2091644 | 2092359 | Both | | |

Tables 13A-13G: Fine-mapping of the PPO herbicide tolerance QTL interval with recombinants from the GEID1653063×GEID3495695 population. Key recombinants delimit the QTL to the ~70 kb interval between S08110-1-Q1 and S08105-1-Q1.

TABLE 13A

| Marker Amplicon/Pos Sample | S04867-1-A Gm19:841750 | S08102-1-Q1 PPO_Gm19_1487k3-1 | S08103-1-Q1 PPO_Gm19_1491k1-1 | S08104-1-Q1 PPO_Gm19_1491k2-1 |
|---|---|---|---|---|
| SJ22185925 | B | B | B | B |
| SJ22186974 | B | B | B | B |
| SJ22185946 | B | B | B | B |
| SJ22186019 | B | B | B | B |
| SJ22186923 | H | H | H | H |
| SJ22185604 | H | H | H | H |
| SJ22186029 | H | H | H | H |
| SJ22186052 | A | A | A | A |
| SJ22185534 | B | A | A | A |
| SJ22185552 | A | A | A | A |
| SJ22186842 | A | A | — | A |
| SJ22186924 | A | A | A | A |
| SJ22186873 | A | A | A | A |
| SJ22186894 | A | A | A | A |
| SJ22185957 | B | A | A | A |
| SJ22185941 | A | A | A | A |
| SJ22186872 | H | A | A | A |
| SJ22185984 | H | H | H | H |

TABLE 13B

| Marker Amplicon/Pos Sample | S08106-1-Q1 PPO_Gm19_1499k2-1 | S08107-1-Q1 PPO_Gm19_1541k3-1 | S08109-1-Q1 PPO_Gm19_1541k4-1 | S08110-1-Q1 PPO_Gm19_1548k1-1 |
|---|---|---|---|---|
| SJ22185925 | B2 | B | B | B |
| SJ22186974 | B1 | B | B | B |
| SJ22185946 | B2 | B | B | B |
| SJ22186019 | B2 | B | B | B |
| SJ22186923 | H | B | — | B |
| SJ22185604 | H | H | H | H |
| SJ22186029 | H | H | H | H |
| SJ22186052 | A | A | A | A |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | H | A | A | A |
| SJ22185957 | A | A | A | A |
| SJ22185941 | A | A | A | A |
| SJ22186872 | A | A | A | A |
| SJ22185984 | H | A | A | A |

TABLE 13C

| Marker Amplicon/Pos Sample | S08111-1-Q1 PPO_Gm19_1548k2-1 | S08115-2-Q1 PPO_Gm19_1563k1-1 | S08117-1-Q1 PPO_Gm19_1563k2-1 | S08119-1-Q1 PPO_Gm19_1566k2-1 |
|---|---|---|---|---|
| SJ22185925 | B | B | B | B |
| SJ22186974 | B | B/H | B | B |
| SJ22185946 | B | B | B | B |
| SJ22186019 | B | B | B | B |
| SJ22186923 | B | B | B | B |
| SJ22185604 | H | H | H | H |
| SJ22186029 | H | H | H | H |
| SJ22186052 | — | H | H | H |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | A | A | A | A |

TABLE 13C-continued

| Marker Amplicon/Pos Sample | S08111-1-Q1 PPO_Gm19_1548k2-1 | S08115-2-Q1 PPO_Gm19_1563k1-1 | S08117-1-Q1 PPO_Gm19_1563k2-1 | S08119-1-Q1 PPO_Gm19_1566k2-1 |
|---|---|---|---|---|
| SJ22185957 | A | A | A | — |
| SJ22185941 | A | A | A | A |
| SJ22186872 | A | A | A | — |
| SJ22185984 | A | A | A | A |

TABLE 13D

| Marker Amplicon/Pos Sample | S08118-1-Q1 PPO_Gm19_1566k4-1 | S08116-1-Q1 PPO_Gm19_1566k5-1 | S08101-1-Q1 PPO_Gm19_1586k1-1 | S08112-1-Q1 PPO_Gm19_1586k1-1 |
|---|---|---|---|---|
| SJ22185925 | B | B | B | B |
| SJ22186974 | — | B | B | B |
| SJ22185946 | B | B | B | B |
| SJ22186019 | — | B | B | B |
| SJ22186923 | B | B | B | B |
| SJ22185604 | H | H | H | H |
| SJ22186029 | H | H | H | H |
| SJ22186052 | — | H | H | H |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | A | A | A | A |
| SJ22185957 | A | A | A | A |
| SJ22185941 | A | A | A | A |
| SJ22186872 | A | A | A | A |
| SJ22185984 | A | A | A | A |

TABLE 13E

| Marker Amplicon/Pos Sample | S08108-1-Q1 PPO_Gm19_1586k2-1 | S08101-1-Q1 PPO_Gm19_1586k4-1 | S08101-2-Q1 PPO_Gm19_1586k4-1 | S08101-3-Q1 PPO_Gm19_1586k4-1 |
|---|---|---|---|---|
| SJ22185925 | B | B | B | B |
| SJ22186974 | B | B | B | B |
| SJ22185946 | B | B | B | B |
| SJ22186019 | B | B | B | B |
| SJ22186923 | B | B | B | B |
| SJ22185604 | H | H | H | H |
| SJ22186029 | H | H | H | H |
| SJ22186052 | H | H | H | H |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | A | A | A | A |
| SJ22185957 | A | A | A | A |
| SJ22185941 | A | A | A | A |
| SJ22186872 | A | A | A | A |
| SJ22185984 | A | A | A | A |

TABLE 13F

| Marker Amplicon/Pos Sample | S08101-4-Q1 PPO_Gm19_1586k4-1 | S08105-1-Q1 PPO_Gm19_1618k2-1 | S03859-1-A PPO_Gm19_1635140 | S08010-1-Q1 PPO_Gm19_2089k4-1 |
|---|---|---|---|---|
| SJ22185925 | B | B | B | A |
| SJ22186974 | B | B | B | A |
| SJ22185946 | B | B | B | A |
| SJ22186019 | B | H | H | H |
| SJ22186923 | B | B | B | B |
| SJ22185604 | H | B | B | B |
| SJ22186029 | H | H | H | B |
| SJ22186052 | H | H | H | H |

TABLE 13F-continued

| Marker Amplicon/Pos Sample | S08101-4-Q1 PPO__Gm19__1586k4-1 | S08105-1-Q1 PPO__Gm19__1618k2-1 | S03859-1-A PPO__Gm19__1635140 | S08010-1-Q1 PPO__Gm19__2089k4-1 |
|---|---|---|---|---|
| SJ22185534 | A | A | A | B |
| SJ22185552 | A | A | A | B |
| SJ22186842 | A | A | A | B |
| SJ22186924 | A | A | A | B |
| SJ22186873 | A | A | A | B |
| SJ22186894 | A | B | B | B |
| SJ22185957 | A | A | A | B |
| SJ22185941 | A | H | H | H |
| SJ22186872 | A | A | A | B |
| SJ22185984 | A | A | A | A |

TABLE 13G

| Marker Amplicon/Pos Sample | S08010-2-Q2 PPO__Gm19__2089k4-1 | Comment | Phenotype |
|---|---|---|---|
| SJ22185925 | A | | TOL |
| SJ22186974 | A | | TOL |
| SJ22185946 | H | | TOL |
| SJ22186019 | H | R Border | TOL |
| SJ22186923 | B | | TOL |
| SJ22185604 | B | | SEG |
| SJ22186029 | B | | SEG |
| SJ22186052 | H | L Border | SEG |
| SJ22185534 | B | | SUS |
| SJ22185552 | B | | SUS |
| SJ22186842 | B | | SUS |
| SJ22186924 | B | | SUS |
| SJ22186873 | B | | SUS |
| SJ22186894 | B | R Border | SUS |
| SJ22185957 | B | | SUS |
| SJ22185941 | H | R Border | SUS |
| SJ22186872 | B | | SUS |
| SJ22185984 | A | | SUS |

Tables 14A-14C: Fine-mapping of the PPO herbicide tolerance QTL interval with recombinants from the GEID4520632×GEID7589905 population.

TABLE 14A

| Sample | Comment | Marker Phenotype | S04867-1-A | S08102-1-Q1 | S08103-1-Q1 | S08104-1-Q1 | S08115-2-Q1 | S08117-1-Q1 |
|---|---|---|---|---|---|---|---|---|
| SP21669249 | R Border | TOL | H | B | B | B | B | B |
| SP21669332 | R Border | TOL | B | B | — | B | B | B |
| SP21669615 | R Border | TOL | B | — | B | B | B | B |
| SP21669616 | R Border | TOL | B | B | — | B | B/H | B |
| SP21669670 | R Border | TOL | H | B | B | B | — | B |
| SP21669503 | L Border | SEG | B | B | B | B | B | B |
| SP21669458 | R Border | SUS | A | A | A | A | A | A |
| SP21669760 | R Border | SUS | A | A | A | A | A | A |

TABLE 14B

| Sample | Comment | Marker Phenotype | S08119-1-Q1 | S08118-1-Q1 | S08116-1-Q1 | S08101-1-Q1 | S08112-1-Q1 | S08108-1-Q1 |
|---|---|---|---|---|---|---|---|---|
| SP21669249 | R Border | TOL | B | B | B | B | B | B |
| SP21669332 | R Border | TOL | B | B | B | B | B | B |
| SP21669615 | R Border | TOL | B | B | B | B | B | B |
| SP21669616 | R Border | TOL | B | B | B | B | B/H | B |
| SP21669670 | R Border | TOL | B | B | B | B | B | B |
| SP21669503 | L Border | SEG | H | H | H | H | H | H |
| SP21669458 | R Border | SUS | A | A | A | A | A | A |
| SP21669760 | R Border | SUS | A | A | A | A | A | A |

TABLE 14C

| Sample | Comment | Marker Phenotype | S08101-1-Q1 | S08101-2-Q1 | S08101-3-Q1 | S08101-4-Q1 | S08105-1-Q1 | S03859-1-A |
|---|---|---|---|---|---|---|---|---|
| SP21669249 | R Border | TOL | B | B | B | B | B | B |
| SP21669332 | R Border | TOL | B | B | B | — | B | B |
| SP21669615 | R Border | TOL | B | B | B | B | B | B |
| SP21669616 | R Border | TOL | B | B | B | B | B | B |
| SP21669670 | R Border | TOL | B | B | B | B | B | B |
| SP21669503 | L Border | SEG | H | H | H | H | H | H |

TABLE 14C-continued

| Sample | Comment | Marker Phenotype | S08101-1-Q1 | S08101-2-Q1 | S08101-3-Q1 | S08101-4-Q1 | S08105-1-Q1 | S03859-1-A |
|---|---|---|---|---|---|---|---|---|
| SP21669458 | R Border | SUS | A | A | A | A | A | A |
| SP21669760 | R Border | SUS | A | A | A | A | A | A |

TABLE 14D

| Sample | Comment | Marker Phenotype | S08010-1-Q1 | S08010-2-Q2 |
|---|---|---|---|---|
| SP21669249 | R Border | TOL | H | H |
| SP21669332 | R Border | TOL | H | H |
| SP21669615 | R Border | TOL | B | B |
| SP21669616 | R Border | TOL | H | H |
| SP21669670 | R Border | TOL | B | B |
| SP21669503 | L Border | SEG | H | H |
| SP21669458 | R Border | SUS | H | H |
| SP21669760 | R Border | SUS | H | H |

Example 7

SNP Haplotype Association Analysis

Association analysis of SNP haplotypes across the PPO QTL region provides an independent method of validating the PPO interval. From the panel of susceptible and tolerant lines used to identify SNPs for Taqman® probe development, 235 SNPs from 49 amplicons were identified in the vicinity of the closely linked marker S03859-1-A. The resulting SNP haplotype data was analyzed to identify an interval in which all of the haplotypes from the susceptible and tolerant lines co-segregated with each other (Table 15).

Although it is difficult to definitively define the co-segregating region, it can conservatively be estimated to reside between amplicons PPO_Gm19_1563k1 and PPO_Gm19_1618k2. Within the borders defined by these loci, there are 38 SNP differences that are shared between all of the susceptible lines compared to all the tolerant lines. This interval is approximately the same ~56 kb interval identified by fine-mapping.

It will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All publications referred to herein are incorporated by reference herein for the purpose cited to the same extent as if each was specifically and individually indicated to be incorporated by reference herein.

TABLE 15

SNP haplotype association analysis of the PPO herbicide tolerance QTL interval. Perfect association between haplotype and phenotype between amplicons Gm19_1563k1 and Gm19_1618k2 defines the QTL interval.

| GEID | Amplicon | 1563k1 | 1563k1 | 1563k1 | 1563k1 | 1618k2 | 1618k2 |
|---|---|---|---|---|---|---|---|
| 627002 | TOL (PPO) | G | G | A | C | * | C |
| 3911338 | TOL (PPO) | G | G | A | C | * | C |
| 1564727 | TOL (PPO) | G | G | A | C | * | C |
| 4230314 | TOL (PPO) | G | G | A | C | * | C |
| 4135359 | TOL (PPO) | G | G | A | C | * | C |
| 4611588 | TOL (PPO) | G | G | A | C | * | C |
| 1590166 | TOL (PPO) | G | G | A | C | * | C |
| 3395451 | TOL (PPO) | G | G | A | C | * | C |
| 2322432 | TOL (PPO) | G | G | A | C | * | C |
| 4520632 | TOL (PPO) | G | G | A | C | * | C |
| 632343 | TOL (PPO) | G | G | A | C | * | C |
| 1770139 | TOL (PPO) | G | G | A | C | * | C |
| 3587853 | TOL (PPO) | G | G | A | C | * | C |
| 4553991 | TOL (PPO) | G | G | A | C | * | C |
| 5183219 | TOL (PPO) | G | G | A | C | * | C |
| 2636517 | TOL (PPO) | G | G | A | C | * | C |
| 3495695 | TOL (PPO) | G | G | A | C | * | C |
| 1737165 | SUS (PPO) | A | * | G | T | A | A |
| 1653063 | SUS (PPO) |   |   |   |   | A | A |
| 4501774 | SUS (PPO) | A | * | G | T | A | A |
| 7589905 | SUS (PPO) | A | * | G | T | N | A |
| 4832982 | SUS (PPO) | A | * | G | T | N | A |
| 2839548 | SUS (PPO) | A | * | G | T |   |   |
| 3958440 | SUS (PPO) | A | * | G | T | A | A |
| 6116656 | SUS (PPO) | A | * | G | T | A | A |

What is claimed is:

1. A method of selecting a soybean plant or germplasm with tolerance or improved tolerance to herbicides that inhibit protoporphyrinogen oxidase function, the method comprising:
   a) isolating nucleic acid from a soybean plant or germplasm, wherein said isolated nucleic acid comprises at least one allele of a marker locus that is associated with the tolerance or improved tolerance to herbicides that inhibit protoporphyrinogen oxidase function, wherein the marker locus is localized within a chromosome interval flanked by and including S08102-1-Q1 and S08101-3-Q1 on linkage group L; and
   b) selecting the soybean plant or germplasm comprising the allele, thereby selecting a soybean plant with tolerance or improved tolerance to herbicides that inhibit protoporphyrinogen oxidase function.

2. The method of claim 1, wherein the marker locus is selected from the group consisting of S08102-1-Q1, S08103-1-Q1, S08104-1-Q1, S08106-1-Q1, S08107-1-Q1, S08109-1-Q1, S08110-1-Q1, S08111-1-Q1, S08115-2-Q1, S08117-1-Q1, S08119-1-Q1, S08118-1-Q1, S08116-1-Q1, S08112-1-Q1, S08108-1-Q1, S08101-4-Q1, S08101-1-Q1, S08101-2-Q1, and S08101-3-Q1.

3. The method of claim 1, wherein the marker locus is localized to a chromosomal interval flanked by and including markers S08109-1-Q1 and S08101-3-Q1 on linkage group L.

4. The method of claim 1, wherein the marker locus is localized to a chromosomal interval flanked by and including markers S08119-1-Q1 and S08101-3-Q1 on linkage group L.

5. The method of claim 1, wherein the marker locus is localized to a chromosomal interval flanked by and including markers S08119-1-Q1 and S08108-1-Q1 on linkage group L.

6. The method of claim 1, wherein the herbicide is selected from the group consisting of diphenylethers, N-phenylpthalamides, oxadiazole and triazolinones.

7. The method of claim 6, wherein the herbicide is selected from the group consisting of sulfentrazone, carfentrazone-ethyl, aciflourfen, lactofen, fomesafen, flumioxazin, flumiclorac-pentyl and oxyfluorfen.

8. The method of claim 1, wherein the selection occurs as part of further breeding to improve a soybean variety's tolerance to one or more herbicides that inhibit protoporphyrinogen oxidase function.

9. The method of claim 8, wherein the further breeding is selected from the group consisting of additional crosses with other lines, hybrids, backcrossing, self-crossing, and combinations thereof.

10. A method for selectively controlling weeds in a field containing a soybean crop comprising:
   (a) planting a field with crop seeds or plants obtained by the method of claim 1 which are tolerant to herbicides that inhibit protoporphyrinogen oxidase function as a result of comprising at least one allele of a marker that is associated with the tolerance, wherein the marker is localized within a chromosomal interval flanked by and including S08102-1-Q1 and S08101-3-Q1 on linkage group L; and
   (b) applying a sufficient amount of a herbicide that inhibits protoporphyrinogen oxidase function to control the weeds without significantly affecting the crop.

11. The method of claim 10, wherein the marker is selected from the group consisting of S08102-1-Q1, S08103-1-Q1, S08104-1-Q1, S08106-1-Q1, S08107-1-Q1, S08109-1-Q1, S08110-1-Q1, S08111-1-Q1, S08115-2-Q1, S08117-1-Q1, S08119-1-Q1, S08118-1-Q1, S08116-1-Q1, S08112-1-Q1, S08108-1-Q1, S08101-4-Q1, S08101-1-Q1, S08101-2-Q1, and S08101-3-Q1.

12. The method of claim 10, wherein said marker is localized to a chromosomal interval flanked by and including markers S08109-1-Q1 and S08101-3-Q1 on linkage group L.

13. The method of claim 10, wherein said marker is localized to a chromosomal interval flanked by and including markers S08119-1-Q1 and S08101-3-Q1 on linkage group L.

14. The method of claim 10, wherein said marker is localized to a chromosomal interval flanked by and including markers S08119-1-Q1 and S08108-1-Q1 on linkage group L.

15. The method of claim 10, wherein the herbicide is applied as a pre-emergent herbicide.

16. The method of claim 10, wherein the herbicide is applied as a post-emergent herbicide.

17. The method of claim 10, further comprising applying to the crop and weeds in the field a simultaneous or chronologically staggered application of a herbicide that inhibits protoporphyrinogen oxidase function and optionally an additional herbicide formulation.

18. The method of claim 17, wherein the additional herbicide formulation is applied and the herbicide formulation contains an active ingredient selected from the group consisting of a hydroxyphenylpyruvatedioxygenase inhibitor, a glyphosate, a sulfonylurea, a sulfonamide, an imidazolinone, a bialaphos, a phosphinothricin, an azafenidin, a butafenacil, a sulfosate, a glufosinate, a dicamba, and a protox inhibitor.

19. The method of claim 18, wherein said additional herbicide formulation is applied simultaneously or sequentially.

20. The method of claim 18, wherein said crop seeds or plants further comprise tolerance to the active ingredient of the additional herbicide formulation.

21. The method of claim 20, wherein tolerance to the active ingredient of the additional herbicide formulation is provided by insertion of a transgene which confers the tolerance.

22. A method for selectively screening soybean plants for herbicide tolerance comprising:
    (a) planting soybean seeds or plants obtained by the method of claim 1 comprising a marker localizing within a chromosomal interval flanked by and including S08102-1-Q1 and S08101-3-Q1 on linkage group L; and
    (b) treating the plants by applying a sufficient amount of a herbicide that inhibits protoporphyrinogen oxidase function to differentiate between susceptible and tolerant plants;
    (c) scoring the treated plants for tolerance to the herbicide.

23. The method of claim 22, wherein the marker is selected from the group consisting of S08102-1-Q1, S08103-1-Q1, S08104-1-Q1, S08106-1-Q1, S08107-1-Q1, S08109-1-Q1, S08110-1-Q1, S08111-1-Q1, S08115-2-Q1, S08117-1-Q1, S08119-1-Q1, S08118-1-Q1, S08116-1-Q1, S08112-1-Q1, S08108-1-Q1, S08101-4-Q1, S08101-1-Q1, S08101-2-Q1, and S08101-3-Q1.

24. The method of claim 22, wherein said marker is localized to a chromosomal interval flanked by and including markers S08109-1-Q1 and S08101-3-Q1 on linkage group L.

25. The method of claim 22, wherein said marker is localized to a chromosomal interval flanked by and including markers S08119-1-Q1 and S08101-3-Q1 on linkage group L.

26. The method of claim 22, wherein said marker is localized to a chromosomal interval flanked by and including markers S08119-1-Q1 and S08108-1-Q1 on linkage group L.

* * * * *

SEQUENCE LISTING

<160> NUMBER OF SEQ ID NOS: 117

<210> SEQ ID NO 1
<211> LENGTH: 22
<212> TYPE: DNA
<213> ORGANISM: Glycine max

<400> SEQUENCE: 1
ttattgaggt gggcaaggtg tg                                          22

<210> SEQ ID NO 2
<211> LENGTH: 23
<212> TYPE: DNA
<213> ORGANISM: Glycine max

<400> SEQUENCE: 2
catgaacgtc tggtggttga aca                                         23

<210> SEQ ID NO 3
<211> LENGTH: 27
<212> TYPE: DNA
<213> ORGANISM: Glycine max

<400> SEQUENCE: 3
gcgatttctt ccttgaagaa ttttctg                                     27

<210> SEQ ID NO 4
<211> LENGTH: 27
<212> TYPE: DNA
<213> ORGANISM: Glycine max

<400> SEQUENCE: 4 gcgcttttc ggctgttatt tttaact                                      27

<210> SEQ ID NO 5
<211> LENGTH: 30
<212> TYPE: DNA
<213> ORGANISM: Glycine max

<400> SEQUENCE: 5
gagggctatg ttttcttctc cagatgtgag                                  30

<210> SEQ ID NO 6
<211> LENGTH: 26
<212> TYPE: DNA
<213> ORGANISM: Glycine max

<400> SEQUENCE: 6
aaggtcggct tggtggttaa aggcag                                      26

<210> SEQ ID NO 7
<211> LENGTH: 13
<212> TYPE: DNA
<213> ORGANISM: Glycine max

<400> SEQUENCE: 7
tcatctgtga taa                                                    13

<210> SEQ ID NO 8
<211> LENGTH: 13
<212> TYPE: DNA
<213> ORGANISM: Glycine max

-continued

```
<400> SEQUENCE: 8
tcatgtgtga taa                                                              13

<210> SEQ ID NO 9
<211> LENGTH: 13
<212> TYPE: DNA
<213> ORGANISM: Glycine max

<400> SEQUENCE: 9
tcatctctga taa                                                              13

<210> SEQ ID NO 10
<211> LENGTH: 22
<212> TYPE: DNA
<213> ORGANISM: Glycine max

<400> SEQUENCE: 10
ctggacctac ccgggatgaa aa                                                    22

<210> SEQ ID NO 11
<211> LENGTH: 22
<212> TYPE: DNA
<213> ORGANISM: Glycine max

<400> SEQUENCE: 11
tcttcctctc ccttcctctc gc                                                    22

<210> SEQ ID NO 12
<211> LENGTH: 13
<212> TYPE: DNA
<213> ORGANISM: Glycine max

<400> SEQUENCE: 12
cgcgactctc ctc                                                              13

<210> SEQ ID NO 13
<211> LENGTH: 13
<212> TYPE: DNA
<213> ORGANISM: Glycine max

<400> SEQUENCE: 13
cgcgagtctc ctc                                                              13

<210> SEQ ID NO 14
<211> LENGTH: 27
<212> TYPE: DNA
<213> ORGANISM: Glycine max

<400> SEQUENCE: 14
tcccaggtta gattttctga acgaaga                                               27

<210> SEQ ID NO 15
<211> LENGTH: 24
<212> TYPE: DNA
<213> ORGANISM: Glycine max

<400> SEQUENCE: 15
catcagcaca aaagggcatc ctca                                                  24

<210> SEQ ID NO 16
<211> LENGTH: 16
<212> TYPE: DNA
<213> ORGANISM: Glycine max
```

```
<400> SEQUENCE: 16
cactccttaa ggtaat                                                      16

<210> SEQ ID NO 17
<211> LENGTH: 16
<212> TYPE: DNA
<213> ORGANISM: Glycine max

<400> SEQUENCE: 17
cactccttaa gataat                                                      16

<210> SEQ ID NO 18
<211> LENGTH: 20
<212> TYPE: DNA
<213> ORGANISM: Glycine max

<400> SEQUENCE: 18
gttatcgtca ccaccaccaa                                                  20

<210> SEQ ID NO 19
<211> LENGTH: 21
<212> TYPE: DNA
<213> ORGANISM: Glycine max

<400> SEQUENCE: 19
cacaacacga gtagccgtag g                                                21

<210> SEQ ID NO 20
<211> LENGTH: 16
<212> TYPE: DNA
<213> ORGANISM: Glycine max

<400> SEQUENCE: 20
aacggatcat cacaac                                                      16

<210> SEQ ID NO 21
<211> LENGTH: 15
<212> TYPE: DNA
<213> ORGANISM: Glycine max

<400> SEQUENCE: 21
aacggctcat cacaa                                                       15

<210> SEQ ID NO 22
<211> LENGTH: 20
<212> TYPE: DNA
<213> ORGANISM: Glycine max

<400> SEQUENCE: 22
cgacaatggc ctttacacct                                                  20

<210> SEQ ID NO 23
<211> LENGTH: 20
<212> TYPE: DNA
<213> ORGANISM: Glycine max

<400> SEQUENCE: 23
tcgatatgga cgaaggagga                                                  20

<210> SEQ ID NO 24
<211> LENGTH: 16
<212> TYPE: DNA
<213> ORGANISM: Glycine max
```

```
<400> SEQUENCE: 24
acaccatttt tcatcc                                                     16

<210> SEQ ID NO 25
<211> LENGTH: 16
<212> TYPE: DNA
<213> ORGANISM: Glycine max

<400> SEQUENCE: 25
acaccctttt tcatcc                                                     16

<210> SEQ ID NO 26
<211> LENGTH: 22
<212> TYPE: DNA
<213> ORGANISM: Glycine max

<400> SEQUENCE: 26
gcaatcacat ttgcattcct ta                                              22

<210> SEQ ID NO 27
<211> LENGTH: 21
<212> TYPE: DNA
<213> ORGANISM: Glycine max

<400> SEQUENCE: 27
tctgaacgag ttgtgcaaga a                                               21

<210> SEQ ID NO 28
<211> LENGTH: 16
<212> TYPE: DNA
<213> ORGANISM: Glycine max

<400> SEQUENCE: 28
actgctgctt tgtcta                                                     16

<210> SEQ ID NO 29
<211> LENGTH: 16
<212> TYPE: DNA
<213> ORGANISM: Glycine max

<400> SEQUENCE: 29
ctactgctac tttgtc                                                     16

<210> SEQ ID NO 30
<211> LENGTH: 20
<212> TYPE: DNA
<213> ORGANISM: Glycine max

<400> SEQUENCE: 30
acctcgtatt ggtggtggtg                                                 20

<210> SEQ ID NO 31
<211> LENGTH: 20
<212> TYPE: DNA
<213> ORGANISM: Glycine max

<400> SEQUENCE: 31
gaatgttcag tgcgagcaac                                                 20

<210> SEQ ID NO 32
<211> LENGTH: 15
<212> TYPE: DNA
<213> ORGANISM: Glycine max
```

```
<400> SEQUENCE: 32
acttccctcg tttcg                                                    15

<210> SEQ ID NO 33
<211> LENGTH: 14
<212> TYPE: DNA
<213> ORGANISM: Glycine max

<400> SEQUENCE: 33
cttccctcat ttcg                                                     14

<210> SEQ ID NO 34
<211> LENGTH: 22
<212> TYPE: DNA
<213> ORGANISM: Glycine max

<400> SEQUENCE: 34
caaaaggaaa gaagaaccgt gt                                            22

<210> SEQ ID NO 35
<211> LENGTH: 21
<212> TYPE: DNA
<213> ORGANISM: Glycine max

<400> SEQUENCE: 35
tccaacctat gtgttggtgt g                                             21

<210> SEQ ID NO 36
<211> LENGTH: 17
<212> TYPE: DNA
<213> ORGANISM: Glycine max

<400> SEQUENCE: 36
atgattgaag caggaaa                                                  17

<210> SEQ ID NO 37
<211> LENGTH: 18
<212> TYPE: DNA
<213> ORGANISM: Glycine max

<400> SEQUENCE: 37
tcatgattga agcagcaa                                                 18

<210> SEQ ID NO 38
<211> LENGTH: 27
<212> TYPE: DNA
<213> ORGANISM: Glycine max

<400> SEQUENCE: 38
ggagacttga cttaaagaga aagaaaa                                       27

<210> SEQ ID NO 39
<211> LENGTH: 26
<212> TYPE: DNA
<213> ORGANISM: Glycine max

<400> SEQUENCE: 39
cggaaagaaa aacaatagat tgaatg                                        26

<210> SEQ ID NO 40
<211> LENGTH: 19
<212> TYPE: DNA
<213> ORGANISM: Glycine max
```

-continued

<400> SEQUENCE: 40
cttgttctag actgatcat                                              19

<210> SEQ ID NO 41
<211> LENGTH: 16
<212> TYPE: DNA
<213> ORGANISM: Glycine max

<400> SEQUENCE: 41
ctagactgat aattca                                                 16

<210> SEQ ID NO 42
<211> LENGTH: 26
<212> TYPE: DNA
<213> ORGANISM: Glycine max

<400> SEQUENCE: 42
tcattcaaga ctacatgaaa gacaaa                                      26

<210> SEQ ID NO 43
<211> LENGTH: 20
<212> TYPE: DNA
<213> ORGANISM: Glycine max

<400> SEQUENCE: 43
caagggagag caatccttga                                             20

<210> SEQ ID NO 44
<211> LENGTH: 16
<212> TYPE: DNA
<213> ORGANISM: Glycine max

<400> SEQUENCE: 44
atagtctccc aaacac                                                 16

<210> SEQ ID NO 45
<211> LENGTH: 17
<212> TYPE: DNA
<213> ORGANISM: Glycine max

<400> SEQUENCE: 45
atagtctctc aaacacc                                                17

<210> SEQ ID NO 46
<211> LENGTH: 22
<212> TYPE: DNA
<213> ORGANISM: Glycine max

<400> SEQUENCE: 46
gaaactttcc attttgccct tc                                          22

<210> SEQ ID NO 47
<211> LENGTH: 18
<212> TYPE: DNA
<213> ORGANISM: Glycine max

<400> SEQUENCE: 47
agaacgcagg ggagaagc                                               18

<210> SEQ ID NO 48
<211> LENGTH: 16
<212> TYPE: DNA
<213> ORGANISM: Glycine max

-continued

```
<400> SEQUENCE: 48
cttcttccac tcttac                                              16

<210> SEQ ID NO 49
<211> LENGTH: 17
<212> TYPE: DNA
<213> ORGANISM: Glycine max

<400> SEQUENCE: 49
ccttcttaca ctcttac                                             17

<210> SEQ ID NO 50
<211> LENGTH: 28
<212> TYPE: DNA
<213> ORGANISM: Glycine max

<400> SEQUENCE: 50
tgatatgaca ctctactaag atgtgttg                                 28

<210> SEQ ID NO 51
<211> LENGTH: 20
<212> TYPE: DNA
<213> ORGANISM: Glycine max

<400> SEQUENCE: 51
tgattcatcc gcaaacttga                                          20

<210> SEQ ID NO 52
<211> LENGTH: 17
<212> TYPE: DNA
<213> ORGANISM: Glycine max

<400> SEQUENCE: 52
cactctccta tattgtc                                             17

<210> SEQ ID NO 53
<211> LENGTH: 16
<212> TYPE: DNA
<213> ORGANISM: Glycine max

<400> SEQUENCE: 53
ctctcctaca ttgtca                                              16

<210> SEQ ID NO 54
<211> LENGTH: 22
<212> TYPE: DNA
<213> ORGANISM: Glycine max

<400> SEQUENCE: 54
agatccttgt tccaaattcc aa                                       22

<210> SEQ ID NO 55
<211> LENGTH: 20
<212> TYPE: DNA
<213> ORGANISM: Glycine max

<400> SEQUENCE: 55
ccttggctta atgggtgtgt                                          20

<210> SEQ ID NO 56
<211> LENGTH: 16
<212> TYPE: DNA
<213> ORGANISM: Glycine max
```

<400> SEQUENCE: 56
ccaacacaat ctaact                                                    16

<210> SEQ ID NO 57
<211> LENGTH: 14
<212> TYPE: DNA
<213> ORGANISM: Glycine max

<400> SEQUENCE: 57
ccaacacaat cgaa                                                      14

<210> SEQ ID NO 58
<211> LENGTH: 20
<212> TYPE: DNA
<213> ORGANISM: Glycine max

<400> SEQUENCE: 58
atggaggcaa gcttgtgttt                                                20

<210> SEQ ID NO 59
<211> LENGTH: 20
<212> TYPE: DNA
<213> ORGANISM: Glycine max

<400> SEQUENCE: 59
catgctacca gcatctgcaa                                                20

<210> SEQ ID NO 60
<211> LENGTH: 17
<212> TYPE: DNA
<213> ORGANISM: Glycine max

<400> SEQUENCE: 60
cttcataaac gccaaag                                                   17

<210> SEQ ID NO 61
<211> LENGTH: 16
<212> TYPE: DNA
<213> ORGANISM: Glycine max

<400> SEQUENCE: 61
cataaatgcc aaagca                                                    16

<210> SEQ ID NO 62
<211> LENGTH: 20
<212> TYPE: DNA
<213> ORGANISM: Glycine max

<400> SEQUENCE: 62
aatgagcaag ggagaggaca                                                20

<210> SEQ ID NO 63
<211> LENGTH: 20
<212> TYPE: DNA
<213> ORGANISM: Glycine max

<400> SEQUENCE: 63
tcgccgctgc tatttaattt                                                20

<210> SEQ ID NO 64
<211> LENGTH: 18
<212> TYPE: DNA
<213> ORGANISM: Glycine max

```
<400> SEQUENCE: 64
aagcactact ttcaattg                                                 18

<210> SEQ ID NO 65
<211> LENGTH: 14
<212> TYPE: DNA
<213> ORGANISM: Glycine max

<400> SEQUENCE: 65
aagcaccact ttca                                                     14

<210> SEQ ID NO 66
<211> LENGTH: 20
<212> TYPE: DNA
<213> ORGANISM: Glycine max

<400> SEQUENCE: 66
agatgccttg ctcagtggac                                               20

<210> SEQ ID NO 67
<211> LENGTH: 22
<212> TYPE: DNA
<213> ORGANISM: Glycine max

<400> SEQUENCE: 67
atgatgaatg tgttgagcca at                                            22

<210> SEQ ID NO 68
<211> LENGTH: 14
<212> TYPE: DNA
<213> ORGANISM: Glycine max

<400> SEQUENCE: 68
ccccatcacc atac                                                     14

<210> SEQ ID NO 69
<211> LENGTH: 14
<212> TYPE: DNA
<213> ORGANISM: Glycine max

<400> SEQUENCE: 69
accccaccac cata                                                     14

<210> SEQ ID NO 70
<211> LENGTH: 22
<212> TYPE: DNA
<213> ORGANISM: Glycine max

<400> SEQUENCE: 70
agaaaccttc caaagctctt gg                                            22

<210> SEQ ID NO 71
<211> LENGTH: 20
<212> TYPE: DNA
<213> ORGANISM: Glycine max

<400> SEQUENCE: 71
tagggaggca cttgacaacc                                               20

<210> SEQ ID NO 72
<211> LENGTH: 15
<212> TYPE: DNA
<213> ORGANISM: Glycine max
```

```
<400> SEQUENCE: 72
caacatccga gtcca                                            15

<210> SEQ ID NO 73
<211> LENGTH: 15
<212> TYPE: DNA
<213> ORGANISM: Glycine max

<400> SEQUENCE: 73
caacatcaga gtcca                                            15

<210> SEQ ID NO 74
<211> LENGTH: 20
<212> TYPE: DNA
<213> ORGANISM: Glycine max

<400> SEQUENCE: 74
ttttgacccc cagagagttg                                       20

<210> SEQ ID NO 75
<211> LENGTH: 20
<212> TYPE: DNA
<213> ORGANISM: Glycine max

<400> SEQUENCE: 75
ttgcaagcct aaaggatggt                                       20

<210> SEQ ID NO 76
<211> LENGTH: 19
<212> TYPE: DNA
<213> ORGANISM: Glycine max

<400> SEQUENCE: 76
ctatctctac acgatgtgt                                        19

<210> SEQ ID NO 77
<211> LENGTH: 16
<212> TYPE: DNA
<213> ORGANISM: Glycine max

<400> SEQUENCE: 77
ctatctccac acgatg                                           16

<210> SEQ ID NO 78
<211> LENGTH: 20
<212> TYPE: DNA
<213> ORGANISM: Glycine max

<400> SEQUENCE: 78
tcccacttga tcttgcagaa                                       20

<210> SEQ ID NO 79
<211> LENGTH: 20
<212> TYPE: DNA
<213> ORGANISM: Glycine max

<400> SEQUENCE: 79
tacggtgggt ggattattcg                                       20

<210> SEQ ID NO 80
<211> LENGTH: 15
<212> TYPE: DNA
<213> ORGANISM: Glycine max
```

-continued

```
<400> SEQUENCE: 80
cctccaatgg catac                                                    15

<210> SEQ ID NO 81
<211> LENGTH: 17
<212> TYPE: DNA
<213> ORGANISM: Glycine max

<400> SEQUENCE: 81
cctccaatag catacat                                                  17

<210> SEQ ID NO 82
<211> LENGTH: 22
<212> TYPE: DNA
<213> ORGANISM: Glycine max

<400> SEQUENCE: 82
agaaaagcag cagaaagagg ac                                            22

<210> SEQ ID NO 83
<211> LENGTH: 22
<212> TYPE: DNA
<213> ORGANISM: Glycine max

<400> SEQUENCE: 83
cttcatgaat cccaacatca ga                                            22

<210> SEQ ID NO 84
<211> LENGTH: 17
<212> TYPE: DNA
<213> ORGANISM: Glycine max

<400> SEQUENCE: 84
ctctaattcc acatctg                                                  17

<210> SEQ ID NO 85
<211> LENGTH: 18
<212> TYPE: DNA
<213> ORGANISM: Glycine max

<400> SEQUENCE: 85
cctctaattt cacatctg                                                 18

<210> SEQ ID NO 86
<211> LENGTH: 22
<212> TYPE: DNA
<213> ORGANISM: Glycine max

<400> SEQUENCE: 86
tcaaaccatt ttgtttccca gt                                            22

<210> SEQ ID NO 87
<211> LENGTH: 21
<212> TYPE: DNA
<213> ORGANISM: Glycine max

<400> SEQUENCE: 87
tgctagcctt tgatacccaa c                                             21

<210> SEQ ID NO 88
<211> LENGTH: 16
<212> TYPE: DNA
<213> ORGANISM: Glycine max
```

```
<400> SEQUENCE: 88
ttgcattgta ttctct                                                      16

<210> SEQ ID NO 89
<211> LENGTH: 15
<212> TYPE: DNA
<213> ORGANISM: Glycine max

<400> SEQUENCE: 89
ttgcattgta ttttc                                                       15

<210> SEQ ID NO 90
<211> LENGTH: 21
<212> TYPE: DNA
<213> ORGANISM: Glycine max

<400> SEQUENCE: 90
gtctcaggca gtgaatctgc t                                                21

<210> SEQ ID NO 91
<211> LENGTH: 20
<212> TYPE: DNA
<213> ORGANISM: Glycine max

<400> SEQUENCE: 91
cagccttacc atcaacatcg                                                  20

<210> SEQ ID NO 92
<211> LENGTH: 13
<212> TYPE: DNA
<213> ORGANISM: Glycine max

<400> SEQUENCE: 92
ttccgtgaag atc                                                         13

<210> SEQ ID NO 93
<211> LENGTH: 15
<212> TYPE: DNA
<213> ORGANISM: Glycine max

<400> SEQUENCE: 93
atgcttccgc gaaga                                                       15

<210> SEQ ID NO 94
<211> LENGTH: 26
<212> TYPE: DNA
<213> ORGANISM: Glycine max

<400> SEQUENCE: 94
ggtagcagtt actttgtgat gtaagc                                           26

<210> SEQ ID NO 95
<211> LENGTH: 22
<212> TYPE: DNA
<213> ORGANISM: Glycine max

<400> SEQUENCE: 95
catgcaataa aatccaaaac ca                                               22

<210> SEQ ID NO 96
<211> LENGTH: 17
<212> TYPE: DNA
<213> ORGANISM: Glycine max
```

-continued

```
<400> SEQUENCE: 96
tactgatcac aggttat                                              17

<210> SEQ ID NO 97
<211> LENGTH: 17
<212> TYPE: DNA
<213> ORGANISM: Glycine max

<400> SEQUENCE: 97
tactgaccac aggttat                                              17

<210> SEQ ID NO 98
<211> LENGTH: 20
<212> TYPE: DNA
<213> ORGANISM: Glycine max

<400> SEQUENCE: 98
ttgctttgga aaggactcca                                           20

<210> SEQ ID NO 99
<211> LENGTH: 20
<212> TYPE: DNA
<213> ORGANISM: Glycine max

<400> SEQUENCE: 99
cctcatcaac tcctgctgct                                           20

<210> SEQ ID NO 100
<211> LENGTH: 14
<212> TYPE: DNA
<213> ORGANISM: Glycine max

<400> SEQUENCE: 100
ctcggtgctg tttt                                                 14

<210> SEQ ID NO 101
<211> LENGTH: 14
<212> TYPE: DNA
<213> ORGANISM: Glycine max

<400> SEQUENCE: 101
ctcggtgctg tctt                                                 14

<210> SEQ ID NO 102
<211> LENGTH: 23
<212> TYPE: DNA
<213> ORGANISM: Glycine max

<400> SEQUENCE: 102
gaaaccaatt ttgatgtgaa gga                                       23

<210> SEQ ID NO 103
<211> LENGTH: 20
<212> TYPE: DNA
<213> ORGANISM: Glycine max

<400> SEQUENCE: 103
aagtgagagg ggtgcaaaga                                           20

<210> SEQ ID NO 104
<211> LENGTH: 14
<212> TYPE: DNA
<213> ORGANISM: Glycine max
```

-continued

<400> SEQUENCE: 104
cagccctatc tcac                                                       14

<210> SEQ ID NO 105
<211> LENGTH: 14
<212> TYPE: DNA
<213> ORGANISM: Glycine max

<400> SEQUENCE: 105
agccctgtct cact                                                       14

<210> SEQ ID NO 106
<211> LENGTH: 21
<212> TYPE: DNA
<213> ORGANISM: Glycine max

<400> SEQUENCE: 106
gcaaatgaga aggctgaagc t                                               21

<210> SEQ ID NO 107
<211> LENGTH: 19
<212> TYPE: DNA
<213> ORGANISM: Glycine max

<400> SEQUENCE: 107
gctgtccctc agtccatcc                                                  19

<210> SEQ ID NO 108
<211> LENGTH: 15
<212> TYPE: DNA
<213> ORGANISM: Glycine max

<400> SEQUENCE: 108
cggtatcgct cgtca                                                      15

<210> SEQ ID NO 109
<211> LENGTH: 15
<212> TYPE: DNA
<213> ORGANISM: Glycine max

<400> SEQUENCE: 109
tatcgctcgc caacg                                                      15

<210> SEQ ID NO 110
<211> LENGTH: 23
<212> TYPE: DNA
<213> ORGANISM: Glycine max

<400> SEQUENCE: 110
atccacttgc aagataggac act                                             23

<210> SEQ ID NO 111
<211> LENGTH: 26
<212> TYPE: DNA
<213> ORGANISM: Glycine max

<400> SEQUENCE: 111
gtgtaagtac tgatgtgcag ttttga                                          26

<210> SEQ ID NO 112
<211> LENGTH: 19
<212> TYPE: DNA
<213> ORGANISM: Glycine max

<400> SEQUENCE: 112
cttgacatta agactatcc                                                    19

<210> SEQ ID NO 113
<211> LENGTH: 19
<212> TYPE: DNA
<213> ORGANISM: Glycine max

<400> SEQUENCE: 113
agactaatcc ttaaacaag                                                    19

<210> SEQ ID NO 114
<211> LENGTH: 3672
<212> TYPE: DNA
<213> ORGANISM: Glycine max

<400> SEQUENCE: 114

```
atgcatgctg atggcttaga ctggttcctc atgattttg gtctctttgg ggccattggt          60
gatggcatag cacccctttt ggtgttgttt atcaccagca aaattatgaa caatattggt        120
ggttttctta gcaacatagg cagcactttc atccacagca tcaatgagaa tgccgtggtt        180
ttgttatatt tggctggtgg gtctttcatt gcttgtttcc tagagggtta ttgttggaca        240
agaacaggag aaaggcaagc tgcaagaatg agagttaggt accttaaagc agttctcagg        300
caagaagtag catactttga tttgcatgtc acaagcacat cggaggtcat caccagcgtc        360
tctaatgata gcctcgtaat tcaagattgt cttagtgaaa aggtcccaaa ctttttgatg        420
aatgcgtcca tgtttgttgg gagctacata gtggcttttg cattattgtg agagattggcc        480
attgtggggt tccttttgt ggccctactt gtgatcccg gtttcatgta tgggaggaca          540
ttaatggggt tggctagcaa gataagagaa gagtacaata aagcaggcac aatagcagaa        600
caagcaatat cctccatcag aaccgtttat tcttttgtgg gggaaagcaa gactattgat        660
gctttctctg aagccctaca agggtctgtt gagttgggac tgagacaagg cttagcaaaa        720
ggtttagcta ttggaagcaa tggtgttgtc tttgctatat gggcattcat gtcctattat        780
ggtagcagat tggtcatgta ccatggagct aaaggtggga ctgtatttgc agttggagca        840
gccatagctc ttggaggatt ggcactaggt gctggtttgt cgaacgtgaa gtacttctca        900
gaagcaagta ccgcaggaga acgcataatg gaagtgataa aaagggttcc aaagattgat        960
tctgatagca tggctgagga gattctggag aacgtttcag gggaagttga attcaaccat       1020
gtggactttg tgtacccatc aaggccagac agtgttattc tgaatgattt ctgcctaaag       1080
attccagcag ggaaaacagt ggctttggtt ggagggagtg gctctggaaa atccactgtg       1140
atatcacttt tgcagaggtt ttatgaccca attgagggag atatttctt gatggtgtg         1200
gccattcaca gttgcaact caagtggttg aggtctcaaa tgggtttggt cagccaagag       1260
cctgcactgt ttgcaactag cattaaagag aatatacttt ttggaagaga agatgccact       1320
caagaagagg ttgtggaggc agcaaaagct tccaatgctc ataatttcat ttcacagttg       1380
ccacaaggat atgatactca ggttggggag agaggagttc aaatgtcagg tggacaaaag       1440
caaagaattg caatagcacg agcaataata aaaaagccac ggattcttct attagatgaa       1500
gcaacaagtg cactagattc tgaatctgaa cgagttgtgc aagaagcatt agacaaagca       1560
gcagtagggc gcacaacaat catcattgca catagattat ccaccataag gaatgcaaat       1620
gtgattgctg ttgtgcaaag tgggaaaatc atggagatgg gatcacacca tgaactaatc       1680
caaaacgaca atggcctta cacctcacta gttcgtctcc aacaagcaaa aaatgaaaaa       1740
```

-continued

```
gaagacacca tttttcatcc tactcctcct tcgtccatat cgaacaaaga caatcacaac    1800
acgagtagcc gtaggctctc tgttgtgatg atccgttcta gctccaccaa ctcgatacct    1860
cgtattggtg gtggtgacga taacaatatt gttgaagaag tagtggaaga taacaagcca    1920
ccacttccct cgtttcgaag gttgctcgca ctgaacattc ccgagtggaa gcaagcatgt    1980
ttagggtgtt tgaatgcggt gttgtttggt gcaattcagc ctgtgtatgc atttgcaatg    2040
gggtcagtga tatctgttta cttcctccca gaccataatg agataaagaa gaaaactatg    2100
atctattcac tttgtttcct agggttggct gtgttctcct tagtggttaa tatcctccag    2160
cattacaact ttgcttacat aggagagtac ttgactaaaa ggatcagaga agaatgttt     2220 tccaagatac tcacttttga agttggatgg tttgatcaag atgaaaattc cacaggtgct    2280
gtttgttcta gacttgccaa agaagccaat gtgaatggtc tagtggtaca aaccatttca    2340
gcagtggtaa tagcttttac aatgggccta atcattgcat ggaggttggc cattgttatg    2400
atagcagttc aacccattat catagcatgt ttctacacaa ggcgtgtcct tctcaagagc    2460
atgtctagta aggccatcaa ggcccaagat gaaagtagca agatagctgt tgaagctgtt    2520
tccaacctca gaacaatcac agcatttttct tcccaagata ggatccttaa aatgctcgaa    2580
aaggcccaag aaggcccgag ccgtgaaagc attcgacaat catggtttgc gggcattggg    2640
cttgcatgtt cccaaagcct tacattttgc acttgggctt tggactttg gtatggaggc     2700 aagcttgtgt ttcagggctt cataaacgcc aaagcattgt ttgagacctt catgatttta    2760
gtgagcacag gtagggttat tgcagatgct ggtagcatga ccaatgacct agctaaaggg    2820
gctgatgctg tgggctcagt ttttgcaatc ttagataggt acacaaaat tgagccagat     2880 gatgacatag atgggtacaa gcctgaaaag ctaacaggga aaatagagct tcatgatgtc    2940
cattttgcat acccagctag gcccaatgtg atgatcttcc aaggcttctc aatcaaaatt    3000
gatgcaggca gatcaacagc attggttggg caaagtggct ctggaaaatc aacaatcata    3060
ggcttaattg agagattcta tgaccctatg aaagggattg tgaccattga tggtagagac    3120
ataaaatcat accaccttag gtcactaagg aagcatattg ctcttgtaag ccaagagcca    3180
acattgtttg gtgggaccat aagggaaaat attgcatatg gggcatctaa taataataac    3240
aaggttgatg aaactgagat catagaagca gctagggcag ctaatgctca tgatttcatt    3300
gcaagcctaa aggatggtta tgacacatcg tgtagagata gaggagtgca actctctggg    3360
ggtcaaaagc aaagaattgc aatagctaga gccatattga agaatccaga agtgttgttg    3420
ttggatgaag ccacaagtgc cctagatagc caatcagaaa aattggtgca agatgctcta    3480
gaaagggtga tggtggggag aactagtgtg gtggtggctc acaggttaag cacaatacaa    3540
aattgtgacc taattgctgt gttagataag ggaaaagtgg tggagaaagg gacccactca    3600
tctttgttgg ctcatggacc aggtggagct tattactctt tgataagttt acaaagaaga    3660
ccagcaaatt aa                                                        3672
```

<210> SEQ ID NO 115
<211> LENGTH: 1223
<212> TYPE: PRT
<213> ORGANISM: Glycine max

<400> SEQUENCE: 115

Met His Ala Asp Gly Leu Asp Trp Phe Leu Met Ile Phe Gly Leu Phe
1               5                   10                  15

Gly Ala Ile Gly Asp Gly Ile Gly Thr Pro Leu Val Leu Phe Ile Thr
                20                  25                  30

-continued

```
Ser Lys Ile Met Asn Asn Ile Gly Gly Phe Ser Ser Asn Ile Gly Ser
         35                  40                  45

Thr Phe Ile His Ser Ile Asn Glu Asn Ala Val Val Leu Leu Tyr Leu
 50                  55                  60

Ala Gly Gly Ser Phe Ile Ala Cys Phe Leu Glu Gly Tyr Cys Trp Thr
 65                  70                  75                  80

Arg Thr Gly Glu Arg Gln Ala Arg Met Arg Val Arg Tyr Leu Lys
                 85                  90                  95

Ala Val Leu Arg Gln Glu Val Ala Tyr Phe Asp Leu His Val Thr Ser
                100                 105                 110

Thr Ser Glu Val Ile Thr Ser Val Ser Asn Asp Ser Leu Val Ile Gln
                115                 120                 125

Asp Cys Leu Ser Glu Lys Val Pro Asn Phe Leu Met Asn Ala Ser Met
130                 135                 140

Phe Val Gly Ser Tyr Ile Val Ala Phe Ala Leu Leu Trp Arg Leu Ala
145                 150                 155                 160

Ile Val Gly Phe Pro Phe Val Ala Leu Leu Val Ile Pro Gly Phe Met
                165                 170                 175

Tyr Gly Arg Thr Leu Met Gly Leu Ala Ser Lys Ile Arg Glu Glu Tyr
                180                 185                 190

Asn Lys Ala Gly Thr Ile Ala Glu Gln Ala Ile Ser Ser Ile Arg Thr
                195                 200                 205

Val Tyr Ser Phe Val Gly Glu Ser Lys Thr Ile Asp Ala Phe Ser Glu
210                 215                 220

Ala Leu Gln Gly Ser Val Glu Leu Gly Leu Arg Gln Gly Leu Ala Lys
225                 230                 235                 240

Gly Leu Ala Ile Gly Ser Asn Gly Val Val Phe Ala Ile Trp Ala Phe
                245                 250                 255

Met Ser Tyr Tyr Gly Ser Arg Leu Val Met Tyr His Gly Ala Lys Gly
                260                 265                 270

Gly Thr Val Phe Ala Val Gly Ala Ala Ile Ala Leu Gly Gly Leu Ala
                275                 280                 285

Leu Gly Ala Gly Leu Ser Asn Val Lys Tyr Phe Ser Glu Ala Ser Thr
                290                 295                 300

Ala Gly Glu Arg Ile Met Glu Val Ile Lys Arg Val Pro Lys Ile Asp
305                 310                 315                 320

Ser Asp Ser Met Ala Glu Glu Ile Leu Glu Asn Val Ser Gly Glu Val
                325                 330                 335

Glu Phe Asn His Val Asp Phe Val Tyr Pro Ser Arg Pro Asp Ser Val
                340                 345                 350

Ile Leu Asn Asp Phe Cys Leu Lys Ile Pro Ala Gly Lys Thr Val Ala
                355                 360                 365

Leu Val Gly Gly Ser Gly Ser Gly Lys Ser Thr Val Ile Ser Leu Leu
370                 375                 380

Gln Arg Phe Tyr Asp Pro Ile Glu Gly Glu Ile Phe Leu Asp Gly Val
385                 390                 395                 400

Ala Ile His Lys Leu Gln Leu Lys Trp Leu Arg Ser Gln Met Gly Leu
                405                 410                 415

Val Ser Gln Glu Pro Ala Leu Phe Ala Thr Ser Ile Lys Glu Asn Ile
                420                 425                 430

Leu Phe Gly Arg Glu Asp Ala Thr Gln Glu Glu Val Val Glu Ala Ala
                435                 440                 445

Lys Ala Ser Asn Ala His Asn Phe Ile Ser Gln Leu Pro Gln Gly Tyr
450                 455                 460
```

```
Asp Thr Gln Val Gly Glu Arg Gly Val Gln Met Ser Gly Gly Gln Lys
465                 470                 475                 480

Gln Arg Ile Ala Ile Ala Arg Ala Ile Ile Lys Lys Pro Arg Ile Leu
            485                 490                 495

Leu Leu Asp Glu Ala Thr Ser Ala Leu Asp Ser Glu Ser Glu Arg Val
        500                 505                 510

Val Gln Glu Ala Leu Asp Lys Ala Ala Val Gly Arg Thr Thr Ile Ile
    515                 520                 525

Ile Ala His Arg Leu Ser Thr Ile Arg Asn Ala Asn Val Ile Ala Val
530                 535                 540

Val Gln Ser Gly Lys Ile Met Glu Met Gly Ser His His Glu Leu Ile
545                 550                 555                 560

Gln Asn Asp Asn Gly Leu Tyr Thr Ser Leu Val Arg Leu Gln Gln Ala
            565                 570                 575

Lys Asn Glu Lys Glu Asp Thr Ile Phe His Pro Thr Pro Ser Ser
        580                 585                 590

Ile Ser Asn Lys Asp Asn His Asn Thr Ser Ser Arg Arg Leu Ser Val
    595                 600                 605

Val Met Ile Arg Ser Ser Ser Thr Asn Ser Ile Pro Arg Ile Gly Gly
    610                 615                 620

Gly Asp Asp Asn Asn Ile Val Glu Val Val Glu Asp Asn Lys Pro
625                 630                 635                 640

Pro Leu Pro Ser Phe Arg Arg Leu Leu Ala Leu Asn Ile Pro Glu Trp
            645                 650                 655

Lys Gln Ala Cys Leu Gly Cys Leu Asn Ala Val Leu Phe Gly Ala Ile
        660                 665                 670

Gln Pro Val Tyr Ala Phe Ala Met Gly Ser Val Ile Ser Val Tyr Phe
    675                 680                 685

Leu Pro Asp His Asn Glu Ile Lys Lys Lys Thr Met Ile Tyr Ser Leu
    690                 695                 700

Cys Phe Leu Gly Leu Ala Val Phe Ser Leu Val Val Asn Ile Leu Gln
705                 710                 715                 720

His Tyr Asn Phe Ala Tyr Ile Gly Glu Tyr Leu Thr Lys Arg Ile Arg
            725                 730                 735

Glu Arg Met Phe Ser Lys Ile Leu Thr Phe Glu Val Gly Trp Phe Asp
            740                 745                 750

Gln Asp Glu Asn Ser Thr Gly Ala Val Cys Ser Arg Leu Ala Lys Glu
        755                 760                 765

Ala Asn Val Asn Gly Leu Val Val Gln Thr Ile Ser Ala Val Val Ile
770                 775                 780

Ala Phe Thr Met Gly Leu Ile Ile Ala Trp Arg Leu Ala Ile Val Met
785                 790                 795                 800

Ile Ala Val Gln Pro Ile Ile Ile Ala Cys Phe Tyr Thr Arg Arg Val
            805                 810                 815

Leu Leu Lys Ser Met Ser Ser Lys Ala Ile Lys Ala Gln Asp Glu Ser
        820                 825                 830

Ser Lys Ile Ala Val Glu Ala Val Ser Asn Leu Arg Thr Ile Thr Ala
    835                 840                 845

Phe Ser Ser Gln Asp Arg Ile Leu Lys Met Leu Glu Lys Ala Gln Glu
    850                 855                 860

Gly Pro Ser Arg Glu Ser Ile Arg Gln Ser Trp Phe Ala Gly Ile Gly
865                 870                 875                 880

Leu Ala Cys Ser Gln Ser Leu Thr Phe Cys Thr Trp Ala Leu Asp Phe
```

885                 890                 895
Trp Tyr Gly Gly Lys Leu Val Phe Gln Gly Phe Ile Asn Ala Lys Ala
            900                 905                 910

Leu Phe Glu Thr Phe Met Ile Leu Val Ser Thr Gly Arg Val Ile Ala
            915                 920                 925

Asp Ala Gly Ser Met Thr Asn Asp Leu Ala Lys Gly Ala Asp Ala Val
            930                 935                 940

Gly Ser Val Phe Ala Ile Leu Asp Arg Tyr Thr Lys Ile Glu Pro Asp
945                 950                 955                 960

Asp Asp Ile Asp Gly Tyr Lys Pro Glu Lys Leu Thr Gly Lys Ile Glu
            965                 970                 975

Leu His Asp Val His Phe Ala Tyr Pro Ala Arg Pro Asn Val Met Ile
            980                 985                 990

Phe Gln Gly Phe Ser Ile Lys Ile Asp Ala Gly Arg Ser Thr Ala Leu
            995                 1000                1005

Val Gly Gln Ser Gly Ser Gly Lys Ser Thr Ile Ile Gly Leu Ile
      1010                1015                1020

Glu Arg Phe Tyr Asp Pro Met Lys Gly Ile Val Thr Ile Asp Gly
      1025                1030                1035

Arg Asp Ile Lys Ser Tyr His Leu Arg Ser Leu Arg Lys His Ile
      1040                1045                1050

Ala Leu Val Ser Gln Glu Pro Thr Leu Phe Gly Gly Thr Ile Arg
      1055                1060                1065

Glu Asn Ile Ala Tyr Gly Ala Ser Asn Asn Asn Lys Val Asp
      1070                1075                1080

Glu Thr Glu Ile Ile Glu Ala Arg Ala Ala Asn Ala His Asp
      1085                1090                1095

Phe Ile Ala Ser Leu Lys Asp Gly Tyr Asp Thr Ser Cys Arg Asp
      1100                1105                1110

Arg Gly Val Gln Leu Ser Gly Gly Gln Lys Gln Arg Ile Ala Ile
      1115                1120                1125

Ala Arg Ala Ile Leu Lys Asn Pro Glu Val Leu Leu Leu Asp Glu
      1130                1135                1140

Ala Thr Ser Ala Leu Asp Ser Gln Ser Glu Lys Leu Val Gln Asp
      1145                1150                1155

Ala Leu Glu Arg Val Met Val Gly Arg Thr Ser Val Val Val Ala
      1160                1165                1170

His Arg Leu Ser Thr Ile Gln Asn Cys Asp Leu Ile Ala Val Leu
      1175                1180                1185

Asp Lys Gly Lys Val Val Glu Lys Gly Thr His Ser Ser Leu Leu
      1190                1195                1200

Ala His Gly Pro Gly Gly Ala Tyr Tyr Ser Leu Ile Ser Leu Gln
      1205                1210                1215

Arg Arg Pro Ala Asn
      1220

<210> SEQ ID NO 116
<211> LENGTH: 3672
<212> TYPE: DNA
<213> ORGANISM: Glycine max

<400> SEQUENCE: 116
atgcatgctg atggcttaga ctggttcctc atgattttg gtctctttgg ggccattggt      60
gatggcatag gcacccctt ggtgttgttt atcaccagca aaattatgaa caatattggt     120

```
ggttttcta gcaacatagg cagcactttc atccacagca tcaatgagaa tgccgtggtt      180
ttgttatatt tggctggtgg gtctttcatt gcttgtttcc tagagggtta ttgttggaca      240
agaacaggag aaaggcaagc tgcaagaatg agagttaggt accttaaagc agttctcagg      300
caagaagtag catactttga tttgcatgtc acaagcacat cggaggtcat caccagcgtc      360
tctaatgata gcctcgtaat tcaagattgt cttagtgaaa aggtcccaaa cttttttgatg      420 aatgcgtcca tgtttgttgg gagctacata gtggcttttg cattattgtg agagattggcc     480 attgtggggt tccctttttgt ggccctactt gtgatccccg gtttcatgta tgggaggaca      540
ttaatggggt tggctagcaa gataagagaa gagtacaata aagcaggcac aatagcagaa      600
caagcaatat cctccatcag aaccgtttat tcttttgtgg gggaaagcaa gactattgat      660
gctttctctg aagccctaca agggtctgtt gagttgggac tgagacaagg cttagcaaaa      720
ggtttagcta ttggaagcaa tggtgttgtc tttgctatat gggcattcat gtcctattat      780
ggtagcagat tggtcatgta ccatggagct aaaggtggga ctgtatttgc agttggagca      840
gccatagctc ttggaggatt ggcactaggt gctggttttgt cgaacgtgaa gtacttctca      900
gaagcaagta ccgcaggaga acgcataatg gaagtgataa aaagggttcc aaagattgat      960
tctgatagca tggctgagga gattctggag aacgtttcag gggaagttga attcaaccat      1020
gtggactttg tgtacccatc aaggccagac agtgttattc tgaatgattt ctgcctaaag      1080
attccagcag ggaaaacagt ggctttggtt ggagggagtg gctctggaaa atccactgtg      1140
atatcacttt tgcagaggtt ttatgaccca attgagggag agatatttct tgatggtgtg      1200
gccattcaca agttgcaact caagtggttg aggtctcaaa tgggtttggt cagccaagag      1260
cctgcactgt ttgcaactag cattaaagag aatatacttt ttggaagaga agatgccact      1320
caagaagagg ttgtggaggc agcaaaagct tccaatgctc ataatttcat ttcacagttg      1380
ccacaaggat atgatactca ggttggggag agaggagttc aaatgtcagg tggacaaaag      1440
caaagaattg caatagcacg agcaataata aaaaagccac ggattcttct attagatgaa      1500
gcaacaagtg cactagattc tgaatctgaa cgagttgtgc aagaagcatt agacaaagta      1560
gcagtagggc gcacaacaat catcattgca catagattat ccaccataag gaatgcaaat      1620
gtgattgctg ttgtgcaaag tgggaaaatc atggagatgg gatcacacca tgaactaatc      1680
caaaacgaca atggccttta cacctcacta gttcgtctcc aacaagcaaa aaatgaaaaa      1740
gaagacaccc ttttcatcc tactcctcct tcgtccatat cgaacaaaga caatcacaac      1800
acgagtagcc gtaggctctc tgttgtgatg agccgttcta gctccaccaa ctcgataccc     1860
cgtattggtg gtggtgacga taacaatatt gttgaagaag tagtggaaga taacaagcca     1920
ccacttccct catttcgaag gttgctcgca ctgaacattc ccgagtggaa gcaagcatgt     1980
ttagggtgtt tgaatgcggt gttgtttggt gcaattcagc ctgtgtatgc atttgcaatg     2040
gggtcagtga tatctgttta cttcctccca gaccataatg agataaagaa gaaaactatg     2100
atctattcac tttgtttcct agggttggct gtgttctcct tagtggttaa tatcctccag     2160
cattacaact ttgcttacat aggagagtac ttgactaaaa ggatcagaga agaatgtttt     2220
tccaagatac tcacttttga agttggatgg tttgatcaag atgaaaattc cacaggtgct     2280
gtttgttcta gacttgccaa agaagccaat gtgaatggtc tagtggtaca aaccatttca     2340
gcagtggtaa tagcttttac aatgggccta atcattgcat ggaggttggc cattgttatg     2400
atagcagttc aacccattat catagcatgt ttctacacaa ggcgtgtcct tctcaagagc     2460
atgtctagta aggccatcaa ggcccaagat gaaagtagca agatagctgt tgaagctgtt     2520
```

-continued

```
tccaacctca gaacaatcac agcattttct tcccaagata ggatccttaa aatgctcgaa    2580
aaggcccaag aaggcccgag ccgtgaaagc attcgacaat catggtttgc gggcattggg    2640
cttgcatgtt cccaaagcct tacattttgc acttgggctt tggacttttg gtatggaggc    2700
aagcttgtgt ttcagggctt cataaatgcc aaagcattgt ttgagacctt catgatttta    2760
gtgagcacag taggggttat tgcagatgct ggtagcatga ccaatgacct agctaaaggg    2820
gctgatgctg tgggctcagt ttttgcaatc ttagataagt acacaaaaat tgagccagat    2880
gatgacatag atgggtacaa gcctgaaaag ctaacaggga aaatagagct tcatgatgtc    2940
cattttgcat acccagctag gcccaatgtg atgatcttcc aaggcttctc aatcaaaatt    3000
gatgcaggca gatcaacagc attggtcggg caaagtggct ctggaaaatc aacaatcata    3060
ggcttaattg agagattcta tgaccctcta aaagggattg tgaccattga tggtagagac    3120
ataaaatcat accaccttag gtcactaagg aagcatattg ctcttgtaag ccaagagcca    3180
acattgtttg gtgggaccat aagggaaaat attgcatatg gggcatctaa taataataac    3240
aaggttgatg aaactgagat catagaagca gctagggcag ctaatgctca tgatttcatt    3300
gcaagcctaa aggatggtta tgacacatcg tgtggagata gaggagtgca actctctggg    3360
ggtcaaaagc aaagaattgc aatagctaga gccatattga agaatccaga agtgttgttg    3420
ttggatgaag ccacaagtgc cctagatagc aatcagaaa aattggtgca agatgctcta    3480
gaaagggtga tggtggggag aactagtgtg gtggtggctc acaggttaag cacaatacaa    3540
aattgtgacc taattgctgt gttagataag ggaaaagtgg tggagaaagg gacccactca    3600
tctttgttgg ctcatggacc aggtggagct tattactctt tgataagttt acaaagaaga    3660
ccagcaaatt aa                                                        3672
```

<210> SEQ ID NO 117
<211> LENGTH: 1223
<212> TYPE: PRT
<213> ORGANISM: Glycine max

<400> SEQUENCE: 117

```
Met His Ala Asp Gly Leu Asp Trp Phe Leu Met Ile Phe Gly Leu Phe
1               5                   10                  15

Gly Ala Ile Gly Asp Gly Ile Gly Thr Pro Leu Val Leu Phe Ile Thr
            20                  25                  30

Ser Lys Ile Met Asn Asn Ile Gly Gly Phe Ser Ser Asn Ile Gly Ser
        35                  40                  45

Thr Phe Ile His Ser Ile Asn Glu Asn Ala Val Val Leu Leu Tyr Leu
    50                  55                  60

Ala Gly Gly Ser Phe Ile Ala Cys Phe Leu Glu Gly Tyr Cys Trp Thr
65                  70                  75                  80

Arg Thr Gly Glu Arg Gln Ala Ala Arg Met Arg Val Arg Tyr Leu Lys
                85                  90                  95

Ala Val Leu Arg Gln Glu Val Ala Tyr Phe Asp Leu His Val Thr Ser
            100                 105                 110

Thr Ser Glu Val Ile Thr Ser Val Ser Asn Asp Ser Leu Val Ile Gln
        115                 120                 125

Asp Cys Leu Ser Glu Lys Val Pro Asn Phe Leu Met Asn Ala Ser Met
    130                 135                 140

Phe Val Gly Ser Tyr Ile Val Ala Phe Ala Leu Leu Trp Arg Leu Ala
145                 150                 155                 160

Ile Val Gly Phe Pro Phe Val Ala Leu Leu Val Ile Pro Gly Phe Met
                165                 170                 175
```

```
Tyr Gly Arg Thr Leu Met Gly Leu Ala Ser Lys Ile Arg Glu Glu Tyr
            180                 185                 190

Asn Lys Ala Gly Thr Ile Ala Glu Gln Ala Ile Ser Ser Ile Arg Thr
            195                 200                 205

Val Tyr Ser Phe Val Gly Glu Ser Lys Thr Ile Asp Ala Phe Ser Glu
            210                 215                 220

Ala Leu Gln Gly Ser Val Glu Leu Gly Leu Arg Gln Gly Leu Ala Lys
225                 230                 235                 240

Gly Leu Ala Ile Gly Ser Asn Gly Val Val Phe Ala Ile Trp Ala Phe
                245                 250                 255

Met Ser Tyr Tyr Gly Ser Arg Leu Val Met Tyr His Gly Ala Lys Gly
                260                 265                 270

Gly Thr Val Phe Ala Val Gly Ala Ala Ile Ala Leu Gly Gly Leu Ala
            275                 280                 285

Leu Gly Ala Gly Leu Ser Asn Val Lys Tyr Phe Ser Glu Ala Ser Thr
            290                 295                 300

Ala Gly Glu Arg Ile Met Glu Val Ile Lys Arg Val Pro Lys Ile Asp
305                 310                 315                 320

Ser Asp Ser Met Ala Glu Glu Ile Leu Glu Asn Val Ser Gly Glu Val
                325                 330                 335

Glu Phe Asn His Val Asp Phe Val Tyr Pro Ser Arg Pro Asp Ser Val
                340                 345                 350

Ile Leu Asn Asp Phe Cys Leu Lys Ile Pro Ala Gly Lys Thr Val Ala
            355                 360                 365

Leu Val Gly Gly Ser Gly Ser Gly Lys Ser Thr Val Ile Ser Leu Leu
            370                 375                 380

Gln Arg Phe Tyr Asp Pro Ile Glu Gly Glu Ile Phe Leu Asp Gly Val
385                 390                 395                 400

Ala Ile His Lys Leu Gln Leu Lys Trp Leu Arg Ser Gln Met Gly Leu
                405                 410                 415

Val Ser Gln Glu Pro Ala Leu Phe Ala Thr Ser Ile Lys Glu Asn Ile
            420                 425                 430

Leu Phe Gly Arg Glu Asp Ala Thr Gln Glu Glu Val Val Glu Ala Ala
            435                 440                 445

Lys Ala Ser Asn Ala His Asn Phe Ile Ser Gln Leu Pro Gln Gly Tyr
450                 455                 460

Asp Thr Gln Val Gly Glu Arg Gly Val Gln Met Ser Gly Gly Gln Lys
465                 470                 475                 480

Gln Arg Ile Ala Ile Ala Arg Ala Ile Ile Lys Lys Pro Arg Ile Leu
                485                 490                 495

Leu Leu Asp Glu Ala Thr Ser Ala Leu Asp Ser Glu Ser Glu Arg Val
            500                 505                 510

Val Gln Glu Ala Leu Asp Lys Val Ala Val Gly Arg Thr Thr Ile Ile
            515                 520                 525

Ile Ala His Arg Leu Ser Thr Ile Arg Asn Ala Asn Val Ile Ala Val
            530                 535                 540

Val Gln Ser Gly Lys Ile Met Glu Met Gly Ser His Glu Leu Ile
545                 550                 555                 560

Gln Asn Asp Asn Gly Leu Tyr Thr Ser Leu Val Arg Leu Gln Gln Ala
                565                 570                 575

Lys Asn Glu Lys Glu Asp Thr Leu Phe His Pro Thr Pro Ser Ser
                580                 585                 590

Ile Ser Asn Lys Asp Asn His Asn Thr Ser Ser Arg Arg Leu Ser Val
```

```
              595                 600                 605
Val Met Ser Arg Ser Ser Thr Asn Ser Ile Pro Arg Ile Gly Gly
610                 615                 620

Gly Asp Asp Asn Asn Ile Val Glu Glu Val Val Glu Asp Asn Lys Pro
625                 630                 635                 640

Pro Leu Pro Ser Phe Arg Arg Leu Leu Ala Leu Asn Ile Pro Glu Trp
                    645                 650                 655

Lys Gln Ala Cys Leu Gly Cys Leu Asn Ala Val Leu Phe Gly Ala Ile
                660                 665                 670

Gln Pro Val Tyr Ala Phe Ala Met Gly Ser Val Ile Ser Val Tyr Phe
            675                 680                 685

Leu Pro Asp His Asn Glu Ile Lys Lys Lys Thr Met Ile Tyr Ser Leu
690                 695                 700

Cys Phe Leu Gly Leu Ala Val Phe Ser Leu Val Val Asn Ile Leu Gln
705                 710                 715                 720

His Tyr Asn Phe Ala Tyr Ile Gly Glu Tyr Leu Thr Lys Arg Ile Arg
                    725                 730                 735

Glu Arg Met Phe Ser Lys Ile Leu Thr Phe Glu Val Gly Trp Phe Asp
                740                 745                 750

Gln Asp Glu Asn Ser Thr Gly Ala Val Cys Ser Arg Leu Ala Lys Glu
            755                 760                 765

Ala Asn Val Asn Gly Leu Val Val Gln Thr Ile Ser Ala Val Val Ile
770                 775                 780

Ala Phe Thr Met Gly Leu Ile Ile Ala Trp Arg Leu Ala Ile Val Met
785                 790                 795                 800

Ile Ala Val Gln Pro Ile Ile Ile Ala Cys Phe Tyr Thr Arg Arg Val
                    805                 810                 815

Leu Leu Lys Ser Met Ser Ser Lys Ala Ile Lys Ala Gln Asp Glu Ser
                820                 825                 830

Ser Lys Ile Ala Val Glu Ala Val Ser Asn Leu Arg Thr Ile Thr Ala
            835                 840                 845

Phe Ser Ser Gln Asp Arg Ile Leu Lys Met Leu Glu Lys Ala Gln Glu
850                 855                 860

Gly Pro Ser Arg Glu Ser Ile Arg Gln Ser Trp Phe Ala Gly Ile Gly
865                 870                 875                 880

Leu Ala Cys Ser Gln Ser Leu Thr Phe Cys Thr Trp Ala Leu Asp Phe
                    885                 890                 895

Trp Tyr Gly Gly Lys Leu Val Phe Gln Gly Phe Ile Asn Ala Lys Ala
                900                 905                 910

Leu Phe Glu Thr Phe Met Ile Leu Val Ser Thr Gly Arg Val Ile Ala
            915                 920                 925

Asp Ala Gly Ser Met Thr Asn Asp Leu Ala Lys Gly Ala Asp Ala Val
930                 935                 940

Gly Ser Val Phe Ala Ile Leu Asp Lys Tyr Thr Lys Ile Glu Pro Asp
945                 950                 955                 960

Asp Asp Ile Asp Gly Tyr Lys Pro Glu Lys Leu Thr Gly Lys Ile Glu
                    965                 970                 975

Leu His Asp Val His Phe Ala Tyr Pro Ala Arg Pro Asn Val Met Ile
                980                 985                 990

Phe Gln Gly Phe Ser Ile Lys Ile Asp Ala Gly Arg Ser Thr Ala Leu
            995                 1000                1005

Val Gly Gln Ser Gly Ser Gly Lys Ser Thr Ile Ile Gly Leu Ile
1010                1015                1020
```

-continued

| | | | | | | | | | | | | |
|---|---|---|---|---|---|---|---|---|---|---|---|---|
| Glu | Arg | Phe | Tyr | Asp | Pro | Leu | Lys | Gly | Ile | Val | Thr | Ile Asp Gly |
| | 1025 | | | | 1030 | | | | | 1035 | | |
| Arg | Asp | Ile | Lys | Ser | Tyr | His | Leu | Arg | Ser | Leu | Arg | Lys His Ile |
| | 1040 | | | | 1045 | | | | | 1050 | | |
| Ala | Leu | Val | Ser | Gln | Glu | Pro | Thr | Leu | Phe | Gly | Gly | Thr Ile Arg |
| | 1055 | | | | 1060 | | | | | 1065 | | |
| Glu | Asn | Ile | Ala | Tyr | Gly | Ala | Ser | Asn | Asn | Asn | Asn | Lys Val Asp |
| | 1070 | | | | 1075 | | | | | 1080 | | |
| Glu | Thr | Glu | Ile | Ile | Glu | Ala | Ala | Arg | Ala | Ala | Asn | Ala His Asp |
| | 1085 | | | | 1090 | | | | | 1095 | | |
| Phe | Ile | Ala | Ser | Leu | Lys | Asp | Gly | Tyr | Asp | Thr | Ser | Cys Gly Asp |
| | 1100 | | | | 1105 | | | | | 1110 | | |
| Arg | Gly | Val | Gln | Leu | Ser | Gly | Gly | Gln | Lys | Gln | Arg | Ile Ala Ile |
| | 1115 | | | | 1120 | | | | | 1125 | | |
| Ala | Arg | Ala | Ile | Leu | Lys | Asn | Pro | Glu | Val | Leu | Leu | Leu Asp Glu |
| | 1130 | | | | 1135 | | | | | 1140 | | |
| Ala | Thr | Ser | Ala | Leu | Asp | Ser | Gln | Ser | Glu | Lys | Leu | Val Gln Asp |
| | 1145 | | | | 1150 | | | | | 1155 | | |
| Ala | Leu | Glu | Arg | Val | Met | Val | Gly | Arg | Thr | Ser | Val | Val Val Ala |
| | 1160 | | | | 1165 | | | | | 1170 | | |
| His | Arg | Leu | Ser | Thr | Ile | Gln | Asn | Cys | Asp | Leu | Ile | Ala Val Leu |
| | 1175 | | | | 1180 | | | | | 1185 | | |
| Asp | Lys | Gly | Lys | Val | Val | Glu | Lys | Gly | Thr | His | Ser | Ser Leu Leu |
| | 1190 | | | | 1195 | | | | | 1200 | | |
| Ala | His | Gly | Pro | Gly | Gly | Ala | Tyr | Tyr | Ser | Leu | Ile | Ser Leu Gln |
| | 1205 | | | | 1210 | | | | | 1215 | | |
| Arg | Arg | Pro | Ala | Asn | | | | | | | | |
| | 1220 | | | | | | | | | | | |